United States Patent
Ito et al.

(10) Patent No.: US 6,172,067 B1
(45) Date of Patent: Jan. 9, 2001

(54) 2-SUBSTITUTED-1-PIPERIDYL BENZIMIDAZOLE COMPOUNDS AS ORL1-RECEPTOR AGONISTS

(75) Inventors: Fumitaka Ito; Hirohide Noguchi; Hiroshi Kondo, all of Aidni-Ken (JP)

(73) Assignee: Pfizer Inc., New York, NY (US)

( * ) Notice: Under 35 U.S.C. 154(b), the term of this patent shall be extended for 0 days.

(21) Appl. No.: 09/369,208

(22) Filed: Aug. 5, 1999

Related U.S. Application Data

(63) Continuation of application No. PCT/IB98/01206, filed on Aug. 6, 1998.

(51) Int. Cl.[7] .................... A61K 31/454; A61K 31/496; C07D 401/04; C07D 401/14; C07D 403/14; A61P 25/00

(52) U.S. Cl. ................... 514/252.13; 514/235.8; 514/316; 514/322; 544/124; 544/364; 546/187; 546/199

(58) Field of Search .................. 546/187, 199; 544/364, 124; 514/254, 316, 322, 252.13, 235.8

(56) References Cited

U.S. PATENT DOCUMENTS

| | | | |
|---|---|---|---|
| 5,718,912 | * 2/1998 | Thompson | 424/427 |
| 5,821,219 | 10/1998 | Grandy et al. | 514/2 |
| 5,834,478 | * 11/1998 | Ito | 514/282 |
| 5,866,346 | 2/1999 | Yu | 435/7.21 |
| 5,929,035 | 7/1999 | Owyang | 514/13 |
| 5,998,375 | 12/1999 | Thøgersen et al. | 514/13 |

FOREIGN PATENT DOCUMENTS

| | | |
|---|---|---|
| 813065A2 | 12/1997 | (EP) . |
| 990653A1 | 4/2000 | (EP) . |
| 52-97978 | * 8/1977 | (JP) . |
| 9707208 | 2/1997 | (WO) . |
| 9707212 | 2/1997 | (WO) . |
| 97/40035 | * 10/1997 | (WO) . |
| 0006545 | 2/2000 | (WO) . |

OTHER PUBLICATIONS

David Julius, Nature, vol. 377(6549), p. 476 (1995).
Henderson, et al., TIPS, vol. 18, pp. 293–300 (1997).

* cited by examiner

*Primary Examiner*—Evelyn Mei Huang
(74) *Attorney, Agent, or Firm*—Peter C. Richardson; Paul H. Ginsburg; Elsa Djuardi

(57) ABSTRACT

A compound of the formula:

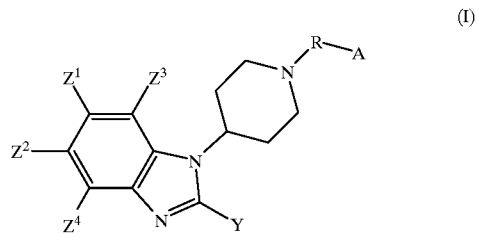

(I)

or a pharmaceutically acceptable salt thereof, wherein R is unsubstituted, mono-, di- or tri-substituted ($C_3$–$C_{11}$) cycloalkyl or ($C_3$–$C_{11}$)cycloalkenyl or the like, A is unsubstituted ($C_1$–$C_7$)alkyl or ($C_2$–$C_5$)alkenyl, or unsubstituted, mono-, di- or tri-substituted aryl, or aromatic-heterocyclic or the like, Y is hydrogen, halo, amino or mercapto, or unsubstituted, mono-, di- or tri- substituted ($C_1$–$C_{10}$)alkyl-M—, ($C_3$–$C_7$)cycloalkyl-M—, ($C_2$–$C_6$)alkenyl-M—, ($C_1$–$C_4$)alkyl-NH-(($C_1$–$C_4$)alkyl)-M—, di($C_1$–$C_4$)alkyl-N-(($C_1$–$C_4$)alkyl)-M—, aryl-M—, aromatic or non-aromatic heterocyclic-M—, aryl-($C_1$–$C_5$)alkyl-M— or aromatic non-aromatic heterocyclic-($C_1$–$C_5$)alkyl-M—, wherein M is a covalent bond O, S, NH or the like, or the like; $Z^1$, $Z^2$, $Z^3$ and $Z^4$ are hydrogen or the like, has ORL1-receptor agonist activity, and are useful as analgesics or the like in mammalian subjects.

22 Claims, No Drawings

2-SUBSTITUTED-1-PIPERIDYL BENZIMIDAZOLE COMPOUNDS AS ORL1-RECEPTOR AGONISTS

This application is the continuation of PCT/IB98/01206, filed Aug. 6, 1998.

TECHNICAL FIELD

This invention relates to novel 1-substituted-piperidin-4-yl 2-substituted benzimidazole compounds, and their salts, pharmaceutical compositions containing them, their medical uses, processes for preparing those compounds and intermediate compounds useful in the processes. The compounds of this invention have activity as selective ORL1-receptor agonists, and as such are useful in treating or preventing disorders or medical conditions selected from pain, inflammatory diseases and the like.

BACKGROUND ART

In spite of their usefulness as analgesics, usage of opioids such as morphine and heroin are strictly limited. This is because these drugs induce side effects such as euphoria, respiratory depression or constipation. Further, multiple dosage of the drugs cause addiction. Thus, there has been a long-felt need to provide analgesics with reduced side effects.

From the above point of view, considerable pharmacological and biochemical studies have been carried out to identify opioid receptors and their endogenous ligands to prepare peptide and non-peptide opioid ligands for the receptors. In the recent past, amino acid sequences of mu-($\mu$-), delta ($\delta$-) and kappa ($\kappa$-) opioid receptor subtypes have been identified and reported. Subsequently, a novel receptor subtype was identified and termed ORL1-receptor, and Meunier, J.-C et al. reported the isolation and structure of the endogenous agonist of the receptor (*Nature*, Vol. 377, pp. 532–535, Oct. 12, 1995). It is suggested that the agonist compounds for ORL1-receptor be effective in neurogenic inflammation (*Tips*, Vol. 18, pp. 293–300, August 1997). It is also suggested that the agonist compounds be potent analgesics having less psychological side effects and addiction (D. Julius, *Nature*, Vol. 377, p. 476, Oct. 12, 1995).

WO 97/40035 discloses a 2-substituted 1-piperidyl benzimidazolyl compound substituted with a cycloalkyl group at the nitrogen atom of the piperidine group.

BRIEF DISCLOSURE OF THE INVENTION

The present invention provides a compound of the following formula:

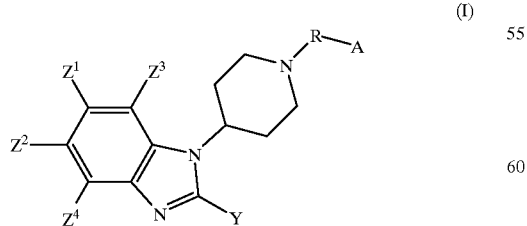

(I)

or a salt thereof, wherein

R is selected from the group consisting of $(C_3-C_{11})$ cycloalkyl, $(C_6-C_{16})$bicycloalkyl, $(C_6-C_{16})$ tricycloalkyl and $(C_8-C_{16})$tetracyclyoalkyl, wherein said groups are partially saturated, fully saturated or fully unsaturated and are optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di, or tri-halo $(C_1-C_7)$alkyl, $(C_2-C_5)$alkenyl, $(C_2-C_5)$alkynyl, phenyl-$(C_1-C_5)$alkyl, aryl, and aromatic or non-aromatic heterocyclic comprising four to ten ring atoms wherein one to four ring atoms are independently selected from heteroatoms (i.e., O, S and N), and said phenyl moiety in phenyl-$(C_1-C_5)$alkyl, aryl, or aromatic or non-aromatic heterocyclic being optionally substituted with up to three substituents independently selected from the group consisting of halo, hydroxy, $(C_1-C_4)$alkyl, halo $(C_1-C_4)$alkyl, $(C_1-C_4)$ alkoxy, halo $(C_1-C_4)$alkoxy, $(C_1-C_4)$alkyl-CO—, phenyl, benzyl, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl)-N—, $(C_1-C_4)$alkyl-CO—NH—, $(C_1-C_4)$alkyl-NH—CO—, hydrazino, azido, ureido, amidino, guanidino, oxo and =N—OH;

Y is selected from the group consisting of hydrogen, halo, amino, mercapto, $(C_1-C_{12})$alkyl-M—, $(C_3-C_7)$ cycloalkyl-M—, $(C_2-C_6)$alkenyl-M—, aryl-M—, aromatic or non-aromatic heterocyclic-M—, aryl-$(C_1-C_5)$ alkyl-M—, aromatic or non-aromatic heterocyclic-$(C_1-C_5)$alkyl-M—, said aromatic or non-aromatic heterocyclic moiety of said groups comprising four to ten ring atoms wherein one to four ring atoms are independently selected from heteroatoms (i.e., O, S and N), and M is selected from the group consisting of a covalent bond, O, S, SO, $SO_2$, CO (i.e., C(=O)), NQ (i.e., N(Q)), NQCO (i.e., N(Q)C(=O)), and CONQ (i.e., C(=O)N(Q)), wherein Q is selected from the group consisting of hydrogen and $(C_1-C_6)$alkyl, said $(C_1-C_{12})$alkyl, $(C_3-C_7)$cycloalkyl or $(C_2-C_6)$ alkenyl moiety in said groups being optionally substituted with up to three (preferably zero to two) substituents independently selected from the group consisting of halo, hydroxy, amino, $(C_1-C_4)$alkyl-NH—, di-$(C_1-C_4)$alkyl-N—, hydrazino, azido, ureido, amidino, guanidino, $(C_1-C_4)$alkoxy, $(C_1-C_4)$ alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with up to three (preferably zero to two) substituents independently selected from the group consisting of halo, hydroxy, $(C_1-C_4)$alkyl, halo $(C_1-C_4)$alkyl, $(C_1-C_4)$alkoxy, halo $(C_1-C_4)$alkoxy, $(C_1-C_4)$alkyl-CO—, phenyl, benzyl, —CHO, cyano, $(C_1-C_4)$ alkyl-CO—, $NH_2$—CO—, $NH_2$—$CH_2$—, amino, $(C_1-C_4)$alkyl-NH—, di$(C_1-C_4$ alkyl)-N—, $(C_1-C_4)$ alkyl-CO—NH—, $(C_1-C_4)$alkyl-NH—CO—, hydrazino, azido, ureido, amidino, guanidino, oxo and =N—OH; and $Z^1$, $Z^2$, $Z^3$ and $Z^4$ are each independently selected from the group consisting of hydrogen, halo, $(C_1-C_4)$alkyl, halo $(C_1-C_4)$alkyl, $(C_1-C_4)$alkoxy, $(C_1-C_4)$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$alkyl-$SO_2$—NH—, phenyl and naphthyl.

This invention also relates to processes for preparing compounds of the formula (I) defined as above which comprises (a) coupling compounds of formulae

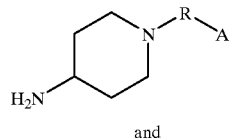

(VII)

and (VIII)

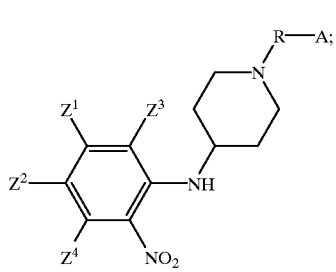

wherein R, A and $Z^1$ to $Z^4$ are defined as above, and L is halo to give the compound of formula (IX)

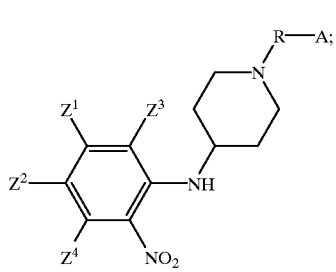

(b) reducing the compound of formula (IX) to the compound of formula (X)

(X)

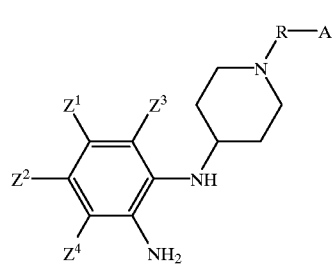

by either reduction or hydrogenation; and (c) subjecting the resulting compound of formula (X) to benzimidazole formation to give the compound of formula (I).

This invention also relates to an intermediate compound of formula (IX)

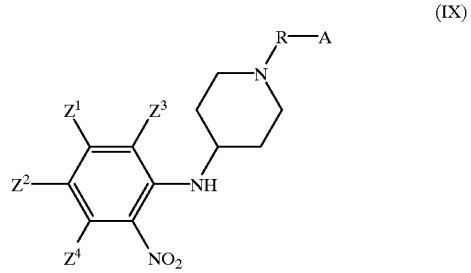

which is useful in the above-mentioned processes for preparing a compound of formula (I) wherein R is selected from the group consisting of $(C_3-C_{11})$cycloalkyl, $(C_6-C_{16})$bicycloalkyl, $(C_6-C_{16})$tricycloalkyl and $(C_8-C_{16})$tetracyclyoalkyl, wherein said groups are partially saturated, fully saturated or fully unsaturated and are optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di, or tri-halo $(C_1-C_7)$alkyl, $(C_2-C_5)$alkenyl, $(C_2-C_5)$alkynyl, phenyl-$(C_1-C_5)$alkyl, aryl, and aromatic or non-aromatic heterocyclic comprising four to ten ring atoms wherein one to four ring atoms are independently selected from heteroatoms, and said phenyl moiety in phenyl-$(C_1-C_5)$alkyl, aryl, or aromatic or non-aromatic heterocyclic being optionally substituted with up to three substituents independently selected from the group consisting of halo, hydroxy, $(C_1-C_4)$alkyl, halo $(C_{1-4})$alkyl, $(C_1-C_4)$alkoxy, halo $(C_{1-4})$alkoxy, $(C_1-C_4)$alkyl-CO—, phenyl, benzyl, —CHO, cyano, $(C_1-C_4)$alkyl-CO—, $NH_2$—CO—, $NH_2$—$CH_2$—, amino, $(C_1-C_4)$alkyl-NH—, di($(C_1-C_4)$alkyl)-N—, $(C_1-C_4)$alkyl-CO—NH—, $(C_1-C_4)$alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, $(C_1-C_4)$alkyl, halo $(C_1-C_4)$alkyl, $(C_{1-4})$alkoxy, $(C_{1-4})$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$alkyl-$SO_2$—NH—, phenyl and naphthyl.

This invention also relates to an intermediate compound of formula (X)

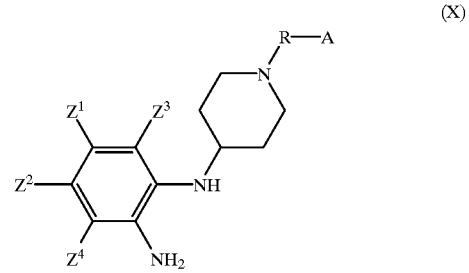

which is useful in the above-mentioned processes for preparing a compound of formula (I) wherein R is selected from the group consisting of $(C_3-C_{11})$ cycloalkyl, $(C_6-C_{16})$bicycloalkyl, $(C_6-C_{16})$ tricycloalkyl and $(C_8-C_{16})$tetracyclyoalkyl, wherein said groups are partially saturated, fully saturated or fully unsaturated and are optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di, or tri-halo $(C_1-C_7)$alkyl, $(C_2-C_5)$alkenyl, $(C_2-C_5)$alkynyl, phenyl-$(C_1-C_5)$alkyl, aryl, and aromatic or non-aromatic heterocyclic comprising four to ten ring atoms wherein one to four ring atoms are independently selected from heteroatoms, and said phenyl moiety in phenyl-$(C_1-C_5)$alkyl, aryl, or aromatic or non-aromatic heterocyclic being optionally substituted with up to three substituents independently selected from the group consisting of halo, hydroxy, $(C_1-C_4)$alkyl, halo $(C_1C_4)$alkyl, $(C_1-C_4)$ alkoxy, halo $(C_1-C_4)$alkoxy, $(C_1-C_4)$alkyl-CO—, phenyl, benzyl, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl)-N—, $(C_1-C_4)$alkyl-CO—NH—, $(C_1-C_4)$alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, $(C_1-C_4)$alkyl, halo $(C_1-C_4)$alkyl, $(C_{1-4})$alkoxy, $(C_{1-4})$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$ alkyl-$SO_2$—NH—, phenyl and naphthyl.

DETAILED DESCRIPTION OF THE INVENTION

The term "alkyl", as used herein, means a straight or branched saturated monovalent hydrocarbon radical including, but not limited to, methyl, ethyl, propyl, isopropyl, n-butyl, sec-butyl, tert-butyl and the like.

The term "cycloalkyl", as used herein, means a saturated carbocyclic radical including, but not limited to, cyclopropyl, cyclobutyl, cyclohexyl, cycloheptyl, cyclooctyl, cyclononyl, cyclodecyl and the like.

The term "$C_5-C_9$ alkenyl ring", as used herein, means a carbocyclic radical having at least one double bond including, but not limited to, cyclopentenyl, cyclohexenyl, cycloheptenyl, cyclooctenyl, cyclononenyl, cyclodecenyl and the like.

The term "alkenyl", as used herein, means a hydrocarbon radical having at least one double bond including, but not limited to, ethenyl, propenyl, 1-butenyl, 2-butenyl and the like.

The term "alkynyl", as used herein, means a hydrocarbon radical having at least one triple bond including, but not limited to, ethynyl, propynyl, 1-butynyl, 2-butynyl and the like.

The term "alkoxy", as used herein, means an O-alkyl group wherein "alkyl" is defined above.

The term "halo", as used herein, refers to F, Cl, Br or I, preferably F or Cl.

The term "aryl", as used herein, means a monocyclic or bicyclic aromatic carbocyclic ring system of 6–11 carbon atoms including, but not limited to, phenyl, naphthyl, indanyl, (1,2,3,4)-tetaahydronaphthyl, indenyl, isoindenyl and the like.

The term "aromatic or non-aromatic heterocyclic" or "heterocyclic", as used herein, unless otherwise indicated, includes aromatic and non-aromatic heterocyclic groups having four to ten atoms comprising one to four heteroatoms each selected from O, S and N. Such heterocyclic groups include those having a fused benzene ring optionally substituted with an oxo moiety. Examples of the aromatic and non-aromatic heterocyclic are azetidinyl, fuiryl, thienyl, pyrrolyl, pyrroldinyl, oxazolyl, isooxazolyl, thiazolyl, isothiazolyl, imidazolyl, pyrazolyl, triazolyl, furazanyl, tetrazolyl, pyranyl, thiinyl, pyridyl, piperidyl (or piperidinyl), piperidino, oxazinyl, morpholinyl, morphorino, thiamorpholino, thiazinyl, pyridazinyl, pyrimidinyl, pyrazinyl, piperazinyl, piperazino, triazinyl, benzofuranyl, isobenzofuranyl, benzothiophenyl, indolyl, isoindolyl, benzoxazolyl, benzothiazolyl, indazolyl, benzimidazolyl, chromanyl, isochromanyl, quinolyl, isoquinolyl, cinnolinyl, phthalazinyl, quinazolinyl and quinoxalinyl.

Preferred heterocyclics are four to six membered heterocyclic comprising one to two heteroatoms. Examples of the four to six membered heterocyclic include piperidyl, piperidino, piperazinyl, piperazino.

The term "bi-, tri- or tetra-cyclic ring" means hydrocarbon cyclic groups of 6 to 16 carbon atoms, having two to four rings therein, including, but not limited to, decahydronaphthalene, bicyclo[2.2.1.]heptane, bicyclo [3.2.1]ociane, bicyclo[3.3.1]nonane, adamantane and tricyclo[5.2.1.0$^{2,6}$]decane.

The definition "A is attached to the carbon atom of R with which R is attached to the nitrogen atom of the piperidine ring" means the chemical formulation described with the following chemical formula wherein the circle represents R.

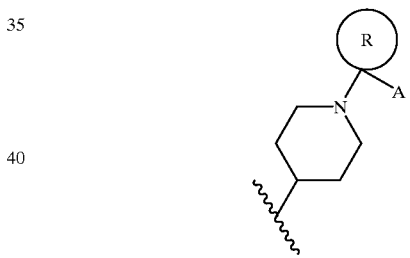

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred group of compounds of the present invention includes compounds of formula (I) wherein R is selected from the group consisting of $(C_3-C_{11})$ cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

more preferably R is selected from the group consisting of $(C_3-C_{11})$cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

more preferably R is $C_6-C_{10}$ cycloalkyl; and more preferably R is $(C_7-C_9)$cycloalkyl.

A preferred group of compounds of the present invention includes compounds of formula (I) wherein A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four to six ring atoms wherein one to two ring atoms are independently selected from heteroatoms, and aryl, or aromatic or non-aromatic heterocyclic being optionally substituted with up to three substituents independently selected from halo, $(C_1-C_4)$alkyl, halo $(C_1-C_4)$alkyl, $(C_1-C_4)$alkoxy, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl$)$-N—, $(C_{1-4})$alkyl-CO—NH— and $(C_{1-4})$alkyl-NH—CO—;

more preferably A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, thiinyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, $(C_1-C_4)$alkyl, halo $(C_1-C_4)$alkyl and $(C_1-C_4)$alkoxy;

more preferably A is attached to the carbon atom of R with which R is attached to the nitrogen atom of the piperidine ring, and is selected from the group consisting of $(C_1-C_7)$alkyl and $(C_2-C_5)$alkenyl, phenyl and naphthyl; and more preferably A is attached to the carbon atom of R with which R is attached to the nitrogen atom of the piperidine ring, and is selected from the group consisting of methyl and phenyl.

A preferred group of compounds of the present invention includes compounds of formula (I) wherein Y is selected from the group consisting of hydrogen, halo, amino, mercapto, $(C_1-C_{10})$alkyl-M—, $(C_3-C_7)$cycloalkyl-M—, $(C_2-C_6)$alkenyl-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aromatic or non-aromatic heterocyclic moiety of said groups comprising four to six ring atoms wherein one to two ring atoms are independently selected from heteroatoms, M is selected from group consisting of a covalent bond, O, S, SO, $SO_2$, CO, NH, N$((C_1-C_6)$alkyl$)$, CONH and NHCO, said $(C_1-C_{10})$alkyl, $(C_3-C_7)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with substituents independently selected from the group consisting of halo, hydroxy, $(C_1-C_4)$alkyl, halo $(C_1-C_4)$alkyl, $(C_1-C_4)$alkoxy, $(C_1-C_4)$alkyl-CO—, phenyl, benzyl, amino, $(C_1-C_4)$alkyl-NH—, di$((C_1-C_4)$alkyl$)$-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH;

more preferably Y is selected from the group consisting of hydrogen, halo, amino, mercapto, $(C_1-C_{10})$alkyl-M—, $(C_3-C_7)$cycloalkyl-M—, $(C_2-C_6)$alkenyl-M—, $(C_1-C_4)$alkyl-NH—$((C_1-C_4)$alkyl$)$-M—, di$(C_1-C_4)$alkyl-N—$((C_1-C_4)$alkyl$)$-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aryl moiety of said groups being selected from the group consisting of phenyl and naphthyl, said aromatic or non-aromatic heterocyclic moiety of said groups being selected from the group consisting of azetidinyl, fuiryl, pyrrolidinyl, thienyl, pyridyl, piperidyl, piperidino, morpholinyl, morphorino, pyrimidiny, pyrazinyl, pyridazinyl, aziridinyl, pyrrolidinyl, piperazinyl and thiamorpholino, M is selected from the group consisting of a covalent bond, O, S, SO, $SO_2$, CO, NH, CONH, N$((C_1-C_6)$alkyl$)$ and NHCO, said $(C_1-C_{10})$alkyl, $(C_3-C_7)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with up to three substituents selected from the group consisting of halo, hydroxy, $(C_1-C_4)$alkyl, halo $(C_1-C_4)$alkyl, $(C_{C4})$alkoxy, $(C_1-C_4)$alkyl-CO—, phenyl, benzyl, amino, $(C_1-C_4)$alkyl-NH—, di$((C_1-C_4)$alkyl$)$-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH;

more preferably Y is selected from the group consisting of hydrogen, amino, $(C_1-C_6)$alkyl-M—, piperidyl, piperidino and piperazinyl, M is selected from group consisting of a covalent bond, O, $SO_2$, CO, NH, CONH and NHCO, said alkyl moiety of $C_1-C_6$ alkyl-M— being optionally substituted with up to three substituents independently selected from the group consisting of amino and guanidino, and said piperidyl, piperidino or piperazinyl being optionally substituted with up to three substituents independently selected from $(C_1-C_4)$alkyl; and more preferably Y is selected from the group consisting of amino, $(C_1-C_6)$alkyl-NH—, amino-$(C_1-C_6)$alkyl-O—, amino-$(C_1-C_6)$alkyl-CONH—, amnio-$(C_1-C_6)$alkyl-$SO_2$— and piperazinyl substituted by $(C_1-C_4)$alkyl.

A preferred group of compounds of the present invention includes compounds of formula (I) wherein $Z^1$, $Z^2$, $Z^3$ and $Z^4$ are independently selected from the group consisting of hydrogen and halo;

more preferably $Z^1$ and $Z^2$ are independently selected from the group consisting of hydrogen and halo; and $Z^3$ and $Z^4$ are both hydrogen;

more preferably $Z^1$, $Z^2$, $Z^3$ and $Z^4$ are all hydrogen; and more preferably $Z^1$, $Z^2$, $Z^3$ and $Z^4$ are all hydrogen.

A preferred group of the compounds of the present invention includes the compound of Formula (I), wherein R is selected from the group consisting of $(C_3-C_{11})$cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four to six ring atoms wherein one to two ring atoms are independently selected from heteroatoms, and aryl, or aromatic or non-aromatic heterocyclic being optionally substituted with up to three substituents independently selected from halo, $(C_1-C_4)$alkyl, halo $(C_1-C_4)$alkyl, $(C_1-C_4)$alkoxy, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl$)$-N—, $(C_1-C_4)$alkyl-CO—NH— and $(C_1-C_4)$alkyl-NH—CO—;

Y is selected from the group consisting of hydrogen, halo, amino, mercapto, $(C_1-C_{10})$alkyl-M—, $(C_3-C_7)$cycloalkyl-M—, $(C_2-C_6)$alkenyl-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aromatic or non-aromatic heterocyclic moiety of said groups comprising four to six ring atoms wherein one to two ring atoms are independently selected from heteroatoms, M is selected from group consisting of a covalent bond, O, S, SO, $SO_2$, CO, NH, N($(C_1-C_6)$alkyl), CONH and NHCO, said $(C_1-C_{10})$alkyl, $(C_3-C_7)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with substituents independently selected from the group consisting of halo, hydroxy, $(C_1-C_4)$alkyl, halo $(C_1-C_4)$alkyl, $(C_1-C_4)$alkoxy, $(C_1-C_4)$alkyl-CO—, phenyl, benzyl, amino, $(C_1-C_4)$alkyl-NH—, di$((C_1-C_4)$alkyl$)$-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH;

$Z^1$, $Z^2$, $Z^3$ and $Z^4$ are independently selected from the group consisting of hydrogen and halo.

More preferred compounds of this invention are compounds of formula (I) wherein

R is selected from the group consisting of $(C_3-C_{11})$cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, thiinyl, pyridyl, oxazinyl, thiazinyl, pyridazinyl, pyrimidinyl, pyrazinyl and riazinyl, said aryl or aromatic heterocyclic being optionally substituted with up to three substituents independently selected from the group consisting of halo, $(C_1-C_4)$alkyl, halo $(C_1-C_4)$alkyl and $(C_1-C_4)$alkoxy;

Y is selected from the group consisting of hydrogen, halo, amino, mercapto, $(C_1-C_{10})$alkyl-M—, $(C_3-C_7)$cycloalkyl-M—, $(C_2-C_6)$alkenyl-M—, $(C_1-C_4)$alkyl-NH—$((C_1-C_4)$alkyl$)$-M—, di$(C_1-C_4)$alkyl-N—$((C_1-C_4)$alkyl$)$-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aryl moiety of said groups being selected from the group consisting of phenyl and naphthyl, said aromatic or non-aromatic heterocyclic moiety of said groups being selected from the group consisting of azetidinyl, furyl, pyrrolidinyl, thienyl, pyridyl, piperidyl, piperidino, morpholinyl, morphorino, pyrimidiny, pyrazinyl, pyridazinyl, aziridinyl, pyrrolidinyl, piperazinyl and thiamorpholino, M is selected from the group consisting of a covalent bond, O, S, SO, $SO_2$, CO, NH, CONH, N($(C_1-C_6)$alkyl) and NHCO, said $(C_1-C_{10})$alkyl, $(C_3-C_6)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with up to three substituents selected from the group consisting of halo, hydroxy, $(C_1-C_4)$alkyl, halo $(C_1-C_4)$alkyl, $(C_1-C_4)$alkoxy, $(C_1-C_4)$alkyl-CO—, phenyl, benzyl, amino, $(C_1-C_4)$alkyl-NH—, di$((C_1-C_4)$alkyl$)$-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH;

$Z^1$ and $Z^2$ are independently selected from the group consisting of hydrogen and halo; and $Z^3$ and $Z^4$ are both hydrogen.

A more preferred group of the forgoing compounds of this invention are those compounds of formula (I) wherein R is $(C_6-C_{10})$cycloalkyl;

A is attached to the carbon atom of R with which R is attached to the nitrogen atom of the piperidine ring, and selected from the group consisting of $(C_1-C_7)$alkyl and $(C_2-C_5)$alkenyl, phenyl and naphthyl;

Y is selected from the group consisting of hydrogen, amino, $(C_1-C_6)$alkyl-M—, piperidyl, piperidino and piperazinyl, M is selected from group consisting of a covalent bond, O, $SO_2$, CO, NH, CONH and NHCO, said alkyl moiety of $(C_1-C_6)$alkyl-M— being optionally substituted with up to three substituents independently selected from the group consisting of amino and guanidino, and said piperidyl, piperidino or piperazinyl being optionally substituted with up to three substituents independently selected from $(C_1-C_4)$alkyl; and $Z^1$, $^2$, $Z^3$ and $Z^4$ are all hydrogen.

Particularly preferred group of the forgoing compounds of this invention, designated the B-group compounds, are those compounds of formula (I) wherein R is $(C_7-C_9)$cycloalkyl;

A is attached to the carbon atom of R with which R is attached to the nitrogen atom of the piperidine ring, and selected from the group consisting of methyl and phenyl;

Y is selected from the group consisting of amino, $(C_1-C_6)$ alkyl-NH—, amino-$(C_1-C_6)$alkyl-O—, amino-$(C_1-C_6)$ alkyl-CONH—, amino-$(C_1-C_6)$alkyl-$SO_2$— and piperazinyl substituted by $(C_1-C_4)$alkyl; and $Z^1$, $Z^2$, $Z^3$ and $Z^4$ are all hydrogen.

A group of preferred individual compounds of this invention are selected from the group consisting of N-methyl-1-[1-(1-phenylcycloheptyl)-4-piperidinyl]-1H-benzimidazol-2-amine;

2-(4-methylpiperazino)-1-[1-(1-phenylcycloheptyl)-4-piperidinyl]-1H-benzimidazole;

1-[1-(1-phenylcycloheptyl)-4-piperidinyl]-1H-benzimidazole;

2-(4-methylpiperazino)-1-[1-(1-phenylcyclooctyl)-4-piperidinyl]-1H-benzimidazole;

1-[1-(1-phenylcycloheptyl)-4-piperidinyl]-2-(4-piperidinyl)-1H-benzimidazole;

N-methyl-1-[1-(1-methylcyclononyl)-4-piperidinyl]-1H-benzimidazol-2-amine;

1-[1-(1-phenylcyclononyl)-4-piperidinyl]-1H-benzimidazol-2-amine;

N-{1-[1-(1-phenylcycloheptyl)-4-piperidinyl]-1H-benzimidazol-2-yl}acetamide;

2-(4-methylpiperazino)-1-[1-(1-methylcyclooctyl)-4-piperidinyl]-1H-benzimidazole;

3-amino-1-{1-[1-(1-phenylcycloheptyl)-4-piperidinyl]-1H-benzimidazol-2-yl}-1-propanone;

N-methyl-1-[1-(1-methylcyclooctyl)-4-piperidinyl]-1H-benzimidazol-2-amine;

4-{1-[1-(1-phenylcycloheptyl)-4-piperidinyl]-1H-benzimidazol-2-yl}-1-piperidinecarboximidamide;

4-{1-[1-(1-methylcyclooctyl)-4-piperidinyl]-1H-benzimidazol-2-yl}-1-piperazinecarboximidamide;

2-amino-N-{1-[1-(1-phenylcycloheptyl)-4-piperidinyl]-1H-benzimidazol-2-yl}acetainide;

2-({1-[1(1-phenylcycloheptyl)-4-piperidinyl]-1H-benzimidazol-2-yl}oxy)-1-ethanamine;

3-({1-[1-(1-phenylcycloheptyl)-4-piperidinyl]-1H-benzimidazol-2-yl}sulfonyl)-1-propanamine;

1-[1-(1-phenylcyclooctyl)-4-piperidinyl]-1H-benzimidazol-2-amine;

2-amino-N-{1-[1-(1-phenylcyclooctyl)-4-piperidinyl]-1H-benzimidazol-2-yl}acetamide; and (2S)-2-amino-N-{1-[1-(1-phenylcycloheptyl)-4-piperidinyl]-1H-benzimidazol-2-yl}propanamide or a salt thereof.

A group of more preferred individual compounds of this invention are selected from the group consisting of 2-(4-methylpiperazino)-1-[1-(1-phenylcycloheptyl)-4-piperidinyl]-1H-benzimidazole;

1-[1-(1-phenylcyclononyl)-4-piperidinyl]-1H-benzimidazol-2-amine;

N-methyl-1-[1-(1-methylcyclooctyl)-4-piperidinyl]-1H-benzimidazol-2-amine;

2-amino-N-{1-[1-(1-phenylcycloheptyl)-4-piperidinyl]-1H-benzimidazol-2-yl}acetamide;

2-({1-[1-(1-phenylcycloheptyl)4-piperidinyl]-1H-benzimidazol-2-yl}oxy)-1-ethanamine;

3-({1-[1-(1-phenylcycloheptyl)-4-piperidinyl]-1H-benzimidazol-2-yl}sulfonyl)-1-propanamine; and 2-amino-N-{1-[1-(1-phenylcyclooctyl)4-piperidinyl]-1H-benzimidazol-2-yl}acetamide, or a salt thereof.

This invention also relates to a pharmaceutical composition for the treatment of a disorder or condition mediated by ORL1-receptor and its endogenous ligands in a mammal including a human, or for anesthetizing a mammal including a human, which comprises an effective amount of the compound of formula (I), or a pharmaceutically acceptable salt thereof, and a pharmaceutically acceptable carrier.

More specifically, this invention relates to a pharmaceutical composition for the treatment of a disorder or condition selected from the group consisting of inflammatory diseases, inflammation-related hyperalgesia, eating disorders (e.g., in obesity), arterial blood pressure disorders (i.e., hypertension or hypotension), tolerance to narcotic analgesics such as morphine, dependence on narcotic analgesics such as morphine, anxiety, stress disorders, psychic trauma, schizophrenia, Parkinson's disease, chorea, depressant, Alzheimer's disease, dementias, epilepsy and convulsions, useful as analgesics (for acute, chronic or neuropathic pain), anesthetics, neuroprotective agent or analgesic enhancers, or useful for controlling water balance (e.g., in diabetes insipidus and polyuria), hearing regulation, controlling sodium ion excretion, ameliorating brain function, comprising an amount of a compound of formula (I), or a pharmaceutically acceptable salt thereof that is effective in treating such disorder or condition in a mammal including a human, and a pharmaceutically acceptable carrier.

This invention also relates to a method of treating a disorder or condition, or anesthetizing a mammal including a human, where the treatment or anesthetization of which can be effected or facilitated by activating ORL1-receptor in a mammal, including a human, comprising administering to a mammal in need of such treatment an effective amount of a compound of formula (I) or a pharmaceutically acceptable salt thereof.

More specifically, this invention relates to a method for treating a disorder or condition in a mammal including a human, where the disorder or condition is selected from the group consisting of inflammatory diseases, inflammation-related hyperalgesia, eating disorder (e.g., in obesity), arterial blood pressure disorders (i.e., hypertension or hypotension), tolerance to narcotic analgesics such as morphine, dependence on narcotic analgesics such as morphine, anxiety, stress disorders, psychic trauma, schizophrenia, Parkinson's disease, chorea, depressant, Alzheimer's disease, dementias, epilepsy and convulsions, or for anesthetizing a mammal including a human, or for alleviating pain (e.g., acute, chronic and neuropathic pain), producing a neuroprotective effect, enhancing analgesic, controlling water balance (e.g., in diabetes insipidus and polyuria), hearing regulation, controlling sodium ion excretion or ameliorating brain function in a mammal including a human, comprising administering to said mammal an effective amount of a compound of formula (1) or a pharmaceutically acceptable salt thereof and a pharmaceutically acceptable carrier.

Among the foregoing processes of this invention for preparing a compound of formula (I), preferred are those processes comprising in step (a), the coupling reaction is carried out in the presence of a base in a reaction inert solvent at a temperature in the range from room temperature to the reflux temperature of the reaction mixture for from 0.5 to 48 hours;

in step (b), the reduction is carried out in the presence of a reducing reagent in a reaction inert solvent at a temperature in the range from room temperature to the reflux temperature of the reaction mixture for from 0.5 to 48 hours, and the hydrogenation is carried out in the presence of a metal catalyst at a temperature in the range from 0° to 100° C. under hydrogen atmosphere in a reaction inert solvent for from 0.5 to 48 hours; and in step (c), benzimidazole formation is carried out with a coupling reagent selected from the group consisting of carboxylic acids, amino carboxylic acids, acid anhydrides, formamides, alkylcarbonyl halides, aryl carbonyl halides, aryl alkyl carbonyl halides, heteroaryl carboxylic acids, carbon disulfides, cyanogen halides, cyanamide and trialkyl orthoformates, in the presence of a peptide coupling reagent in a reaction inert solvent at a temperature in the range from 0° C. to the reflux temperature of the reaction mixture for from 1 minutes to 120 hours.

More preferred process of this invention for preparing a compound of formula (I) comprises in step (a), the base is selected from the group consisting of $K_2CO_3$, and amines;

in step (b), the reducing reagent is selected from the group consisting of $SnCl_2$, zinc catalysts and iron catalysts, and the metal catalyst used in the hydrogenation is selected from the group consisting of Raney nickel catalysts, palladium catalysts and platinum catalysts; and in step (c), the peptide coupling reagent used in the benzimidazole formation is selected from the group consisting of dicyclohexylcarbodiimide (DCC), diisopropylcarbodiimide (DIPC), 1-ethyl-3-(3-dimethylaminopropyl)carbodiimide (WSC), benzotriazole-1-yloxy-tris(dimethylamino) phosphonium hexafluorophosphate (BOP), and diphenylphosphorylazide (DPPA).

Preferred intermediate compounds of formula (IX) are those, wherein

R is selected from the group consisting of $(C_3-C_{11})$ cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four-to six ring atoms wherein one to two ring atoms are independently selected from heteroatoms, and aryl, or aromatic or non-aromatic heterocyclic wherein each of said aforementioned groups is optionally substituted with up to three substituents independently selected from halo, $(C_1-C_4)$ alkyl , halo $(C_1-C_4)$alkyl, $(C_1-C_4)$alkoxy, —CHO, cyano, $(C_1-C_4)$alkyl-CO—, $NH_2$—CO—, $NH_2$–$CH_2$—, amino, $(C_1-C_4)$alkyl-NH—, di($(C_1-C_4)$ alkyl)-N—, $(C_1-C_4)$alkyl-CO—NH— and $(C_1-C_4)$ alkyl-NH—CO—; and $Z^1$, $Z^2$, $Z^3$ and $Z^4$ are independently selected from the group consisting of hydrogen and halo.

More preferred intermediate compounds of formula (IX) are those wherein

R is selected from the group consisting of $(C_3-C_{11})$ cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, thiinyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, $(C_1-C_4)$ alkyl, halo $(C_1-C_4)$alkyl and $(C_1-C_4)$alkoxy; and $Z^1$ and $Z^2$ are independently selected from the group consisting of hydrogen and halo; and $Z^3$ and $Z^4$ are both hydrogen.

More preferred intermediate compounds of formula (IX) are those compounds wherein R is $(C_6-C_{10})$cycloalkyl;

A is attached to the carbon atom of R with which R is attached to the nitrogen atom of the piperidine ring, and selected from the group consisting of $(C_1-C_7)$alkyl and $(C_2-C5)$alkenyl, phenyl and naphthyl; and $Z^1$, $Z^2$, $Z^3$ and $Z^4$ are all hydrogen.

Among the foregoing intermediate compounds of formula (IX), particularly preferred are those compounds wherein R is $(C_7-C_9)$cycloalkyl;

A is attached to the carbon atom of R with which R is attached to the nitrogen atom of the piperidine ring, and selected from the group consisting of methyl and phenyl; and $Z^1$, $Z^2$, $Z^3$ and $Z^4$ are all hydrogen.

Preferred intermediate compounds of formula (X) are those wherein

R is selected from the group consisting of $(C_3-C_{11})$ cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four to six ring atoms wherein one to two ring atoms are independently selected from heteroatoms, and aryl, or aromatic or non-aromatic heterocyclic wherein each of said aforementioned groups is optionally substituted with up to three substituents independently selected from halo, $(C_1-C_4)$ alkyl, halo $(C_1-C_4)$alkyl, $(C_1-C_4)$alkoxy, —CHO, cyano, $(C_1-C_4)$alkyl-CO—, $NH_2$–CO—, $NH_2$–$CH_2$—, amino, $(C_1-C_4)$alkyl-NH—, di($(C_1-C_4)$alkyl)-N—, $(C_1-C_4)$alkyl-CO—NH— and $(C_1-C_4)$alkyl-NH— CO—; and $Z^1$, $Z^2$, $Z^3$ and $Z^4$ are independently selected from the group consisting of hydrogen and halo.

More preferred intermediate compounds of the formula (X) are those wherein

R is selected from the group consisting of $(C_3-C_{11})$ cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, ($C_2$–$C_5$)alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, thiinyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, ($C_1$–$C_4$) alkyl, halo ($C_1$–$C_4$)alkyl and ($C_1$–$C_4$)alkoxy; and $Z^1$ and $Z^2$ are independently selected from the group consisting of hydrogen and halo; and $Z^3$ and $Z^4$ are both hydrogen.

Among the foregoing intermediate compounds of formula (X), more preferred are those compounds wherein R is ($C_6$–$C_{10}$)cycloalkyl;

A is attached to the carbon atom of R with which R is attached to the nitrogen atom of the piperidine ring, and selected from the group consisting of ($C_1$–$C_7$)alkyl and ($C_2$–$C_5$)alkenyl, phenyl and naphthyl; and $Z^1$, $Z^2$, $Z^3$ and $Z^4$ are all hydrogen.

Particularly preferred intermediate compounds of formula (X) are those compounds wherein R is ($C_7$–$C_9$)cycloalkyl;

A is attached to the carbon atom of R with which R is attached to the nitrogen atom of the piperidine ring, and selected from the group consisting of methyl and phenyl; and $Z^1$, $Z^2$, $Z^3$ and $Z^4$ are all hydrogen.

General Synthesis

The following reaction Schemes illustrate the preparation of the compounds of the present invention. Unless otherwise indicated, R, A, Y, and $Z^1$ to $Z^4$ in the reaction Schemes and discussion that follow are defined above.

The ORL1 agonist compounds of Formula (I) of this invention may be prepared according to the following methods.

In the reaction schemes appearing below, a substituent represented as A of compounds of the formulae (V), (Ia), (VI), (VII), (IX), (X), (XIII), (XIV) and (XVI) is attached to the carbon atom in R attached to the nitrogen atom of the piperidine ring. In compounds of formulae (IV), (XII) and (XVIII), the cyano group is also attached to the carbon atom in R which is attached to the nitrogen atom in the piperidine ring. In compounds of formula (XIV), A is attached to the same carbon atom of R where the amino group is attached.

In a desired reaction step of the processes described hereafter, amino protections and removal of the amino protecting groups with reactants and reagents used may be carried out according to known procedures such as those described in Protective Groups in Organic Synthesis edited by T. W. Greene et al. (John Wiely & Sons, 1991). Typical amino protecting groups include benzyl, $C_2H_5CO_2$— and t-But$CO_2$— represented as t-Boc or Boc.

Scheme 1 illustrates an embodiment of preparation process for a compound of formula (I) wherein Y is a leaving group, represented by L in the scheme, such as halo hereinafter represented by Formula (Ia).

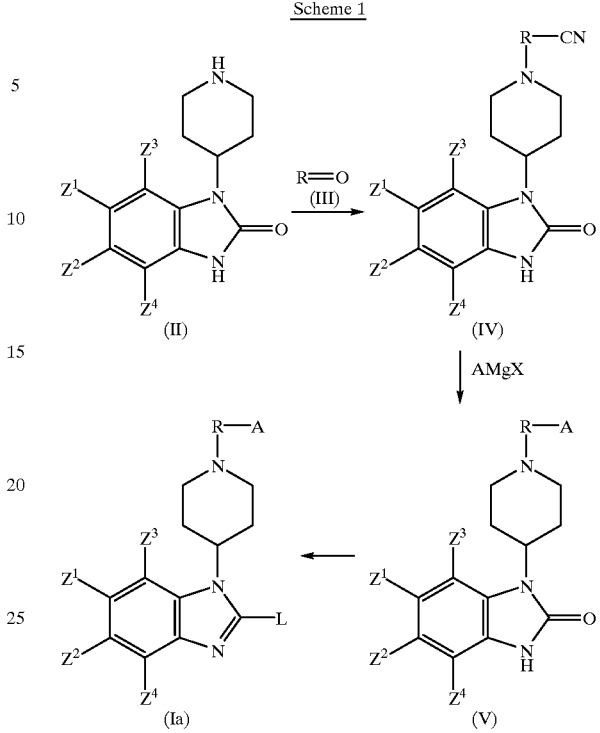

As shown in Scheme 1, a compound of formula (Ia), wherein L represents a leaving group such as halo, may be obtained from a known benzimidazolylpiperidine compound of formula (II) via intermediate compounds of formulae (IV) and (V).

First, a compound formula (II) may be subjected to the Strecker synthesis with the stoichiometric amount of a cyclic ketone compound of formula (III) to give the compound of formula (IV). Second, the resulting compound of formula (IV) may be reacted with a Grignard reagent of formula AMgX (X is halo) to give the compound of formula (V). Then, the compound of formula (V) may be reacted with a suitable nucleophilic reagent to yield the compound of formula (Ia) by introducing a leaving group to the compound of formula (V) in the presence or absence of a catalyst.

The Strecker synthesis may be carried out using a suitable cyanating agent according to known procedures reported by A. Kalir, et al., (J. Med. Chem. Vol. 12, p. 473, 1969). Suitable cyanating agents include cyanide such as potassium cyanide (KCN). This reaction may be carried out at pH in the range of about 3 to 11 at about 0° C. such as in ice-cool water.

The reaction of the compound of formula (IV) with a Grignard reagent may be carried out under anhydrous condition according to known procedures (e.g., O. A. Al-Deeb, Arzneim.-Forsch./Drug Res., Vol. 44 (11), Nr. 10, 1994). More specifically, this reaction may be carried out in a suitable solvent such as tetrahydrofuran (THF) or ether, at from 0° C. to the reflux temperature of the reaction mixture for from about 30 minutes to about 48 hours. Preferably, the Grignard reagent may be added to the reaction mixture at about 0° C. and the reaction mixture may be allowed to warm to room temperature for further reaction.

The compound of formula (V) thus obtained may be refluxed with a suitable nucleophilic reagent to give the compound of formula (Ia). In case of L is Cl, a suitable chlorinating reagent is, for example, phosphoryl chloride.

This reaction may be carried out under conditions for example reported by R. Iemura et al. *J Med Chem.* Vol. 29, pp. 1178–1183, 1986.

A compound of formula (Ia) wherein L is halo (i.e., a compound of formula (I) wherein Y is halo) may be subjected to a reaction with a nucleophilic reagent under known reaction conditions to give a compound of formula (I) wherein Y is other than halo. The nucleophilic reagents include amine and imine compounds such as mono-or di-alkylamines, cycloalkyl amines, alkenyl amines and aromatic amines such as aniline, nitrogen containing heterocyclic compounds such as aminoazetidine, pyrrolidine, piperidine, piperazine, morpholine and azabicyclo compounds, alkoxides and thioalkoxides such as sodium alkoxide and sodium thioalkoxide, alcohols including cyclic alcohols and diols, and the like. This reaction may be carried out in a reaction inert solvent at from about 0° to about 200° C. (preferably from 0° to 150° C.) for about 1 to about 24 hours (preferably from about 2 to about 12 hours). Suitable reaction inert solvents include alcohols such as methanol, ethanol, isopropyl alcohol, tert-butyl alcohol, and N,N-dimethylformamide (DMF) and the like. If appropriate, this reaction may be carried out in a suitable reaction chamber such as an autoclave.

A substitution reaction of a compound of formula (I) wherein Y is Cl with an imide may be carried out using according to the procedures reported by C. H. Senanayake, et al., *Tetrahedron Lett.*, Vol. 38, pp. 5607–5610, 1997. In the report, Pd-catalyst is used in the presence of a base in toluene with heating.

In addition, a compound of formula (I) wherein Y is attached to the benzoimidazole ring through S may be oxidized to a corresponding sulfonyl compound under conventional oxidation-conditions with thioethers using an oxidizing reagents such as potassium permanganate.

A compound of formula (II) may be prepared by carbonylation of a diamine compound of formula (X).

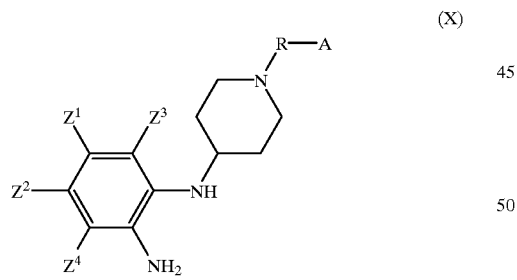

The carbonylation may be carried out by reacting a compound of formula (X) with a suitable carbonylating agent such as carbonyldiimidazole, trichloromethyl chloroformate, triphosgene or urea, in a reaction inert solvent such as THF, benzene, toluene or chloroform, at the temperature in the range of from about 0° to about 120° C. for from about 0.5 to about 24 hours. The reaction may be conducted according to the procedures described in WO 98/54168.

Compounds of the formula (I), wherein Y is other than halo may be also prepared by the methods illustrated in Scheme 2.

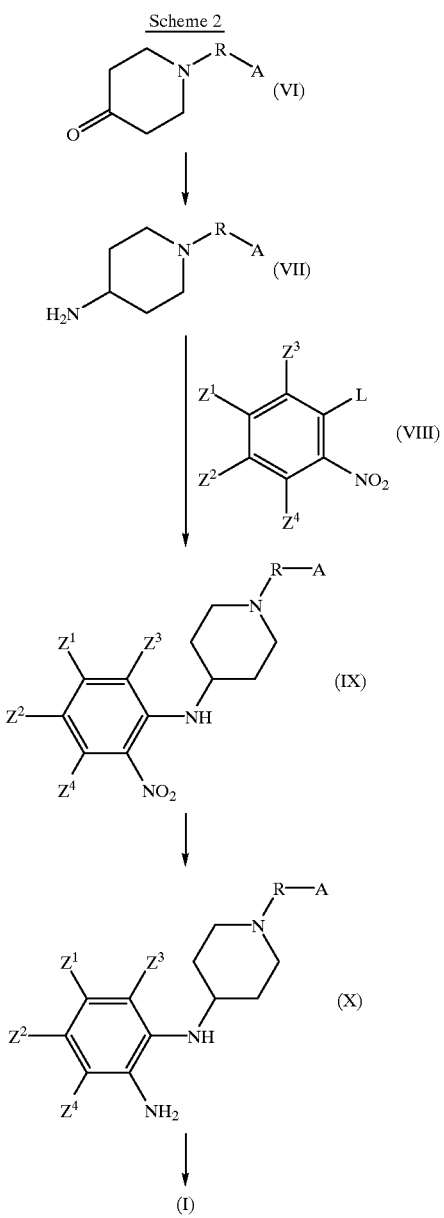

Scheme 2

As shown in Scheme 2, compounds of formula (I), wherein Y is other than halo may also be prepared through the process comprising:

(a) reductive amination of a piperidine-4-one compound of formula (VI) to give the 4-aminopiperidine compound of formula (VII);

(b) coupling reaction of the compound of formula (VII) with a nitrobenzene compound of formula (VIII) wherein L is a leaving group such as halo to give the nitroaniline compound of formula (IX);

(c) reduction of the resulting nitroaniline compound of formula (IX) to give the diamine compound of formula (X); and (d) benzimidazole ring formation with the compound of formula (X) to give the compound of formula (I)

Each reaction step is described more specifically in the following.

(a) The reductive amination may be conducted by an oximation of the piperidine 4-one compound of formula (VI) followed by reduction. Both of the reactions may be conducted under conditions for oximation of carbonyl compounds known to those skilled in the art. For example, the oximation may be carried out by reacting the piperidine compound with hydroxylamine in the presence or absence of a base in a reaction inert solvent such as alcohol at about room temperature for about 0.5 to 48 hours. The resulting oxime compound may be extracted and subjected to reduction under known conditions to give the amine compound of formula (VII). The reduction may be carried out in the presence of a reducing reagent such as lithium aluminum hydride in a reaction inert solvent such as THF at about 0° C. to room temperature for from about 0.5 to 48 hours.

(b)–(c) Steps (b) and (c) may be carried out under conditions known to those skilled in the art (e.g., B. de Costa et al., *J. Chem. Soc. Perkin. Trans.*, Vol. 1, pp. 1671–1680, 1992 and N. A. Meanwell et al., *Bioorganic& Medicinal Chemistry Letters*, Vol. 6, No. 14, pp. 1641–1646, 1996). For example, coupling reaction (b) may be carried out in the presence of a base such as $K_2CO_3$ and triethylamine ($NEt_3$) in a reaction inert solvent such as acetonitrile under reflux for about 0.5 to 48 hours. Then, the resulting compound of formula (IX) may be extracted and subjected to reduction to give the compound of formula (X). The reduction may be carried out in the presence of a suitable reducing reagent such as $SnCl_2$, zinc catalysts and iron catalysts in a reaction inert solvent such as ethanol at a temperature in the range from room temperature to the reflux temperature of the reaction mixture (preferably under reflux) for from about 0.5 to about 48 hours. The reduction may also be carried out under known hydrogenation conditions such as in the presence of a metal catalyst such as Raney nickel catalysts, palladium catalysts and platinum catalysts at a temperature in the range from about 0° to 100° C. (preferably at about room temperature) under hydrogen atmosphere in a reaction inert solvent such as ethanol or THF for from about 0.5 hours to 2 days.

(d) A compound of formula (X) may be cyclized to form a benzimidazole ring by reaction with an appropriate cyclizing reagent to give the compound (I) in a reaction inert solvent in the presence or absence of a coupling reagent. Suitable cyclizing reagents include a carboxylic acid, an amino carboxylic acid, an acid anhydride (e.g., acetic anhydride, isobutyric anhydride, benzoic anhydride, isonicotinic anhydride and the like) a formamidine (e.g., formnamidine alkylate such as formamidine acetate), an alkyl carbonyl halide (e.g., a cycloalkyl carbonyl halide), an aryl or an aryl alkyl carbonyl halide (e.g., phenylacethyl halide), an heteroaryl carboxylic acid (e.g., a piperidinyl carboxylic acid compound), carbon disulfide, cyanogen halide (e.g., cyanogen bromide), cyanamide, trialkyl orthoformate (e.g., triethyl orthoformate), and the like. Suitable solvents tetrahydrofuran (THF), xylene, ethoxyethanol and the like. Suitable coupling reagents are those typically used in peptide synthesis including dicyclohexylcarbodiimide (DCC), diisopropylcarbodiimide (DIPC), 1-ethyl-3-(3-dimethylaminopropyl) carbodiimide (WSC), benzotriazole-1-yloxy-tris (dimethylamino)phosphonium hexafluorophosphate (BOP), diphenylphosphorylazide (DPPA) and the like. This reaction may be carried out at from about 0° C. to the reflux temperature of the reaction mixture, preferably from about room temperature to the reflux temperature for about 1 minute to about 120 hours, preferably for from about 10 minutes to about 72 hours. An embodiment of the 2-aminobenzimidazole ring formation is also reported by N. A. Meanwell et al., *Bioorganic & Medicinal Chemistry Letters*, Vol. 6, No. 14, pp. 1641–1646, 1996. These reactions are also reported by A.

F. Pozharskii et al., Russ. Chem. Rev. (English Translation), Vol. 35. P. 122-,1996.

Alternatively, a compound of formula (X) may be subjected to a coupling reaction with an isothiocyanate compound and a subsequent desulfurization under known conditions to give a compound of formula (I) wherein Y is connected to the benzimidazole ring through NH. For example, the first coupling reaction may be carried out in a reaction inert solvent such as an alcohol (e.g., ethanol) at from about room temperature to 100° C. from 30 minutes to 48 hours under stirring. The desulfurization may be carried out in the presence of an alkyl halide under reflux for from about 30 minutes to 48 hours.

A compound of formula (I) wherein Y is connected to the benzimidazole ring through carbonyl (C=O) may be prepared according to known procedures. For example, a compound of formula (I) wherein Y is hydrogen may be reacted with a lithiation reagent such as n-BuLi under known conditions followed by reaction with an appropriate amide compound such as an N,N-alkylalkoxy amide under known conditions. The former reaction may be carried out at about −78° C. in a reaction inert solvent such as THF for from about 30 minutes to 48 hours. The latter reaction may be carried out at about −78° C. to ambient temperature in THF for about 30 minutes to 24 hours according to known procedures reported by G. Bitan et al.,*J. Chem. Soc., Perkin. Trans.* Vol. 1, pp. 1501–1510, 1997.

Further, compounds of formula (I) thus obtained may be modified in the Y- group described as follow.

A compound of formula (I) wherein Y has an amino or an imine group (e.g., piperidinyl, piperazinyl and the like) at its terminal position may be further reacted with a desired reactant under known conditions to modify the Y. For example, these amine or imine compounds may be reacted with an alkylcarbonyl halide at about room temperature in a basic solvent to give an amide compound. The amine or imine compounds may be reacted with an amino acid, or an amino acid sulfone or sulfoxide in the presence or absence of a coupling reagent known to those skilled in the art in peptide synthesis. Suitable coupling reagents include WSC and the like. The amino or imino compound may be coupled with an amino acid, an amino acid sulfone or sulfoxide, or a phthalimido alkyl sulfonyl halide under conventional amide formation conditions in the presence of a coupling reagent in a reaction inert solvent such as acetonitrile at about room temperature. These amino acids include isoleucine, alanine, methionine, proline, phenylalanine, valine, and the like. Suitable coupling reagents are those typically used in peptide synthesis including WSC, dicyclohexylcarbodiimide (DCC), N,N'-carbonyldiimidazole (CDI), $POCl_3$, $TiCl_4$, $SO_2ClF$, benzotriazol-1-yl diethyl phosphate, $Ti(Obu)_4$, molecular sieves, N,N,N',N'-tetramethyl(succinimido)uronium tetrafluoroborate, CBMIT, Lawesson's reagent, chlorosulfonyl isocyanate, $P_2I_4$, pyridinium salts-$Bu_3N$, and a mixture of $Bu_3P$ and PhCNO. The amine or imine compounds may be also reacted with a guanidine compound under known conditions. A suitable reaction condition comprises reaction with an amino-protected guanidine compound in a reaction inert solvent such as THF at about room temperature (see M. S. Bematowicz, et al., *Tetrahedron Lett.*, Vol. 34, Intermediate compounds (VI) may be prepared by the methods illustrated in Scheme 3.

Route 3 illustrates a preparation procedure for a compound of formula (VI) from a known 4-peperidone ethylene ketal (XVII). This preparation comprises (a) condensation of a compound of formula (XVII) with a ketone compound of

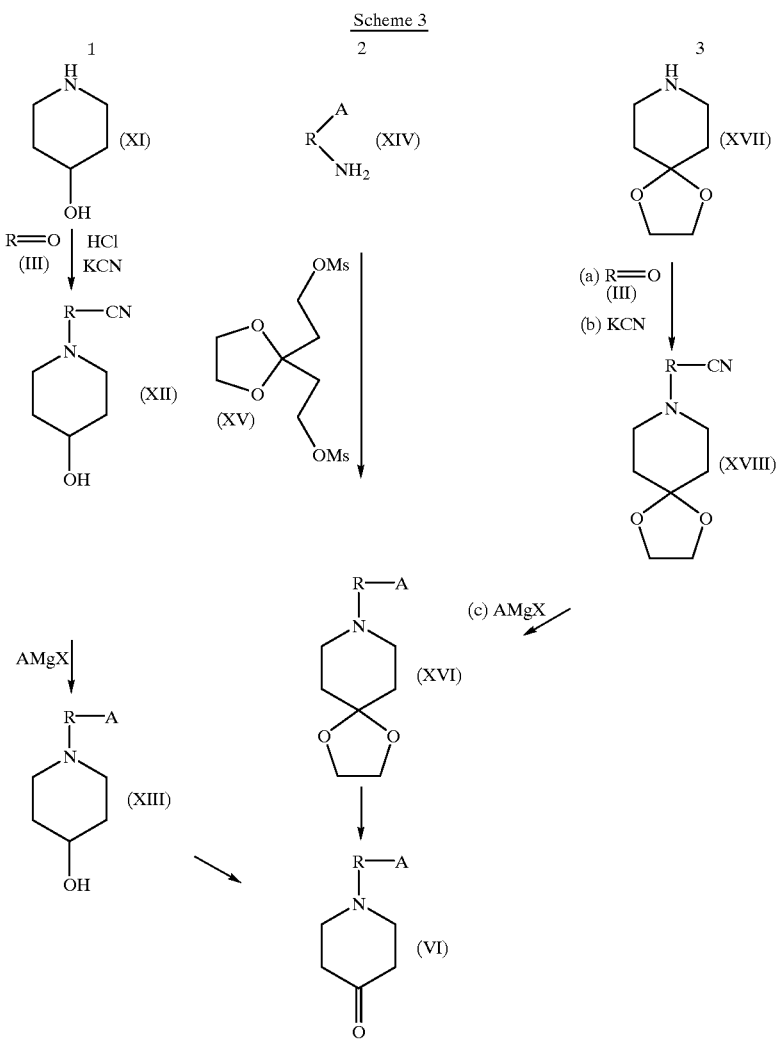

formula (III), (b) cyanation, (c) reaction of the compound of formula (XVIII) with a Grignard reagent and (d) deprotection of the compound of formula (XVI). These reactions may be carried out under the similar conditions to those described in Scheme 1.

The starting amine compounds of formula (XIV) may be readily prepared by known methods for a skilled person (e.g., J. Weinstock, et al., OS IV 910, E. J. Cone, et al, *J. Med. Chem.*, Vol. 24, pp. 1429–1432, 1981, and Ritter Reaction described in *Org. React.* Vol. 17, pp. 313–325, 1969).

In addition, compounds of formula (I) wherein Y is substituted or non-substituted alkylcarbonyl may be prepared using a method similar to that reported in P. D. Edwards,-et a., *J. Med. Chem.*, Vol. 38, pp. 76–85, 1995. For example, 2-lithium-benzimidazole, prepared by addition of n-buthyl lithium to benzimidazole in tetrahydrofuran, may be acylated with 3-t-butoxycarbonylamino-N-metoxy-N-methylpropionamide to give the acylated product. Then protecting group (e.g., Boc) can be removed by treatment with hydrochloric acid in methanol.

Route 1 in Scheme 3 illustrates a preparation procedures for a compound of formula (VI) from 4-piperidinol of formula (XI) according to the procedures reported by A. Kalir et al., *J. Med. Chem.*, Vol. 12, pp. 473–477, May 1996. First, a compound of formula (XI) may be condensed with a compound of formula (III) and cyanated to give the compound of formula (XII). Second, the obtained compound of formula (XII) may be reacted with a Grignard reagent AMgX wherein X is halo to give the compound of formula (XIII). Then, resulting compound of formula (XIII) may be oxidized to give the compound of formula (VI). The condensation and cyanation may be carried out using 4-piperidinol HCl salt in water at about room temperature.

Route 2 illustrates a preparation procedure for a compound of formula (VI) from a starting amine (XIV) comprising condensation of a compound of formula (XIV) with 3,3-ethylenedioxypentane-1,5-diol dimethanesulfonate (XV) followed by deprotection. These reactions may be carried out under known conditions (e.g., B. de Costa et al., *J. Chem. Soc. Perkin. Trans.*, Vol. 1, p. 1671, 1992 and R. L. McQuinm et al., *J. Med. Chem.* Vol. 24, pp. 1429–1432, 1981).

The starting materials (III), (XI), (XIV), (XVII) and the other reactants are known or commercially available compounds, or may be prepared according to known procedures for a person skilled in the art.

In the each reaction described above, unless indicated otherwise, the reaction pressure is not critical. Generally, the reactions will be conducted at a pressure of about one to about three atmospheres, preferably at ambient pressure (about one atmosphere).

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, 35S, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deutrium, i.e., $^2H$, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labelled reagent.

The compounds of Formula (I) of this invention are basic, therefore they will form acid-addition salts. All such salts are within the scope of this invention. However, it is necessary to use an acid addition salts which, is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, ethanesulfonate, benzenesulfonate, p-toluenesulfonate, oxalate and pamoate (1,1'-methylene-bis-(2-hydroxy-3-naphtoate)) salts.

The compounds of formula (I) of this invention may contain one or more asymmetric centers and thus they can be exist as diastereomers. The invention includes both mixtures thereof and the separated individual diastereomers.

In addition, when the compounds of this invention form hydrates or solvates they are also within the scope of this invention.

The compounds of Formula (I) have been found to possess selective affinity for ORL1-receptors and ORL-1 receptor agonist activity. Thus, these compounds are useful as an analgesic, anti-inflammatory, diuretic, anesthetic, neuroprotective, anti-hypertensive and anti-anxiety agent, and the like, in mammalian subjects, especially humans in need of such agents. The affinity, agonist activities and analgesic activity can be demonstrated by the following tests respectively.

Selective Affinity for ORL1-receptors
ORL1-receptor Affinity:

The ORL1 receptor binding affinity of the compounds of this invention are determined by the following procedures. Human ORL1 receptor transfected HEK-293 cell membranes and wheat-germ agglutinin coated SPA beads are combined with 0.4 nM[$^3H$]nociceptin and unlabeled test compounds in 200 μl of 50 mM Hepes buffer pH7.4 containing 10 mM $MgCl_2$ and 1 mM EDTA. This mixture is incubated at room temperature (abbreviated as rt) for 30 min to 60 min. Non specific binding is determined by the addition of 1 μM nociceptin. Radioactivity is counted by Wallac 1450 MicroBeta.

μ-preceptor Affinity:

The mu (μ) opioid receptor binding affinity of the compounds of this invention are determined by the following procedures. Human-mu opioid receptor transfected CHO-K1 cell membranes and wheat-germ agglutinin coated SPA beads are combined with 1.0 nM[$^3H$]DAMGO and unlabeled test compounds in 200 μl of 5 nM Hepes buffer pH7.4 containing 10 mM $MgCl_2$ and 1 mM EDTA. This mixture is incubated at rt for 30 min to 60 min. Non specific binding is determined by the addition of 1 μM DAMGO. Radioactivity was counted by Wallac 1450 MicroBeta.

κ-receptor Affinity:

The kappa (κ) opioid receptor binding affinity of the compounds of this invention are determined by the following procedures. Human kappa-opioid receptor transfected CHO-K1 cell membranes and wheat-germ agglutinin coated SPA beads are combined with 0.5 nM[$^3H$]CI-977 and unlabeled test compounds in 200 μl of 50 mM Hepes buffer pH7.4 containing 10 MM $MgCl_2$ and 1 mM EDTA. This mixture is incubated at rt for 30 min to 60 min. Non specific binding is determined by the addition of 1 μM CI-977. Radio activity is counted by Wallac 1450 MicroBeta.

δ-receptor Affinity:

The delta (δ) opioid receptor binding affinity of the compounds of this invention are determined by the following procedures. Human delta opioid receptor transfected CHO-K1 cell membranes and wheat-germ agglutinin coated SPA beads are combined with 2.0 nM[$^3H$]DPDPE and unlabeled test compounds in 200 μl of 50 mM Hepes buffer pH7.4 containing 10 mM $MgCl_2$ and 1 mM EDTA. The assay is incubated at room temperature for 30 min to 60 min. Non specific binding are determined by the addition of 1 μM of each non-labeled ligands. Radioactivity is counted by Wallac 1450 MicroBeta.

Each percent non specific binding thus obtained is graphed as a function of compound concentration. A sigmoidal curve is used to determine 50% bindings (i.e., $IC_{50}$ values).

In this testing, most of the compounds prepared in the working examples appearing hereafter demonstrated higher affinity for ORL1-receptors than for mu-receptors.

$IC_{50}$ (ORL1-receptors) $nM/IC_{50}$ (mu-receptors) nM<1.0.

Functional Assay:

The functional activity of the compounds of this invention in each opioid receptor can be determined in 35S-GTPγS binding system according to the procedures reported by L. J. Sim, R. Xiao and S. Childers *Neuroreort* Vol. 7, pp. 729–733, 1996. Each human ORL1-, mu-, kappa- and delta-receptor transfected CHO-K1 or HEK cell membranes are used. The membranes are suspended in ice-cold 20 mM HEPES buffer pH 7.4, containing 100 mM NaCl, 10 mM $MgCl_2$ and 1 mM EDTA. 0.17 mg/ml of Dithiothreitol (DTT) is added to this buffer prior to use. Membranes are incubated at 25° C. for 30 minutes with the appropriate concentration of test compounds in the presence of 5 µM GDP, 0.4 nM of 35S-GTPγS and Wheat-germ agglutinin (WGA) coated SPA bead (1.5 mg) in a 0.2 ml total volume. Basal binding is assessed in the absence of agonist, and non-specific binding is determined with 10 µM GTPγS. Radio activity is counted by Wallac 1450 MicroBeta. Some compounds of this invention prepared in Examples exhibited good ORL1 agonists activity in this assay.

Analgesic Tests:

Tail Flick Test:

Male ICR mice, 4 weeks old and weighing 19–25 g, are used. The training sessions are performed until mice can flick their tails within 4.0 sec by using Analgesia Meter MK-330A (Muromachi Kikai, Japan). Selected mice are used in this experiment. The latency time is recorded twice at 0.5, 1.0, and 2.0 h after administration of the compound. The intensity of the beam is set to 80. Cut-off time is set to 8.0 sec. A compound of this invention is subcutaneously administered 30 min before the test. The $ED_{50}$ value is defined as the dose of a compound tested which halves the tail flicking observed in a control group.

Acetic Acid Writhing Test:

Male ICR mice, 4 weeks old and weighing 21–26 g, are used. They are fasted the day before use. Acetic acid is diluted with saline to the concentration of 0.7%(v/v) and injected intraperitoneally (0.2 ml/10 g of body weight) to mice with a 26 gauge needle. A compound of this invention is dissolved in 0.1% methyl cellulose(MC)-saline and subcutaneously administered to mice 0.5 h before acetic acid injection. After the acetic acid injection, each animal is placed in a 1L beaker and recorded by a video tape recorder. Number of writhing is counted from 5 to 15 min after acetic acid injection. The $ED_{50}$ value, defined as the dose of the compounds tested which halves the writhing is observed in the control group. Some compounds of this invention demonstrated good analgesic activity in this test.

Formalin Licking Test:

Male SD rats (80–100 g) are injected subcutaneously with a test compound dissolved in 0.1% methyl cellulose(MC)-saline or vehicle. After 30 min, 50 µl of a 2% formalin are injected into a hind paw. The number of licking the injected paw per observation period is measured from 15 to 30 min. after the injection of formalin and expressed as % inhibition compared to the respective vehicle group. This testing method is described in, for example, (1) R. L. Follenfant, et.al., Br. J. Pharmacol. 93, 85–92 (1988); (2) H. Rogers, et.al., Br. J. Pharmacol. 106, 783–789 (1992); and (3) H. Wheeler-Aceto, et al., Psychopharmacology, 104, 35–44 (1991).

The compounds of Formula (I) of this invention can be administered by conventional pharmaceutical practice via either the oral, parenteral or topical routes to mammals, for the treatment of the indicated diseases. For administration to human patient by either route, the dosage is in the range of about 0.01 mg/kg to about 3000 mg/kg body weight of the patient per day, preferably about 0.01 mg/kg to about 1000 mg/kg body weight per day administered singly or as a divided dose. However, variations will necessarily occur depending upon the weight and condition of the subject being treated, compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifing agents, stabilizers, buffering agents, tonicity agents, preservatives, flavorating agents, aromatics, coloring agents and the like.

For example, the tablets can contain various excipients such as starch, lactose, glucose, microcrystalline cellulose, calcium sulfate, calcium carbonate, talc, titanium oxide and the like, coating agents such as gelatin, hydroxypropylcellulose and the like, binding agents such as gelatin, gum arabic, methylcellulose and the like, and the disintegrating agents such as starch, agar, gelatine, sodium hydrogencarbonate and the like. Additionally, lubricating agents such as magnesium stearate and talc are often very useful for tabletting purposes. Solid compositions of a similar type may also be employed as fillers in gelatine capsules; preferred materials in this connection also include lactose as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. The edible oil such as cottonseed oil, sesame oil, coconut oil or peanut oil can be employed for the edible oil solutions. The oil solutions are suitable for intra-particular, intramuscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparation. However, it should be understood that the invention is not limited to the specific details of these examples and preparations. Melting points were taken with a Buchi micro melting point apparatus and is not corrected. Infrared Ray absorption spectra (IR) were measured by a Shimadzu infrared spectrometer (IR470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

EXAMPLES AND PREPARATIONS

Example 1
2-Chloro-1-[1-(1-phenylcycloheptyl)-4-piperidinyl]-1H-benzimidazole

A mixture of 4-(2-keto-1-benzimidazolinyl)piperidine (5.10 g, 23.5 mmol) and HCl solution in MeOH (20 ml) was stirred at room temperature for 10 min. After evaporation of the solvent, the residue was triturated in Et$_2$O to give HCl salt as off-white powder. To this HCl salt was added cycloheptanone (3.33 ml, 28.2 mmol) followed by addition of aqueous solution of KCN (1.92 g, 29.5 mmol) in water (7 ml) at room temperature. After 18 h stirring, the resulting solid was collected by filtration, washed with water, and dried in vacuo to give 6.81 g (85.7%) of nitrile derivative as white powder. To a solution of this nitrile derivative (5.12 g, 15.1 mmol) in THF (40 ml) was added a solution of phenylmagnesium bromide in Et$_2$O (3.0 M solution, 25 ml) at 0° C. Then the reaction mixture was stirred at room temperature for 18 h. Aqueous NH$_4$Cl solution was added to the reaction mixture and the resulting solid appeared was collected by filtration, washed with water and Et$_2$O, and dried in vacuo at 70° C. to give 4.88 g (82.8%) of 1-[1-(1-phenylcycloheptyl)-4-piperidinyl]-1,3-dihydro-2H-1,3-benzimidazol-2-one as white powder. A mixture of 1-[1-(1-phenylcycloheptyl)-4-piperidinyl]-1,3-dihydro-2H-1,3-benzimidazol-2-one (2.316 g, 5.95 mmol) and phosphoryl chloride (15 ml, 165.5 mmol) was heated to reflux for 1.5 h. After cooling down to room temperature, the reaction mixture was poured into ice cooled 25% ammonia solution and extracted with CH$_2$Cl$_2$. The extracts combined were washed with brine, dried (Na$_2$SO$_4$), filtered, and concentrated. The residue was purified by column chromatography (silica gel: 200 g, hexane/ethyl acetate: 4/1) to give 1.42 g(58.7%) of colorless amorphous solid.

$^1$H NMR (270 MHz, CDCl$_3$) δ 7.70–7.63 (1H, m), 7.61–7.49 (3H, m), 7.38–7.31 (2H, m), 7.30–7.20 (3H, m), 4.40–4.29 (1H, m), 3.05–3.00 (2H, m), 2.52–2.22 (4H, m), 2.13–2.09 (4H, m), 1.81–1.72 (5H, m), 1.60–1.49 (5H, m).

This free amine was converted to HCl salt by treating the obtained compound with HCl solution in MeOH. Evaporation of the solvent afforded solid, mp 153–156° C.

MS(ESI positive) m/z: 408(M+H)$^+$. Anal. Calcd for C$_{25}$H$_{30}$N$_3$Cl.HCl.2.1H$_2$O: C,62.26; H, 7.36; N, 8.71. Found: C, 62.06; H, 7.26; N, 8.5 1.

Example 2
N-Methyl-1-[1-(1-phenylcycloheptyl)-4-piperidinyl]-1-H-benzimidazol-2-amine A solution of 2-chloro-1-[1-(1-phenylcycloheptyl)-4-piperidinyl]benzimidazole (Example 1, 69.3 mg, 0.17 mmol) in 40% MeNH$_2$ solution in MeOH (5 ml) was stirred in autoclave at 110° C. for 6 h. After cooling down to room temperature, the solvent was evaporated and the residue was purified by preparative TLC (0.5 mm plate×3, CH$_2$Cl$_2$/MeOH:10/1) to give 56.9 mg(83%) of title compound as pale brown amorphous solid.

MS m/z(EI): 402(M$^+$), 345, 317, 230, 173, 147, 91. $^1$H NMR (270 MHz, CDCl$_3$) δ 7.52–7.46 (3H, m), 7.38–7.18 (4H, m), 7.12–6.98 (2H, m,), 4.16–4.06 (1H, m), 3.80–3.70 (1H, m), 3.14 (3H, d, J=4.8 Hz), 3.05–2.96 (2H, m,) 2.34–2.05 (8H, m), 1.84–1.44 (10H, m).

This free amine(56.9 mg, 0.142 mmol) was converted to HCl salt by treating with HCl solution in MeOH(3 ml). Evaporation of the solvent afforded pale brown amorphous solid.

IR(KBr): 3412, 1660 cm$^{-1}$ Anal. Calcd for C$_{26}$H$_{34}$N$_4$.2HCl.H$_2$O: C,63.28; H, 7.76; N, 11.35. Found: C, 63.09; H, 7.78; N, 11.50. Free amine was also converted to ethanesulfonic acid salt. Anal. Calcd for C$_{26}$H$_{34}$N$_4$.2C$_2$H$_5$SO$_3$H.1.1H$_2$O: C, 56.07; H, 7.86; N, 8.72. Found: C, 56.26; H, 7.96; N, 8.80.

Example 3
N-Phenyl-1-[1-(1-phenylcycloheptyl)-4-piperidinyl]-1H-benzimidazol-2-amine This was prepared according to the procedure described in Example 2 using aniline (10 equivalent, 120° C., 4 h) instead of methylamine and MeOH. Yield was 26%.

$^1$H NMR (270 MHz, CDCl$_3$) δ 7.60–6.96 (15H, m), 4.10–3.94 (1H, m), 3.05–2.93 (2H, m), 2.45–2.00 (8H, m), 1.90–1.68 (4H, m), 1.65–1.40 (6H, m). MS(EI) m/z: 464 (M$^+$), 292,210,91.

This free amine was converted to hydrochloride salt using HCl solution in MeOH to give pale brown amorphous solid.

IR(KBr): 3389, 1636, 1589 cm$^{-1}$ Anal. Calcd for C$_{31}$H$_{36}$N$_4$.2HCl.H$_2$O: C, 67.02; H, 7.26; N, 10.08. Found: C, 67.19; H, 7.31; N, 9.96.

Example 4
2-(4-Methylpiperazino)-1-[1-(1-phenylcycloheptyl)-4-piperidinyl]-1H-benzimidazole This was prepared according to the procedure described in Example 2 using 1-methylpiperazine (2 equivalent, 120° C., 10 h) instead of methylamine and MeOH.

Yield was 96%. $^1$H NMR (270 MHz, CDCl$_3$) δ 7.64–7.44 (4H, m), 7.39–7.30 (2H, m), 7.27–7.10 (3H, m), 4.13–3.98 (1H, m), 3.28–3.21 (4H, m), 3.06–2.95 (2H, m), 2.64–2.58 (4H, m), 2.38 (3H, s), 2.45–1.90 (8H, m), 1.85–1.45 (10H, m).

This free amine was converted to hydrochloride salt using HCl solution in MeOH to give pale yellow amorphous solid.

MS(ESI positive) m/z: 472(M+H)$^+$. IR(KBr): 3410, 1612 cm$^{-1}$ Anal. Calcd for C$_{30}$H$_{41}$N$_5$.3HCl.H$_2$O: C,60.15; H, 7.74; N, 11.69. Found: C, 59.85; H, 7.86; N, 11.64.

Example 5
2-N,N-Dimethyl-1-[1-(1-phenylcycloheptyl)-4-piperidinyl]-1H-benzimidazol-2-amine This was prepared according to the procedure described in Example 2 using dimethylamine solution in MeOH (120° C., 16 h in autoclave) instead of methylamine solution in MeOH. Yield was 97%.

$^1$H NMR (270 MHz, CDCl$_3$) δ 7.62–7.42 (4H, m), 7.38–7.30 (2H, m), 7.27–7.08 (3H, m), 4.20–4.04 (1H, m), 3.06–2.94 (2H, m), 2.88 (6H, s), 2.46–2.00 (8H, m), 1.84–1.40 (10H, m).

This free amine was converted to hydrochloride salt using HCl solution in MeOH to give pale yellow amorphous solid.

MS(ESI positive) m/z: 417(M+H)$^+$. IR(KBr): 3400, 1647 cm$^{-1}$ Anal. Calcd for C$_{27}$H$_{36}$N$_4$.2HCl.H$_2$O: C,63.90; H, 7.94; N, 11.04. Found: C, 64.03; H, 7.78; N, 10.92.

Example 6
2-Methoxy-1-[1-(1-phenylcycloheptyl)-4-piperidinyl]-1H-benzimidazole This was prepared according to the procedure described in Example 2 using sodium methoxide (10 equivalent, reflux, 10 h) and MeOH instead of methylamine solution in MeOH. Yield was 96%.

$^1$H NMR (270 MHz, CDCl$_3$) δ 7.57–7.48 (3H, m), 7.38–7.30 (3H, m), 7.27–7.07 (3H, m), 4.17 (3H, s), 4.20–4.00 (1H, m), 3.05–2.90 (2H, m), 2.35–2.00 (8H, m), 1.86–1.42 (10H, m).

This free amine was converted to fumaric acid salt using fumaric acid (1 equivalent) to give pale yellow amorphous solid.

MS(ESI positive) m/z: 404(M+H)$^+$. IR(KBr): 3400, 1703 cm$^{-1}$ Anal. Calcd for C$_{26}$H$_{33}$N$_3$O.C$_4$H$_4$O$_4$.H$_2$O: C,67.02; H, 7.31; N, 7.82. Found: C, 67.16; H, 6.95; N, 7.52.

Example 7
2-(Methylsulfanyl)-1-[1-(1-phenylcycloheptyl)-4-piperidinyl]-1H-benzimidazole This was prepared according to the procedure described in Example 2 using 15% solution of NaSMe in water and DMF (room temperature, 2 h) instead of methylamine solution in MeOH. Yield was 81%.

$^1$H NMR (270 MHz, CDCl$_3$) δ 7.70–7.62 (1H, m), 7.55–7.45 (3H, m), 7.40–7.30 (2H, m), 7.25–7.12 (3H, m), 4.16–4.03 (1H, m), 3.05–2.95 (2H, m), 2.77 (3H, s), 2.43–2.00 (8H, m), 1.90–1.1.42 (10H, m).

This free amine was converted to HCl salt using HCl solution in MeOH, mp 168–171° C.

MS(EI) m/z: 419(M$^+$), 372, 362, 183, 149, 73. IR(KBr): 3377 cm$^{-1}$ Anal. Calcd for C$_{26}$H$_{33}$N$_3$S.2HCl.2.1H$_2$O: C, 58.88; H, 7.45; N, 7.92. Found: C, 58.62; H, 7.16; N, 7.80.

Example 8
1-[1-(1-Phenylcycloheptyl)-4-piperidinyl]-2-(1-pyrrolidinyl)-1H-benzimidazole This was prepared according to the procedure described in Example 2 using pyrrolidine instead of methylamine solution in MeOH. Yield was 90%.

$^1$H NMR (270 MHz, CDCl$_3$) δ7.55–7.03 (9H, m), 4.17–4.03 (1H, m), 3.55–3.45 (4H, m), 3.05–2.95 (2H, m), 2.50–2.30 (2H, m), 2.30–1.90 (10H, m), 1.85–1.43 (10H, m).

This free amine was converted to HCl salt using HCl solution in MeOH, mp 178–181° C.

MS(EI) m/z: 442(M$^+$), 385, 269, 172, 129, 91. IR(KBr): 3366, 1620 cm$^{-1}$ Anal. Calcd for C$_{29}$H$_{38}$N$_4$.2HCl.2H$_2$O: C, 63.15; H, 8.04; N, 10.16. Found: C, 63.31; H, 7.99; N, 9.89.

Example 9
2-Morpholino-1-[1-(1-phenylcycloheptyl)-4-piperidinyl]-1H-benzimidazole This was prepared according to the procedure described in Example 2 using morpholine instead of methylamine solution in MeOH. Yield was 44%.

$^1$H NMR (270 MHz, CDCl$_3$) δ 7.70–7.58 (1H, m), 7.56–7.46 (3H, m), 7.40–7.30 (2H, m), 7.25–7.13 (3H, m), 4.16–4.03 (1H, m), 3.88 (4H, t, J=4.6 Hz), 3.20 (4H, t, J=4.6 Hz), 3.06–2.95 (2H, m), 2.47–2.00 (8H, m), 1.90–1.45 (10H, m).

This free amine was converted to HCl salt using HCl solution in MeOH, mp 172–176° C.

MS(EI) rn/z: 458(M$^+$), 402, 373, 181, 124. IR(KBr): 3396, 1612 cm$^{-1}$ Anal. Calcd for C$_{29}$H$_{38}$N$_4$O.2HCl.2.1H$_2$O: C, 63.17; H, 7.71; N, 10.16. Found: C, 62.80; H, 7.79; N, 9.76.

Preparation 1
N-1-[1-(1-Phenylcycloheptyl)-4-piperidinyl]-1,2-benzenediamine A mixture of HCl salt of 1,4-dioxa-8-azaspiro[4.5]decane (this was prepared by mixing of 1,4-dioxa-8-azaspiro[4.5]decane (11.41 g, 79.562 mmol) and 4N HCl solution in EtOAc (40 ml) followed by solidification using Et$_2$O), cycloheptanone (14.1 ml, 119.5 mmol), and aqueous solution of KCN (7.8 g, 119.8 mmol) in water (40 ml) was stirred at room temperature for 2 days. The reaction mixture was diluted with water and extracted with EtOAc. The extracts combined were washed with water and brine, dried (Na$_2$SO$_4$), filtered, and concentrated to give 22.11 g of pale yellow oil. To a stirred solution of this crude nitrile derivative (22.11 g) in Et$_2$O (260 ml) was added 3 M Et$_2$O solution of phenylmagnesium bromide (133 ml, 397.81 mmol) at 0° C. Then the reaction mixture was stirred at room temperature for 18 h. The reaction mixture was poured into aqueous solution of NH$_4$Cl and extracted with Et$_2$O. The extracts combined were washed with water and brine, dried (Na$_2$SO$_4$), filtered, and concentrated to give yellow oil. A mixture of this oil and 6 N HCl solution was stirred at 60° C. for 2 h. The reaction mixture was washed with Et$_2$O. Then aqueous layer was basified with 25% NH$_4$OH and extracted with EtOAc. The extracts combined were dried (Na$_2$SO$_4$), filtered, and concentrated to give yellow oil. This was purified by column chromatography (silica gel: 80 g, EtOAc/n-hexane: 1/7) to give 11.42 g (53%) of desired ketone derivative as a colorless oil.

$^1$H NMR (270 MHz, CDCl$_3$) δ 7.52–7.46 (2H, m), 7.35–7.18 (3H, m), 2.74 (4H, t, J=5.9 Hz), 2.30 (4H, t, J=5.9 Hz), 2.11–2.06 (4H, m), 1.78–1.47 (8H, m). MS m/z (EI direct): 271(M$^+$).

A mixture of the above ketone derivative (11.42 g, 42.078 mmol), NH$_2$OH—HCl (3.5 g, 50.494 mmol), NaOAc (5.24 g, 63.117 mmol), and EtOH (150 ml) was stirred at room temperature for 16 h. The reaction mixture was diluted with aqueous NaHCO$_3$ solution, extracted with EtOAc, washed with water and brine, dried (Na$_2$SO$_4$), filtered, and concentrated to give 10.41 g of oxime derivative as colorless solid. To a stirred solution of this oxime (10.41 g, 36.35 mmol) in THF (300 ml) was added LiAlH$_4$ (8.3 g, 218 08 mmol) at 0° C. After 10 h stirring at room temperature, the reaction mixture was quenched with Na$_2$SO$_4$—10H$_2$O and diluted with CH$_2$Cl$_2$. The solid appeared was removed by filtration. The filtrate was concentrated to give 9.94 g (100%) of 4-amino-1-(1-phenylcycloheptyl)piperidine as a colorless powder. A mixture of 4-amino-1-(1-phenylcycloheptyl) piperidine (446 mg, 1.64 mmol), 2-fluoronitrobenzene (231 mg, 1.64 mmol), and K$_2$CO$_3$ (227 mg, 1.64 mmol) in MeCN (5 ml) was refluxed for 8 h. After evaporation of the solvent, the residue was diluted with water and extracted with CH$_2$Cl$_2$. The extracts combined were washed with brine, dried (Na$_2$SO$_4$), filtered, and concentrated to give yellow oil, which was purified by column chromatography (silica gel 30 g, hexane/ethyl acetate: 10/1) to afford 557 mg (86%) of yellow oil.

$^1$H NMR (270 MHz, CDCl$_3$) δ 8.15 (1H, dd, J=1.6, 8.7 Hz), 8.08 (1H, br.d, J=7.1 Hz), 7.48–7.11 (6H, m), 6.81 (1H, br.d, J=8.4 Hz), 6.58 (1H, ddd, J=1.3, 6.9, 8.6 Hz), 3.50–3.36 (1H, m), 2.86–2.74 (2H, m), 2.33–2.22 (2H, m), 2.10–1.90 (6H, m), 1.85–1.68 (2H, m), 1.65–1.40 (8H, m). MS(EI) m/z: 393(M$^+$), 358, 336, 316, 91.

A mixture of this oil (827 mg, 2.1 mmol) and SnCl$_2$—2H$_2$O (2.37 g, 10.52 mmol) in EtOH (35 ml) was refluxed for 2.5 h. After evaporation of the solvent, saturated NaHCO$_3$ solution and CH$_2$Cl$_2$ were added to the residue.

The yellow solid formed was removed by filtration. The organic layer of the filtrate was separated and washed with brine, dried (Na$_2$SO$_4$), filtered, and concentrated to give brown solid, which was purified by column chromatography (silica gel 40 g, CH$_2$Cl$_2$/MeOH: 25/1 to 10/1) to afford 484 mg (63%) of title compound as a pale brown solid.

$^1$H NMR (270 MHz, CDCl$_3$) δ 7.56–7.42 (2H, m), 7.38–7.15 (3H, m), 6.84–6.58 (4H, m), 3.30–3.08 (1H, m), 2.90–2.72 (2H, m), 2.35–1.90 (9H, m), 1.85–1.65 (2H, m), 1.65–1.25 (10H, m).

Example 10
1-[1-(1-Phenylcycloheptyl)-4-piperidinyl]-1H-benzimidazol-2-ylamine

To a solution of BrCN (338 mg, 3.19 mmol) in water (2.9 ml) was added a solution of 1-[1-(1-phenylcycloheptyl)-4-piperidinyl]phenylene-1,2-diamine (200 mg, 0.551 mmol) in THF (2.9 ml) at room temperature. After 18 h stirring, 25% NH$_3$ solution was added to the reaction mixture and extracted with CH$_2$Cl$_2$. The extracts combined were washed with brine, dried (Na$_2$SO$_4$), filtered, and concentrated to give pale brown solid, which was purified by preparative TLC (1 mm plate×3, CH$_2$Cl$_2$/MeOH: 10/1, then 0.5 mm plate×3, CH$_2$Cl$_2$/MeOH: 10/1) to afford 77.3 mg(36%) of white amorphous solid.

$^1$H NMR (270 MHz, CDCl$_3$) δ 7.73–7.07 (11H, m), 4.62–4.42 (1H, m), 3.10–2.95 (2H, m), 2.65–2.40 (4H, m), 2.30–2.07 (4H, m), 1.90–1.65 (4H, m), 1.65–1.40 (6H, m).

This free amine was converted to HCl salt using HCl solution in MeOH to give ivory amorphous solid.

MS(ESI positive) m/z: 389(M+H)$^+$. IR(KBr): 3398, 1670 cm$^{-1}$ Anal. Calcd for C$_{25}$H$_{32}$N$_4$.2HCl.H$_2$O: C,62.62; H, 7.57; N, 11.68. Found: C, 62.66; H, 7.51; N, 11.53.

Example 11
2-Methyl-1-[1-(1-phenylcycloheptyl)-4-piperidinyl]-1H-benzimidazole

A mixture of 1-[1-(1-phenylcycloheptyl)-4-piperidinyl]phenylene-1,2-diamine (50 mg, 0.138 mmol) and acetic anhydride (19.6 μl, 0.207 mmol) in xylene (1.5 ml) was refluxed for 60 h. After cooling down to room temperature, the mixture was basified with 25% NH$_3$ solution, extracted with ethyl acetate. The extracts combined were washed with brine, dried (Na$_2$SO$_4$), filtered, and concentrated to give pale brown oil, which was purified by preparative TLC (0.5 mm plate×3, n-hexane/ethyl acetate: 2/1 3 times developed, then 0.5 mm plate×2, CH$_2$Cl$_2$/MeOH: 10/1) to afford 18.1 mg(34%) of pale brown amorphous solid.

$^1$H NMR (270 MHz, CDCl$_3$) δ 7.70–7.62 (1H, m), 7.58–7.48 (3H, m), 7.39–7.30 (2H, m), 7.27–7.17 (3H, m), 4.16–3.98 (1H, m), 3.10–2.98 (2H, m), 2.59 (3H, s), 2.45–2.00 (8H, m), 1.85–1.70 (4H, m), 1.65–1.43 (6H, m). MS(EI) m/z: 387(M$^+$), 330, 215, 172, 129,91.

This free amine was converted to HCl salt using HCl solution in MeOH to give pale brown amorphous solid.

IR(KBr): 3369 cm$^{-1}$

Example 12
1-[1-(1-Phenylcycloheptyl)-4-piperidinyl]-1H-benzimidazole

A mixture of 1-[1-(1-phenylcycloheptyl)-4-piperidinyl]phenylene-1,2-diamine (60 mg, 0.165 mmol) and formamidine acetate (35.6 mg, 0.342 mmol) in ethoxyethanol (0.3 ml) was refluxed for 1 h. After cooling down to room temperature, the mixture was basified with 25% NH$_3$ solution and extracted with CH$_2$Cl$_2$. The extracts combined were washed with brine, dried (Na$_2$SO$_4$), filtered, and concentrated to give pale brown oil, which was purified by preparative TLC (1 mm plate×3, CH$_2$Cl2/MeOH: 10/1, then 0.5 mm plate×2, n-hexane/ethyl acetate: 2/1 2 times developed) to afford 29.8 mg(48%) of pale brown amorphous solid.

$^1$H NMR (270 MHz, CDCl$_3$) δ 7.97 (1H, s), 7.82–7.76 (1H, m), 7.51–7.45 (2H, m), 7.42–7.19 (6H, m), 4.15–4.01 (1H, m), 3.06–2.96 (2H, m), 2.37–2.25 (2H, m), 2.17–1.85 (8H, m), 1.85–1.70 (2H, m), 1.65–1.43 (6H, m). MS m/z (EI): 373(M$^+$), 316, 296, 201, 172, 91.

This free amine was converted to HCl salt using HCl solution in MeOH to give yellow amorphous solid.

IR(KBr): 3400 cm$^{-1}$ Anal. Calcd for C$_{25}$H$_{31}$N$_3$.HCl.2.5H$_2$O: C,65.99; H, 8.20; N, 9.23. Found: C, 66.28; H, 8.20; N, 9.22.

Example 13
2-Isopropyl-1-[1-(1-phenylcycloheptyl)-4-piperidinyl]-1H-benzimidazole This was prepared according to the procedure described in Example 11 using isobutyric anhydride instead of acetic anhydride. Yield was 69%.

$^1$H NMR (270 MHz, CDCl$_3$) δ 7.76–7.70 (1H, m), 7.62–7.49 (3H, m), 7.39–7.31 (2H, m), 7.25–7.15 (3H, m), 4.20–4.05 (1H, m), 3.18 (1H, qq, J=6.8, 6.9 Hz), 3.09–2.99 (2H, m), 2.53–2.36 (2H, m), 2.32–2.18 (2H, m), 2.16–2.03 (4H, m), 1.85–1.45 (10H, m,), 1.41 (6H, d, J=6.8 Hz). MS m/z (EI): 415(M$^+$), 372(M$^+$—CH(CH$_3$)$_2$), 358, 243, 172.

This free amine was converted to HCl salt using HCl solution in MeOH to give pale brown amorphous solid.

IR(KBr): 3422 cm$^{-1}$ Anal. Calcd for C$_{28}$H$_{39}$N$_3$.2HCl.0.5H$_2$O: C,67.59; H, 8.10; N, 8.45. Found: C, 67.39; H, 8.30; N, 8.18.

Example 14
2-Phenyl-1-[1-(1-phenylcycloheptyl)-4-piperidinyl]-1H-benzimidazole

This was prepared according to the procedure described in Example 11 using benzoic anhydride instead of acetic anhydride. Yield was 63%.

$^1$H NMR (270 MHz, CDCl$_3$) δ 7.84–7.77 (1H, m), 7.75–7.68 (1H, m), 7.64–7.56 (2H, m), 7.54–7.47 (5H, m), 7.38–7.18 (5H, m), 4.35–4.19 (1H, m), 3.04–2.90 (2H, m), 2.58–2.40 (2H, m), 2.18–1.98 (6H, m), 1.83–1.66 (4H, m), 1.64–1.40 (6H, m). MS m/z (EI): 449(M$^+$), 392, 372, 364, 277, 194, 172.

This free amine was converted to HCl salt using HCl solution in MeOH to give pale brown amorphous solid.

IR(KBr): 3400 cm$^{-1}$ Anal. Calcd for C$_{31}$H$_{35}$N$_3$.2HCl.0.5H$_2$O: C,70.05; H, 7.21; N, 7.90. Found: C, 70.45; H, 7.51; N, 7.80.

Example 15
2-Benzyl-1-[1-(1-phenylcycloheptyl)-4-piperidinyl]-1H-benzimidazole

A mixture of 1-[1-(1-phenylcycloheptyl)-4-piperidinyl]phenylene-1,2-diamine (50 mg, 0.138 mmol) and phenylacetyl chloride (21.9 μl, 0.165 mmol) in xylene (1.5 ml) was refluxed for 15 h. After cooling down to room temperature, the mixture was basified with 25% NH$_3$ solution and extracted with ethyl acetate. The extracts combined were washed with brine, dried (Na$_2$SO$_4$), filtered, and concentrated to give brown oil, which was purified by preparative TLC (1 mm plate×3, n-hexane/ethyl acetate: 2/1) to afford 62.2 mg(94%) of white solid as amide derivative).

$^1$H NMR (270 MHz, DMSOd$_6$) δ 9.34 (1H, br.s), 7.46–7.15 (10H, m), 7.12–7.06 (1H, m), 7.02–6.93 (1H, m), 6.68–6.48 (2H, m), 4.33 (1H, br.d, J=7.6 Hz), 3.64 (2H, s), 3.22–3.05 (1H, m), 2.77–2.60 (2H, m), 2.20–1.10 (18H, m). MS(EI) m/z: 481(M$^+$), 424, 390, 308, 279, 218, 172, 91.

This amide (62.2 mg, 0.129 mmol) was refluxed in xylene (2 ml) for 38 h. After cooling down to room temperature, the mixture was purified by preparative TLC (1 mm plate×3, $CH_2Cl_2$/MeOH: 10/1) to afford 15.4 mg(26%) of pale brown solid.

$^1$H NMR (270 MHz, $CDCl_3$) δ 7.80–7.72 (1H, m), 7.60–7.43 (3H, m), 7.39–7.14 (10H, m), 4.31 (2H, s), 4.08–3.92 (1H, m), 2.92–2.78 (2H, m), 2.40–1.93 (8H, m), 1.80–1.25 (10H, m). MS m/z (EI): 463($M^+$), 406, 372, 291, 207, 172.

This free amine was converted to HCl salt using HCl solution in MeOH to give brown amorphous solid.

IR(KBr): 3356 $cm^{-1}$ Anal. Calcd for $C_{32}H_{37}N_3 \cdot 2HCl \cdot 2.5H_2O$: C, 66.08; H, 7.63; N, 7.22. Found: C, 66.08; H, 7.30; N, 6.93.

Example 16
2-Cyclohexyl-1-[1-(1-phenylcycloheptyl)-4-piperidinyl]-1H-benzimidazole This was prepared according to the procedure described in Example 15 using cyclohexanecarbonyl chloride instead of phenylacetyl chloride, and phosphoryl chloride instead of xylene. Yield was 53.9% for two steps.

$^1$H NMR (270 MHz, $CDCl_3$) δ 7.76–7.69 (1H, m), 7.62–7.50 (3H, m), 7.40–7.32 (2H, m), 7.30–7.15 (3H, m), 4.18–4.02 (1H, m), 3.10–2.98 (2H, m), 2.88–2.72 (1H, m), 2.53–1.25 (28H, m). MS m/z (EI direct): 455($M^+$), 398, 370, 283, 201. 172, 91.

This free amine was converted to HCl salt using HCl solution in MeOH to give brown amorphous solid.

IR(KBr): 3414 $cm^{-1}$ Anal. Calcd for $C_{31}H_{41}N_3 \cdot 2HCl \cdot H_2O$: C, 68.12; H, 8.30; N, 7.69. Found: C, 68.29; H, 8.33; N, 7.45.

Example 17
1-[1-(1-Phenylcycloheptyl)-4-piperidinyl]-2-piperidino-1H-benzimidazole This was prepared according to the procedure described in Example 2 using piperidine instead of methylamine in MeOH. Yield was 81%.

$^1$H NMR (270 MHz, $CDCl_3$) δ 7.64–7.44 (4H, m), 7.40–7.30 (2H, m), 7.25–7.10 (3H, m), 4.17–4.00 (1H, m), 3.20–3.10 (4H, m), 3.05–2.95 (2H, m), 2.45–2.02 (8H, m), 1.90–1.45 (16H, m).

This free amine was converted to HCl salt using HCl solution in MeOH, mp 177–180° C.

MS(EI) m/z: 456($M^+$), 399, 372, 283, 255, 202, 91. IR(KBr): 3383, 1612 $cm^{-1}$ Anal. Calcd for $C_{30}H_{40}N_4 \cdot 2HCl \cdot 1.1H_2O$: C, 65.58; H, 8.11; N, 10.20. Found: C, 65.23; H, 8.12; N, 9.89.

Example 18
2-(4-Benzylpiperazino)-1-[1-(1-phenylcycloheptyl)-4-piperidinyl]-1H-benzimidazole This was prepared according to the procedure described in Example 2 using 4-benzylpiperazine instead of methylamine in MeOH. Yield was 68%.

$^1$H NMR (270 MHz, $CDCl_3$) δ 7.64–7.44 (4H, m), 7.40–7.10 (10H, m), 4.13–4.00 (1H, m), 3.60 (2H, s), 3.30–3.18 (4H, m), 3.05–2.95 (2H, m), 2.70–2.60 (4H, m), 2.45–2.00 (8H, m), 1.90–1.45 (10H, m).

This free amine was converted to HCl salt using HCl solution in MeOH, mp 139–143° C.

MS(EI) m/z: 374($M^+$-benzylpiperazinyl), 293, 254, 172, 129, 91. IR(KBr): 3387, 1611 $cm^{-1}$ Anal. Calcd for $C_{36}H_{45}N_5 \cdot 3HCl \cdot 1.6H_2O$: C, 63.03; H, 7.52; N, 10.21. Found: C, 62.74; H, 7.62; N, 10.00.

Example 19
1-[1-(1-Phenylcycloheptyl)-4-piperidinyl]-2-piperazino-1H-benzimidazole A mixture of 2-(4-benzyl-1-piperazinyl)-1-[1-(1-phenylcycloheptyl)-4-piperidinyl]-benzimidazole (Example 18, 42.5 mg, 0.07 mmol), palladium black (12 mg), HCl solution in MeOH (0.2 M, 1.5 ml), and MeOH(8.5 ml) was stirred under hydrogen atmosphere at room temperature for 22.5 h. The mixture was basified with saturated $NaHCO_3$ solution and the catalyst was removed by filtration. The filtrate was extracted with $CH_2Cl_2$. The extracts combined were washed with brine, dried ($Na_2SO_4$), filtered, and concentrated. The residue was purified by preparative TLC (0.5 mm plate×1, $CH_2Cl_2$/MeOH/$NH_4OH$: 90/10/1 to give 29 mg (81.7%) of amorphous solid.

$^1$H NMR (270 MHz, $CDCl_3$) δ 7.65–7.58 (1H, m), 7.54–7.48 (3H, m), 7.38–7.32 (2H, m), 7.24–7.12 (3H, m), 4.16–4.04 (1H, m), 3.25–3.13 (4H, m), 3.13–2.95 (6H, m), 2.48–2.03 (4H, m), 1.90–1.40 (10H, m).

This free amine was converted to HCl salt, mp 159–163° C.

MS m/z (EI): 457($M^+$), 401, 284, 254, 204, 173, 146, 82. IR(KBr): 3348, 1591 $cm^{-1}$ Anal. Calcd for $C_{29}H_{39}N_5 \cdot 3HCl \cdot 3H_2O$: C, 56.08; H, 7.79; N, 11.28. Found: C, 56.07; H, 7.71; N, 10.92.

Example 20
N-Pentyl-1-[1-(1-phenylcycloheptyl)-4-piperidinyl]-1H-benzimidazol-2-amine This was prepared according to the procedure described in Example 2 using n-amylamine instead of methylamine in MeOH. Yield was 37.3%.

$^1$H NMR (270 MHz, $CDCl_3$) δ 7.55–7.43 (3H, m), 7.40–7.30 (2H, m), 7.28–7.18 (2H, m), 7.11–6.96 (2H, m), 4.13–4.00 (1H, m), 3.85–3.70 (1H, m), 3.60–3.45 (2H, m), 3.10–2.93 (2H, m), 2.35–2.00 (8H, m), 1.90–1.20 (16H, m), 1.00–0.85 (3H, m).

This free amine was converted to HCl salt, mp 156–159° C.

MS m/z (EI): 458($M^+$), 401, 286, 204, 172, 129, 91. IR(KBr): 3400, 1655 $cm^{-1}$ Anal. Calcd for $C_{30}H_{42}N_4 \cdot 2HCl \cdot H_2O$: C, 65.56; H, 8.44; N, 10.19. Found: C, 65.25; H, 8.35; N, 10.21.

Example 21
N-Cyclohexyl-1-[1-(1-phenylcycloheptyl)-4-piperidinyl]-1H-benzimidazol-2-amine This was prepared according to the procedure described in Example 2 using cyclohexylamine instead of methylamine in MeOH. Yield was 23%.

$^1$H NMR (270 MHz, CDCl3) δ 7.55–7.43 (3H, m), 7.40–7.30 (2H, m), 7.30–7.20 (2H, 10 m), 7.10–6.96 (2H, m), 4.05–3.87 (2H, m), 3.85–3.67 (1H, m), 3.10–2.95 (2H, m), 2.40–2.00 (8H, m), 1.90–1.10 (20H, m).

This free amine was converted to HCl salt using HCl solution in MeOH.

MS m/z (EI): 470($M^+$), 413, 298, 216, 173, 134, 91.

Example 22
N-Allyl-1-[1-(1-phenylcycloheptyl)-4-piperidinyl]-1H-benzimidazol-2-amine This was prepared according to the procedure described in Example 2 using allylamine instead of methylamine in MeOH. Yield was 15%.

$^1$H NMR (270 MHz, $CDCl_3$) δ 7.55–7.43 (3H, m), 7.40–7.20 (4H, m), 7.13–6.98 (2H, m), 6.15–6.00 (1H, m), 5.29 (1H, dd, J=1.1, 17 Hz), 5.20 (1H, br.d, J=10.3 Hz), 4.25–4.10 (3H, m), 3.87–3.72 (1H, m), 3.10–2.95 (2H, m), 2.38–1.95 (8H, m), 1.90–1.43 (10H, m).

This free amine was converted to HCl salt using HCl solution in MeOH.

MS m/z (EI): 428(M$^+$), 371, 351, 343, 256, 200, 173, 144, 118, 82.

Example 23
1-{1-[1-(4-Fluorophenyl)cycloheptyl]-4-piperidinyl}-2-(4-N-methylpiperazino)-1H-benzimidazole This was prepared according to the procedure described in Example 1 and 4 using 4-fluorophenylmagnesium bromide instead of phenylmagnesium bromide. Overall yield was 27.2%.

$^1$H NMR (270 MHz, CDCl$_3$) δ 7.64–7.59 (1H, m), 7.52–7.44 (3H, m), 7.19–7.12 (2H, m), 7.02 (2H, dd, J=8.7, 8.7 Hz), 4.13–3.98 (1H, m), 3.28–3.22 (4H, m), 3.04–2.93 (2H, m), 2.66–2.58 (4H, m), 2.38 (3H, s), 2.40–2.00 (8H, m), 1.85–1.40 (10H, m).

This free amine was converted to HCl salt using HCl solution in MeOH.

MS mi/z (EI): 490(M$^+$+1), 404, 299, 272, 218, 191, 160, 134, 109, 84. IR(KBr): 3368, 1609 cm$^{-1}$

Preparation 2
1-(Phenylcyclooctyl)piperidin-4-one

This was prepared according to the procedure of B. de Costa et al (*J.Chem.Soc.Perkin Trans.* 1, 1992, 1671–1680) using 1-phenylcyclooctylamine (R. L. McQuinn et al, *J. Med. Chem.*,1981, 24, 1429–1432) instead of 1-(2-benzo[b]thienyl)cyclohexylamine. Total yield was 39%.

$^1$H NMR (270 MHz, CDCl$_3$) δ 7.46–7.40 (2H, m), 7.35–7.18 (3H, m), 2.74 (4H, br.t, J=6.0 Hz), 2.32 (4H, br.t, J=6.0 Hz), 2.27–2.05 (4H, m), 1.80–1.30 (10H, m).

Preparation 3
N-(2-Nitrophenyl)-N-[1-(1-phenylcyclononyl)-4-piperidinyl]amine This was prepared according to the procedure of B. de Costa et al. (*J.Chem.Soc.Perkin Trans.* 1, 1992, 1671–1680) using 1-(1-Phenylcyclooctyl)piperidin-4-one instead of 1-[1-(2-benzo[b]thienyl)cyclohexyl]piperidin4-one and the procedure of N. A. Meanwell et al. (*Bioorg.Med.Chem.Lett.*, 1996, 6, 1641). Total yield was 76% yield.

$^1$H NMR (270 MHz, CDCl$_3$) δ 8.14 (1H, dd, J=1.6, 8.6 Hz), 8.05 (1H, br.d, J=7.3 Hz), 7.44–7.38 (2H, m), 7.38–7.28 (3H, m), 7.26–7.18 (1H, m), 6.78 (1H, br.d, J=8.7 Hz), 6.61–6.53 (1H, m), 3.46–3.30 (1H, m), 2.96 (2H, br.d, J=12.2 Hz), 2.30–1.90 (8H, m), 1.70–1.25 (12H, m). MS(EI) m/z: 407(M$^+$), 372, 336, 306, 286.

Preparation 4
1-[1-(1-Phenylcyclooctyl)-4-piperidinyl]1,3-dihydro-2H-1,3-benzimidazo-2-one A mixture of N-(2-nitrophenyl)-N-[1-(1-phenylcyclooctyl)-4-piperidinyl]amine (140 mg, 0.344 mmol), Raney Ni (300 mg) in EtOH (2 ml) and THF (4 ml) was stirred under hydrogen atmosphere at room temperature for 3 days. After removal of the catalyst by filtration, the filtrate was concentrated to give 133 mg of oil, which was dissolved in THF (3 ml). To this solution was added 1,1'-carbonyldiimidazole (67 mg, 0.413 mmol) and resulting mixture was stirred at room temperature for 3 days. Then the reaction mixture was diluted with saturated NaHCO$_3$ solution and extracted with CH$_2$Cl$_2$. The extracts combined were washed with water and brine, dried (Na$_2$SO$_4$), filtered, and concentrated. The residue was purified by column chromatography (silica gel; 40 g, CH$_2$Cl$_2$/MeOH: 25/1) to give 74 mg of pale brown powder. Total yield was 53%.

$^1$H NMR (270 MHz, CDCl$_3$) δ 7.50–7.20 (7H, m), 7.15–7.00 (3H, m), 4.23–4.08 (1H, m), 3.20–3.10 (2H, m), 2.40–2.00 (8H, m), 2.00–1.30 (12H, m). MS m/z (EI direct): 403(M$^+$), 332, 304, 268, 216, 184, 82.

Example 24
2-(4-Methylpiperazino)-1-[1-(1-phenylcyclooctyl)-4-piperidinyl]-1H-benzimidazole This was prepared according to the procedure described in Example 1 and 4 using 1-[1-(1-phenylcyclooctyl)-4-piperidinyl]-1,3-dihydro-2H-1,3-benzimidazo-2-one as a starting material. Overall yield was 7.8%.

$^1$H NMR (270 MHz, CDCl$_3$) δ 7.63–7.59 (1H, m), 7.54–7.44 (3H, m), 7.40–7.33 (2H, m), 7.28–7.21 (1H, m), 7.19–7.12 (2H, m), 4.10–3.94 (1H, m), 3.28–3.15 (6H, m), 2.64–2.55 (4H, m), 2.50–1.96 (11H, m, including 3H, s, at 2.36 ppm), 1.85–1.34 (12H, m).

This free amine was converted to HCl salt using HCl solution in MeOH.

MS m/z (EI): 486(M$^+$+1), 415, 400, 299, 268, 217, 184, 160, 134.

Example 25
1-[1-(1-Phenylcycloheptyl)-4-piperidinyl]-2-(4-piperidinyl)-1H-benzimidazole A mixture of 1-[1-(1-phenylcycloheptyl)-4-piperidinyl] phenylene-1,2-diamine (100 mg, 0.275 mmol) and 1-benzylpiperidine-4-carboxylic acid (500 mg, 0.5 mmol, this acid was prepared from 4-piperidinecarboxylic acid according to the procedure of F. I. Carroll et aL *J. Org. Chem.*, 1966, 31, 2957), N-ethyl-N'-3-dimethylaminopropylcarbodiimide hydrochloride (106 mg, 0.551 mmol) in CH$_2$Cl$_2$ (2 ml) was stirred at room temperature for 16 h. To the reaction mixture was added water and extracted with CH$_2$Cl$_2$. The extracts combined were washed with brine, dried (Na$_2$SO$_4$), filtered, and concentrated. The residue was purified by column chromatography (silica gel: 15 g, CH$_2$Cl$_2$/MeOH: 30/1, 1% NH$_4$OH) to give 125 mg (80%) of pale brown amorphous solid as amide derivative.

MS(EI) m/z: 564(M$^+$), 507, 473, 362, 310.

A mixture of the above amide derivative (125 mg, 0.222 mmol) and phosphoryl chloride (3 ml) was stirred at 100° C. for 2 h. After cooling down to room temperature, the reaction mixture was poured into NH$_4$OH solution and extracted with CH$_2$Cl$_2$. The extract combined was washed with brine, dried (Na$_2$SO$_4$), filtered, and concentrated to give brown oil, which was purified by preparative TLC (1 mm plate×3, CH$_2$Cl$_2$/MeOH: 10/1) to give 68.2 mg (56%) of pale brown wax.

MS m/z(EI): 546(M$^+$), 455, 400, 373, 292, 240, 173, 91. $^1$H NMR (270 MHz, CDCl$_3$) δ7.80–7.15 (14H, m), 4.20–4.00 (1H, m), 3.60 (2H, br.s), 3.20–3.00 (4H, m), 2.95–2.75 (1H, m), 3.14 (3H, d, J=4.8 Hz), 2.55–1.45 (24H, m).

A mixture of the above wax (68.2 mg, 0.125 mmol), palladium black (26 mg), and 0.2 M HCl solution in MeOH (0.81 ml) in MeOH (4.5 ml) was stirred under hydrogen atmosphere at room temperature for 15 h. Then 30 mg of palladium black was added to the mixture and stirring was continued for 20 h. Then 20 mg of palladium black was added to the mixture and stirring was continued for 14 h. After removal of the catalyst by Celite filtration, the filtrate was basified with NH$_4$OH and concentrated in vacuo. The residue was purified by preparative TLC (0.5 mm plate×4, CH$_2$Cl$_2$/EtOH: 5/1, 1% NH$_4$OH) to give 34 mg (60%) of pale yellow amorphous solid.

MS m/z(EI): 456(M$^+$), 439, 400, 348, 286, 202, 172, 145, 91. $^1$H NMR (270 MHz, CDCl$_3$) δ 7.76–7.70 (1H, m), 7.66–7.58 (1H, m), 7.56–7.50 (2H, m), 7.40–7.32 (2H, m), 7.27–7.18 (3H, m), 4.18–4.02 (1H, m), 3.30–3.21 (2H, m)

3.10–2.90 (3H, m), 2.87–2.75 (2H, m), 2.53–1.67 (17H, m), 1.68–1.45 (6H, m).

This free amine was converted to HCl salt by treating with HCl solution in MeOH. Evaporation of the solvent afforded yellow amorphous solid.

IR(KBr): 3400 cm$^{-1}$ Anal. Calcd for $C_{30}H_{40}N_4\cdot 3HCl\cdot 1.5H_2O$: C,60.76; H, 7.82; N, 9.45. Found: C, 61.13; H, 8.18; N, 9.33.

Example 26
N-Methyl-[1-(1-phenylcyclohexyl)-4-piperidinyl]-1H-benzimidazol-2-amine This was prepared according to the procedure described in Example 1 and 2 using cyclohexanone instead of cycloheptanone. Two steps yield was 38%.

$^1$H NMR (270 MHz, CDCl$_3$) δ 7.49–7.18 (7H, m), 7.10–6.95 (2H, m), 4.36–4.18 (1H, m), 3.08 (3H, d, J=4.3 Hz), 2.50–2.00 (6H, m),1.83–1.60 (6H, m),1.56–1.20 (4H, m).

This free amine was converted to hydrochloride salt using HCl solution in MeOH to give pale yellow amorphous solid.

IR(KBr): 3400, 1660 cm$^{-1}$ Anal. Calcd for $C_{25}H_{32}N_4\cdot 2HCl\cdot 0.7H_2O$: C, 63.34; H, 7.53; N, 11.82. Found: C, 63.19; H, 7.77; N, 11.87.

Example 27
N-{1-[1-(1-Phenylcycloheptyl)-4-piperidinyl]-1H-benzimidazol-2-yl}-1,2-ethanediamine A mixture of 2-chloro-1-[1-(1-phenylcycloheptyl)-4-piperidinyl]benzimidazole (Example 1, 202 mg, 0.496 mmol) and t-butyl N-(2-arninoethyl)carbamate (1 ml, 6.34 mmol) was stirred at 120° C. for 16 h and 140° C. for 3 h. After cooling down to room temperature, water was added to the mixture and extracted with CH$_2$Cl$_2$. The extracts combined were washed with brine, dried (Na$_2$SO$_4$), filtered, and concentrated. The resulting residue was purified by column chromatography (silica gel: 50 g, CH$_2$Cl$_2$/MeOH: 40/1 to 20/1) to give 194 mg (73.6%) of colorless amorphous solid.

$^1$H NMR (270 MHz, CDCl$_3$) δ 7.53–7.41(2H, m), 7.37–7.19 (5H, m), 7.10–6.97 (2H, m), 5.72–5.61 (1H, m), 3.86–3.72 (1H, m), 3.62–3.60 (2H, m), 3.49–3.41 (2H, m), 3.00–2.96 (2H, m), 2.35–2.16 (4H, m), 2.11–2.04 (4H, m), 1.76–1.71 (5H, m), 1.54–1.47 (5H, m), 1.42 (9H, s). MS(EI) m/z: 531(M$^+$).

A solution of the above Boc derivative (95.3 mg, 0.179 mmol) in HCl solution in MeOH (2 ml) was stirred at room temperature for 16 h. After evaporation of the solvent, the residue was basified with saturated NaHCO$_3$ solution, extracted with CH$_2$Cl$_2$, dried (Na$_2$SO$_4$), filtered, and concentrated. The residue was purified by preparative TLC (1 mm plate×1, CH$_2$Cl$_2$/MeOH/NH$_4$OH:100/10/1) to give 38 mg (49.1%) of colorless amorphous solid.

$^1$H NMR (270 MHz, CDCl$_3$) δ 7.50–7.46 (2H, m), 7.41–7.17 (6H, m), 7.07–6.97 (2H, m), 3.98–3.86 (1H, m), 3.61–3.56 (2H, m), 3.11–3.06 (2H, m), 2.96–2.92 (2H, m), 2.13–2.13 (4H, m), 2.10–2.04 (4H, m), 1.73–1.68 (5H, m), 1.52–1.44 (5H, m).

This free amine was converted to HCl salt using HCl solution in MeOH to give colorless solid, mp 228–232° C.

IR(KBr): 2930, 2860, 1650, 1480 cm$^{-1}$ Anal. Calcd for $C_{27}H_{37}N_5\cdot 3HCl\cdot 1.5MeOH$: C, 58.11; H, 7.87; N, 11.89. Found: C, 57.97; H, 7.68; N, 11.49.

Example 28
N-Methyl-1-[1-(1-methylcyclononyl)-4-piperidinyl]-1H-benzimidazol-2-amine This was prepared according to the procedure described in Example 1 and 2 using cyclononanone instead of cycloheptanone and methylmagnesium bromide instead of phenylmagnesium bromide. Overall yield was 22.9%.

$^1$H NMR (270 MHz, CDCl$_3$) δ 7.50 (1H, br.d, J=7.9 Hz), 7.35–7.15 (1H, m), 7.13–6.98 (2H, m), 4.40–4.20 (1H, m), 3.95–3.70 (1H, m), 3.30–3.00 (2H, m), 3.15 (3H, d, J=4.5 Hz), 2.45–2.10 (4H, m), 2.00–1.30 (18H, m), 0.85 (3H, br.s).

This free amine was converted to HCl salt using HCl solution in MeOH to give colorless amorphous solid.

MS(EI) m/z: 368(M$^+$), 354, 338, 283, 222, 147, 82. IR(KBr): 3406, 1661 cm$^{-1}$ Anal. Calcd for $C_{23}H_{36}N_4\cdot 2HCl\cdot 1.8H_2O$: C,58.29; H, 8.85; N, 11.82. Found: C, 58.58; H, 9.00; N, 11.83.

Example 29
1-[1-(1-Ethylcyclononyl)-4-piperidinyl]-N-methyl-1H-benzimidazol-2-amine This was prepared according to the procedure described in Example 1 and 2 using cyclononanone instead of cycloheptanone and ethylmagnesium bromide instead of phenylmagnesium bromide. Overall yield was 17.3%.

$^1$H NMR (270 MHz, CDCl$_3$) δ 7.50 (1H, br.d, J=7.8 Hz), 7.35–7.25 (1H, m), 7.14–6.98 (2H, m), 4.42–4.30 (1H, m), 3.94–3.80 (1H, m), 3.35–3.16 (2H, m), 3.15 (3H, d, J=4.1 Hz), 2.50–2.15 (4H, m), 2.00–1.30 (20H, m), 0.86 (3H, br.t).

This free amine was converted to HCl salt using HCl solution in MeOH to give colorless amorphous solid.

MS(EI) m/z: 382(M$^+$), 353, 338, 297, 206. IR(KBr): 3416, 1661 cm$^{-1}$

Example 30
1-[1-(1-Phenylcyclononyl)-4-piperidinyl]-1H-benzimidazol-2-amine

This was prepared according to the procedure described in Preparation 1, 2, 3, and Example 10 using 1-phenylcyclononylamnine as starting material which was reported by R. L. McQuinn et al, *J. Med. Chem.*, 1981, 24, 1429–1432. Overall yield was 22.3%.

$^1$H NMR (270 MHz, CDCl$_3$) δ 7.50–7.20 (7H, m), 7.13–7.01 (2H, m), 3.92–3.74 (1H, m), 3.30–3.18 (2H, m), 2.40–2.20 (2H, m), 2.18–1.93 (6H, m), 1.84–1.73 (2H, m), 1.70 –1.24 (12H, m).

This free amine was converted to HCl salt using HCl solution in MeOH to give colorless amorphous solid.

MS(EI) m/z: 416(M$^+$), 331, 303, 216, 134, 91. IR(KBr): 3350, 1668 cm$^{-1}$ Anal. Calcd for $C_{27}H_{36}N_4\cdot 2HCl\cdot 1.7H_2O$: C,62.35; H, 8.02; N, 10.77. Found: C, 62.53; H, 7.94; N, 10.46.

Preparation 5
1-(4-Fluorophenyl)cyclononylamine

This was prepared according to the procedure of R. L. McQuinn et al, (*J.Med.Chem.*,1981, 24, 1429–1432) using 4-fluorophenylmagnesium bromide instead of phenylmagnesium bromide. Total yield was 28%.

$^1$H NMR (270 MHz, CDCl$_3$) δ 7.54–7.46 (2H, m), 7.05–6.95 (2H, m), 2.10–1.72 (4H, m), 1.70–1.35 (14H, m).

Example 31
1-{1-[1-(4-Fluorophenyl)cyclononyl]-4-piperidinyl}-1H-benzimidazol-2-amine This was prepared according to the procedure described in Example 30 using 1-(4-fluorophenyl)cyclononylarnine as starting material. Overall yield was 29.7%.

$^1$H NMR (270 MHz, CDCl$_3$) δ 7.48–7.26 (4H, m), 7.15–6.98 (4H, m), 3.92–3.77 (1H, m), 3.28–3.15 (2H, m), 2.37–2.20 (2H, m), 2.18–1.92 (6H, m), 1.86–1.75 (2H, m), 1.66–1.24 (12H, m).

This free amine was converted to HCl salt using HCl solution in MeOH to give colorless amorphous solid.

MS(EI) m/z: 434(M+), 349, 321, 216, 134, 109, 82. IR(KBr): 3350, 1670 cm$^{-1}$ Anal. Calcd for $C_{27}H_{35}FN_4$·2HCl·1.7$H_2O$: C,60.26; H, 7.57; N, 10.41. Found: C, 60.29; H, 7.62; N, 10.19.

Example 32
N-{1-[1-(1-Phenylcycloheptyl)-4-piperidinyl]-1H-benzimidazol-2-yl}acetamide A mixture of 2-amino-1-[1-(1-phenylcycloheptyl)-4-piperidinyl]benzimidazole (Example 10, 85.4 mg, 0.22 mmol) and acetyl chloride (17.2 μl, 0.242 mmol) in pyridine (1 ml) was stirred at room temperature for 144 h. After evaporation of the solvent, the residue was purified by preparative TLC(1 mm plate×2, $CH_2Cl_2$/MeOH: 40/1) to give 20 mg (21%) of pale brown amorphous solid.

$^1$H NMR (270 MHz, $CDCl_3$) δ 7.56–7.48 (3H, m), 7.38–7.14 (6H, m), 4.80–4.62 (1H, m), 3.06–2.90 (2H, m), 2.40–2.25 (4H, m), 2.23 (3H, s), 2.20–2.00 (4H, m), 1.90–1.45 (10H, m).

This free amine was converted to HCl salt using HCl solution in MeOH to give pale brown amorphous solid.

IR(KBr): 3400, 1728 cm$^{-1}$ Anal. Calcd for $C_{27}H_{34}N_4O$·2HCl·3.9$H_2O$: C,60.56; H, 8.02; N, 10.46. Found: C, 60.27; H, 7.62; N, 10.48.

Example 33
N-[2-({1-[1-(1-Phenylcycloheptyl)-4-piperidinyl]-1H-benzimidazol-2-yl}amino)ethyl]guanidine A mixture of 2-aminoethylamino-1-[1(1-phenylcycloheptyl)-4-piperidinyl]benzimidazole (Example 27, 85.6 mg, 0.199 mmol) and N, N'-bis Boc guanylpyrazole (117 mg, 0.377 mmol, this was prepared according to the following reported procedure: M. S. Bernatowicz, et al., *Tetrahedron Lett.*, 1993, 34, 3389–3392) in THF (3 ml) was stirred at room temperature for 16 h. Water was added to the reaction mixture and extracted with $CH_2Cl_2$. The extracts combined were washed with brine, dried ($Na_2SO_4$), filtered, and concentrated. The residue was purified by column chromatography (silica gel: 30 g, hexane/acetone: 4/1 to 3/1) to give 95.5 mg (71.4%) of colorless amorphous solid.

$^1$H NMR (270 MHz, $CDCl_3$) δ 11.46 (1H, br.s), 8.70 (1H, br.s), 7.51–7.45 (2H, m), 7.37–7.19 (5H, m), 7.11–6.99 (2H, m), 4.71–4.58 (1H, m), 3.78–3.74 (4H, m), 3.02–2.98 (2H, m), 2.30–2.09 (8H, m), 1.78–1.74 (5H, m), 1.42–1.51 (24H, m).

A solution of above Boc derivative (95.5 mg, 0.144 mmol) in trifluoroacetic acid (1 ml) and $CH_2Cl_2$ (1 ml) was stirred at room temperature for 2 h. After evaporation of the solvent, HCl solution in MeOH (3 ml) was added to the residue and the resulting mixture was stirred at room temperature for 17 h. After evaporation of the solvent, the residue was solidified by scratching in ether to give 60 mg (71.4%) of solid, mp 215–218° C.

$^1$H NMR (270 MHz, DMSO-$d_6$) δ 13.56 (1H, br.s), 10.83 (1H, br.s), 9.24 (1H, br.s), 8.20 (1H, br.s), 7.91 (1H, br.s), 7.80–7.65 (2H, m), 7.50–7.00 (10H, m), 5.05–4.85 (1H, m), 3.60–2.60 (10H, m), 2.00–1.00 (14H, m). MS(ESI positive) m/z: 474(M+H)+. IR(KBr): 3329, 1660 cm$^{-1}$ Anal. Calcd for $C_{28}H_{39}N_7$·3HCl·4$H_2O$: C,51.34; H, 7.69; N, 14.97. Found: C, 51.58; H, 7.69; N, 15.07.

Example 34
N-{1-[1-(1-phenylcycloheptyl)-4-piperidinyl]-1H-benzimidazol-2-yl}-N-(4-piperidinyl)amine To a stirred solution of 1-[1-(1-phenylcycloheptyl)-4-piperidinyl]phenylene-1,2-diamine (253 mg, 0.697 mmol) in EtOH (4 ml) was added a solution of ethyl 4-isothiocyanato-1-piperidinecarboxylate (478 mg, 2.23 mmol, this was prepared according to the procedure of F. Janssens et al., *J. Med. Chem.*, 1985, 28, 1925–1933) in EtOH (3 ml) and the reaction mixture was stirred at 70° C. for 2.5 h. After cooling down to room temperature, the reaction mixture was poured into water and extracted with $CH_2Cl_2$. The extracts combined were washed with brine, dried ($Na_2SO_4$), filtered, and concentrated. The residue was purified by column chromatography (silica gel: 100 g, hexane/ether: 3/7 to ether only) to afford 338 mg (84%) of thiourea derivative as colorless amorphous solid.

A solution of above thiourea derivative (321 mg, 0.556 mmol) and iodomethane (0.346 ml) in EtOH (5 ml) was refluxed for 1 h. The reaction mixture was cooled down to room temperature, basified with 25% $NH_4OH$ solution, and extracted with $CH_2Cl_2$. The extracts combined were washed with brine, dried ($Na_2SO_4$), filtered, and concentrated to give colorless amorphous solid. A mixture of this solid, 2M KOH (2 ml), and THF (4 ml) was stirred at room temperature for 10 h. The mixture was poured into water and extracted with $CH_2Cl_2$. The extracts combined were washed with brine, dried ($Na_2SO_4$), filtered, and concentrated. The residue was purified by column chromatography (silica gel: 40 g, hexane/acetone: 7/3) to give 156 mg (51.6%) of carbamate derivative as colorless amorphous solid.

$^1$H NMR (270 MHz, $CDCl_3$) δ 7.51–7.44 (3H, m), 7.38–7.20 (4H, m), 7.12–6.99 (2H, m), 4.19–4.07 (4H, m), 3.96–3.93 (1H, m), 3.79–3.69 (1H, m), 3.09–2.99 (4H, m), 2.32–2.04 (10H, m), 1.80–1.71 (5H, m), 1.55–1.36 (5H, m), 1.31–1.21 (3H, m).

A solution of above carbamate derivative (120 mg, 0.22 mmol) in 25% HBr solution in AcOH (2 ml) was stirred at 70° C. for 14 h. After cooling down to room temperature, the reaction mixture was poured into water and extracted with $CH_2Cl_2$. The extracts combined were washed with brine, dried ($Na_2SO_4$), filtered, and concentrated. The residue was purified by column chromatography (silica gel: 20 g, $CH_2Cl_2$/MeOH/$NH_4OH$:100/10/1) to afford 81.2 mg of desired product as colorless solid, but it still included some impurity. Purification using preparative TLC was not successful. This free amine was converted to Boc derivative and purified, then de-protected to give pure desired product as follows.

To a solution of above amine with impurity (43.7 mg, 0.0928 mmol) in $CH_2C_{12}$ (1 ml) was added a solution of di-t-butyl dicarbonate (24.3 mg, 0.111 mmol) in $CH_2Cl_2$ (0.5 ml) and the mixture was stirred at room temperature for 0.5 h. The reaction mixture was basified with saturated $NaHCO_3$ solution and extracted with $CH_2Cl_2$. The extracts combined were washed with brine, dried ($Na_2SO_4$), filtered, and concentrated. The residue was purified by preparative TLC (0.5 mm plate×2, $CH_2Cl_2$/MeOH: 9/1) to give 40.4 mg (76.3%) of colorless amorphous solid.

$^1$H NMR (270 MHz, $CDCl_3$) δ 7.51–7.44 (3H, m), 7.38–7.20 (4H, m), 7.11–6.99 (2H, m), 4.17–3.93 (4H, m), 3.80–3.68 (1H, m), 3.04–2.94 (4H, m), 2.28–2.10 (10H, m), 1.78–1.73 (5H, m), 1.48–1.34 (14H, m).

A mixture of above Boc derivative (40.4 mg, 0.0708 mmol) and HCl solution in MeOH (2 ml) was stirred at room temperature for 17 h. Evaporation of the solvent gave 25 mg of HCl salt of desired product, mp 231–235° C.

$^1$H NMR (270 MHz, $CDCl_3$) δ 10.79 (1H, br.s), 9.25–8.75 (2H, m), 8.21 (1H, br.s), 7.80–7.70 (2H, m), 7.50–7.30 (4H, m), 7.25–7.05 (3H, m), 5.05–4.85 (1H, m), 4.00–3.85 (1H, m), 3.55–3.20 (4H, m), 3.15–2.60 (8H, m), 2.50–2.30 (2H, m), 2.10–1.70 (9H, m), 1.55–1.05 (6H, m). MS(ESI positive) m/z: 472(M+H)+. IR(KBr): 3389, 1645 cm$^{-1}$ Anal. Calcd for $C_{30}H_{41}N_5$·3HCl·3$H_2O$: C, 57.36; H, 8.07; N, 10.79. Found: C, 57.35; H, 8.30; N, 10.88.

Example 35
N-Methyl-N'-{1-[1-(1-Phenylcycloheptyl)-4-piperidinyl]-1H-benzimidazol-2-yl}-1,2-ethanediamine This was prepared according to the procedure described in Example 1 and Example 3 using N-methylethylenediamine (140_C, 4.5 h) instead of aniline. Yield was 31%.

$^1$H NMR (270 MHz, CDCl$_3$) δ7.52–7.42 (3H, m), 7.37–7.18 (4H, m), 7.11–6.96 (2H, m), 5.23–5.00 (1H, almost flat br.s), 3.90–3.75 (1H, m), 3.65–3.50 (2H, m), 3.10–2.90 (4H, m), 2.47 (3H, s), 2.35–2.00 (8H, m), 1.85–1.43 (10H, m).

This free amine was converted to HCl salt using HCl solution in MeOH, mp 173–177° C. MS(ESI positive) m/z: 446(M+H)$^+$. IR(KBr): 3383, 1649 cm$^{-1}$ Anal. Calcd for C$_{28}$H$_{39}$N$_5$.3HCl.2.7H$_2$O: C, 55.71; H, 7.91; N, 11.60. Found: C, 56.09; H, 8.22; N, 11.20.

Example 36
N,N-Dimethyl-N'-{1-[1-(-Phenylcyclobeptyl)-4-piperidinyl]-1H-benzimidazol-2-yl}-1,2-ethanediamine This was prepared according to the procedure described in Example 1 and Example 3 using N,N-dimethylethylenediamine (120° C., 16.5 h) instead of aniline. Yield was 62%.

$^1$H NMR (270 MHz, CDCl$_3$) δ 7.55–7.42 (3H, m), 7.40–7.19 (4H, m), 7.13–6.98 (2H, m), 5.39 (1H, br.s), 4.00–3.83 (1H, m), 3.59 (2H, t, J=5.4 Hz), 3.10–2.90 (2H, m), 2.66 (2H, t, J=5.4 Hz), 2.35 (6H, s), 2.36–2.00 (8H, m), 1.90–1.43 (10H, m).

This free amine was converted to HCl salt using HCl solution in MeOH, mp 188–192° C.

MS(ESI positive) m/z: 460(M+H)$^+$. IR(KBr): 3383, 1649 cm$^{-1}$ Anal. Calcd for C$_{29}$H$_{41}$N$_5$.3HCl.2H$_2$O: C, 57.56; H, 8.00; N, 11.57. Found: C, 57.47; H, 8.31; N, 11.18.

Example 37
1-(4-{1-[1-(1-Phenylcycloheptyl)-4-piperidinyl]-1H-benzimidazol-2-yl}-piperazino)-1-ethanone A mixture of 1-[1-(1-Phenylcycloheptyl)-4-piperidinyl]-2-piperazinobenzimidazole (Example 19, 45.8 mg, 0.1 mmol), acetyl chloride (0.03 ml), and pyridine (0.1 ml) in CH$_2$Cl$_2$ was stirred at room temperature for 1 h. The reaction mixture was poured into water and extracted with ethyl acetate. The extracts combined were washed with brine, dried (Na$_2$SO$_4$), filtered, and concentrated. The residue was purified by preparative TLC (1 mm plate×1, CH$_2$Cl$_2$/MeOH: 9/1) to afford 35.3 mg (70.6%) of colorless solid.

$^1$H NMR (270 MHz, CDCl$_3$) δ 7.64–7.57 (1H, m), 7.53–7.50 (3H, m), 7.38–7.32 (2H, m), 7.27–7.14 (3H, m), 4.16–4.03 (1H, m), 3.82–3.77 (2H, m), 3.68–3.63 (2H, m), 3.28–3.23 (2H, m), 3.05–2.97 (2H, m), 2.50–2.17 (4H, m), 2.15 (3H, s), 2.13–2.09 (4H, m), 1.79–1.68 (5H, m), 1.57–1.54 (5H, m).

This free amine was converted to HCl salt using HCl solution in MeOH, mp 188–192° C.

MS(ESI positive) m/z: 460(M+H)$^+$. IR(KBr): 3383, 1649 cm$^{-1}$ Anal. Calcd for C$_{29}$H$_{41}$N$_5$.3HCl.2H$_2$O: C, 57.56; H, 8.00; N, 11.57. Found: C, 57.47; H, 8.31; N, 11.18.

Example 38
1-[1-(1-Phenylcycloheptyl)-4-piperidinyl]-2-(4-phenylpiperazino)-1H-benzimidazole This was prepared according to the procedure described in Example 1 and Example 4 using 1-phenylpiperazine (140° C., 7.5 h) instead of 1-methylpiperazine. Yield was 81%.

$^1$H NMR (270 MHz, CDCl$_3$) δ 7.67–7.60 (1H, m), 7.55–7.48 (3H, m), 7.38–7.13 (7H, m), 7.03–6.87 (3H, m), 4.20–4.06 (1H, m), 3.37 (8H, s), 3.07–2.97 (2H, m), 2.50–2.00 (8H, m), 1.90–1.40 (10H, m).

This free amine was converted to HCl salt using HCl solution in MeOH, mp 188–192° C.

MS(EI) m/z: 533(M$^+$), 360, 279, 172, 146. IR(KBr): 3396,1595 cm$^{-1}$ Anal. Calcd for C$_{35}$H$_{43}$N$_5$.3HCl.1.5MeOH: C, 63.43; H, 7.58; N, 10.13. Found: C, 63.23; H, 7.84; N, 10.20.

Example 39
1-[1-(1-Phenylcycloheptyl)-4-piperidinyl]-2-(4-pyridinyl)-1H-benzimidazole This was prepared according to the procedure described in Preparation 1 and Example 11 using isonicotinic anhydride (120° C., 16 h) instead of acetic anhydride. Yield was 82%.

$^1$H NMR (270 MHz, CDCl$_3$) δ 8.81–8.77 (2H, m), 7.86–7.70 (2H, m), 7.55–7.47 (4H, m), 7.38–7.19 (5H, m), 4.30–4.18 (1H, m), 3.05–2.94 (2H, m), 2.58–2.42 (2H, m), 2.20–2.03 (5H, m), 1.86–1.42 (11H, m). MS(EI) m/z: 450 (M$^+$), 393, 278, 172, 129, 91.

This free amine was converted to HCl salt using HCl solution in MeOH.

IR(KBr): 3395, 1637 cm$^{-1}$ Anal. Calcd for C$_{30}$H$_{34}$N$_4$.3HCl.H$_2$O.0.3MeOH: C, 61.93; H, 6.90; N, 9.53. Found: C, 62.11; H, 7.27; N, 9.33.

Example 40
2-Methybsulfonyl-1-[1-(1-phenylcycloheptyl)-4-piperidinyl]-1H-benzimidazole To a stirred solution of 2-methylthio-1-[1-(1-phenylcycloheptyl)-4-piperidinyl]-1H-benzimidazole (Example 7, 74.6 mg, 0.178 mmol) in acetic acid (1 ml) was added a solution of potassium permanganate (62.6 mg) in water (2 ml) at room temperature. After 1 h stirring, the reaction mixture was quenched with saturated Na$_2$SO$_4$ solution, basified with 25% NH$_4$OH, and extracted with ethyl acetate. The extracts combined were washed with water and brine, dried (Na$_2$SO$_4$), filtered, and concentrated to give 67 mg of colorless solid. This was purified by preparative TLC (1 mm plate×1, hexane/acetone: 4/1 three times developed) to give 25.6 mg (32%) of colorless amorphous solid.

$^1$H NMR (270 MHz, CDCl$_3$) δ 7.82–7.72 (2H, m), 7.54–7.50 (2H, m), 7.45–7.31 (3H, m), 7.27–7.20 (2H, m), 5.01–4.90 (1H, m), 3.57 (3H, s), 3.02–2.98 (2H, m), 2.44–2.28 (4H, m), 2.11–1.94 (4H, m), 1.82–1.47 (10H, m). MS(EI) m/z: 451(M$^+$), 394, 372, 332, 254, 200, 172, 129, 91.

This free amine was converted to HCl salt using HCl solution in MeOH to give solid, mp 155–158° C.

IR(KBr): 3381, 1693 c$^{-1}$ Anal. Calcd for C$_{26}$H$_{33}$N$_3$O$_2$S.HCl.1.7H$_2$O: C, 60.20; H, 7.27; N, 8.10. Found: C, 60.14; H, 7.38; N, 7.70.

Example 41
2-(4-Methylpiperazino)-1-[1-(1-methylcyclooctyl)-4-piperidinyl]-1H-benzimidazole This was prepared according to the procedure described in Example 1 and 4 using cyclooctanone instead of cycloheptanone and methylmagnesium bromide instead of phenylmagnesium bromide. Four steps yield was 12.7%.

$^1$H NMR (270 MHz, CDCl$_3$) δ 7.66–7.60 (1H, m), 7.58–7.48 (1H, m), 7.20–7.11 (2H, m), 4.20–4.05 (1H, m), 3.32–3.25 (4H, m), 3.23–3.10 (2H, m), 2.67–2.61 (4H, m), 2.60–2.40 (2H, m), 2.39 (3H, s), 2.28–2.14 (2H, m), 2.05–1.68 (6H, m), 1.67–1.30 (10H, m), 0.90 (3H, br.s).

This free amine was converted to HCl salt using HCl solution in MeOH to give colorless amorphous solid.

MS(EI) m/z: 423(M$^+$), 353, 338, 298, 217, 206. Anal. Calcd for C$_{26}$H$_{41}$N$_5$.3HCl.4H$_2$O: C,51.61; H, 8.66; N, 11.57. Found: C, 51.90; H, 8.92;N, 11.37.

Example 42
2-(4-Methylpiperazino)-1-[1-(1-methylcyclononyl)-4-piperidinyl]-1H-benzimidazole This was prepared according to the procedure described in Example 1 and 4 using cyclononanone instead of cycloheptanone and methylmagnesium bromide instead of phenylmagnesium bromide. Four steps yield was 16.9%.

$^1$H NMR (270 MHz, CDCl$_3$) δ 7.66–7.60 (1H, m), 7.58–7.48 (1H, m), 7.20–7.11 (2H, m), 4.20–4.04 (1H, m), 3.32–3.25 (4H, m), 3.24–3.16 (2H, m), 2.67–2.60 (4H, m), 2.55–2.40 (2H, m), 2.38 (3H, s), 2.25–2.13 (2H, m), 1.85–1.35 (18H, m), 0.85 (3H, s).

This free amine was converted to HCl salt using HCl solution in MeOH to give colorless amorphous solid.

MS(EI) m/z: 437(M$^+$), 367, 352, 298, 220. IR(KBr): cm$^{-1}$ Anal. Calcd for C$_{27}$H$_{43}$N$_5$.3HCl.5H$_2$O: C,50.90; H, 8.86; N, 10.99. Found: C, 51.28; H,9.01;N, 11.23.

Example 43
3-Amino-1-{1-[1-(1-phenylcycloheptyl)-4-piperidinyl]-1H-benzimidazol-2-yl}-1-propanone To a stirred solution of 1-[1-(1-phenylcycloheptyl)-4-piperidinyl]-1H-benzimidazole (Example 12, 66.3 mg, 0.178 mmol) in THF(4 ml) was added n-butyllithium (1.54M solution in hexane, 0.923 ml, 1.42 mmol) at −78° C. After 1 h stirring at −78° C., a solution of 3-t-butoxycarbonylamino-N-methoxy-N-methylpropionamide (140 mg, 0.604 mmol, this was prepared according to the reported procedure: G. Bitan et al, *J. Chem. Soc., Perkin Trans.* 1, 1997, 1501–1510) in THF (1.5 ml) was added to the reaction mixture at −78° C. After 0.5 h stirring at −78° C. and 15 h stirring at ambient temperature, the reaction mixture was quenched with water and extracted with ethyl acetate. The extracts combined were washed with brine, dried (Na$_2$SO$_4$), filtered, and concentrated. The residue was purified by preparative TLC (1 mm plate×3, n-hexane/acetone: 5/1, 6 times developed) to give 71.7 mg (74%) of pale brown amorphous solid. This solid (70 mg, 0.131 mmol) was dissolved in HCl solution in MeOH (10 ml). After evaporation of the solvent, the residue was dried in vacuo at 45° C. for 18 h to afford 60 mg (89%) of pale brown amorphous solid.

IR(KBr): 3395, 2931, 1692, 1611, 1477 cm$^{-1}$ Anal. Calcd for C$_{28}$H$_{36}$N$_4$O.2HCl.2H$_2$O: C,60.75; H, 7.65; N, 10.12. Found: C, 60.90; H, 7.98; N, 9.95. Small amount of this HCl solid was basified to give free amine.

$^1$H NMR (270 MHz, CDCl$_3$) δ 7.90–7.74 (2H, m), 7.56–7.50 (2H, m), 7.42–7.19 (5H, m), 5.51–5.30 (1H, m), 3.48 (2H, t, J=6.1 Hz), 3.15 (2H, t, J=6.1 Hz), 3.02–2.94 (2H, m), 2.50–2.25 (4H, m), 2.24–2.00 (5H, m), 1.95–1.40 (11H, m). MS(ESI positive) m/z: 445(M+H)$^+$.

Example 44
1-{1-[1-(4-Fluorophenyl)cycloheptyl]-4-piperidinyl}-N-methyl-1H-benzimidazol-2-amine This was prepared according to the procedure described in Example 23 and 2. The two steps yield was 58.4%.

$^1$H NMR (270 MHz, CDCl$_3$) δ 7.52–7.40 (3H, m), 7.29–7.23 (1H, m), 7.13–6.97 (4H, m), 4.24 (1H, br.s), 3.84–3.68 (1H, m), 3.13 (3H, br.d, J=3.0 Hz), 3.02–2.91 (2H, m), 2.32–1.90 (9H, m), 1.84–1.40 (9H, m).

This free amine was converted to HCl salt using HCl solution in MeOH to give colorless amorphous solid.

MS(EI) m/z: 420(M$^+$), 363, 335,274,231, 191, 174,148, 123. IR(KBr): 3400, 1661 cm$^{-1}$ Anal. Calcd for C$_{26}$H$_{33}$FN$_4$.2HCl.1.6H$_2$O: C,60.46; H, 7.55; N, 10.45. Found: C, 60.21; H, 7.34; N, 10.20.

Preparation 6
4-Fluoro-1-[1-(1-phenylcycloheptyl)-4-piperidinyl]-1,3-dihydro-2H-1,3-benzimidazol-2-one A mixture of 3-fluoro-N-1-[1-(1-phenylcycloheptyl)-4-piperidinyl]-1,2-benzenediamine (this was prepared according to the procedure described in Preparation 1 using 2,6-difluoronitrobenzene instead of 2-fluoronitrobenzene, 178.5 mg. 0.468 mmol) and triphosgene (180 mg, 0.608 mmol) in benzene (8 ml) was stirred at room temperature. The reaction mixture was then refluxed for 30 min. The reaction mixture was cooled down to room temperature, basified by adding aqueous NaHCO$_3$ solution, and extracted with CH$_2$Cl$_2$. The extracts combined were dried (Na$_2$SO$_4$), filtered, and concentrated to give 76.3 mg (40%) of title compound as white solid.

$^1$H NMR (270 MHz, CDCl$_3$) δ 8.99(1H, br.s), 7.55–7.47 (2H, m), 7.37–7.17 (3H, m), 7.05–6.96 (2H, m), 6.87–6.76 (1H, m), 4.30–4.18 (1H, m), 3.00–2.88 (2H, m), 2.33–2.00 (8H, m), 1.88–1.40 (10H, m).

Example 45
4-Fluoro-2-(4-methyl-1-piperazinyl)-1-[1-(1-phenylcycloheptyl)-4-piperidinyl]-1H- benzimidazole This was prepared according to the procedure described in Example 1 and 4 using 4-fluoro-1-[1-(1-phenylcycloheptyl)-4-piperidinyl]- 1,3-dihydro-2H-1,3-benzimidazol-2-one as starting material. The two steps yield was 49.3%.

$^1$H NMR (270 MHz, CDCl$_3$) δ 7.55–7.48 (2H, m), 7.39–7/31 (2H, m), 7.28–7.19 (2H, m), 7.05 (1H, dt, J=4.9, 8.1 Hz), 6.86 (1H, dd, J=8.2, 10.4 Hz), 4.13–3.80 (1H, m), 3.32–3.24 (4H, m), 3.06–2.96 (2H, m), 2.66–2.57 (4H, m), 2.37 (3H, s), 2.34–2.00 (8H, m), 1.90–1.42 (10H, m).

This free amine was converted to HCl salt using HCl solution in MeOH to give colorless amorphous solid.

MS(ESI positive) m/z: 490(M+H)$^+$. IR(KBr): 3369, 1618 cm$^{-1}$ Anal. Calcd for C$_{30}$H$_{40}$FN$_5$.3HCl.2H$_2$O: C,56.74; H, 7.46; N, 11.03. Found: C, 57.04; H, 7.52; N, 11.07.

Preparation 7
5-Fluoro-1-[1-(1-phenylcycloheptyl)-4-piperidinyl]-1,3-dihydro-2H-1,3-benzimidazol-2-one This was prepared according to the procedure described in preparation 4 using 2,5-difluoronitrobenzene instead of 2,6-difluoronitrobenzene. The three step yield from 2,5-difluoronitrobenzene was 9.7%.

$^1$H NMR (270 MHz, CDCl$_3$) δ 9.45 (1H, br.s), 7.55–7.45 (2H, m), 7.37–7.18 (3H, m), 7.12 (1H, dd, J=4.5, 8.6 Hz), 6.87–6.73 (2H, m), 4.284.15 (1H, m), 3.05–2.88 (2H, m), 2.35–2.00 (8H, m), 1.90–1.40 (10H, m). MS m/z(ESI positive): 408(M+H)$^+$.

Example 46
5-Fluoro-2-(4-methyl-1-piperazinyl)-1-[1-(1-phenylcycloheptyl)-4-piperidinyl]-1-H-benzimidazole This was prepared according to the procedure described in Example 45 using 5-fluoro-1-[1-(1-phenylcycloheptyl)-4-piperidinyl]-1,3-dihydro-2H-1,3-benzimidazol-2-one as starting material. The two steps yield was 40.9%.

$^1$H NMR (270 MHz, CDCl$_3$) δ 7.54–7.48 (2H, m), 7.40–7.20 (5H, m), 6.88 (1H, dt, J=2.5, 6.2 Hz), 4.10–3.94 (1H, m), 3.28–3.21 (4H, m), 3.05–2.95 (2H, m), 2.66–2.57 (4H, m), 2.37 (3H, s), 2.35–2.00 (8H, m), 1.92–1.42 (10H, m).

This free amine was converted to HCl salt using HCl solution in MeOH to give colorless amorphous solid.

MS m/z(ESI positive): 490(M+H)$^+$. IR(KBr): 3395, 2932, 1622 cm$^{-1}$ Anal. Calcd for C$_{30}$H$_{40}$FN$_5$.3HCl.2.5H$_2$O: C, 55.94; H, 7.51; N, 10.87. Found: C, 56.12; H, 7.60; N, 10.96.

Preparation 8
6Fluoro-1-[1-(1-phenylcycloheptyl)piperidinyl]-1,3dihydro-2H-1,3-benzimidazol-2-one This was prepared according to the procedure described in preparation 4 using 2,4-difluoronitrobenzene instead of 2,6-difluoronitrobenzene. The three step yield from 2,4-difluoronitrobenzene was 45.6%.

$^1$H NMR (270 MHz, CDCl$_3$) δ 9.41 (1H, br.s), 7.55–7.45 (2H, m), 7.38–7.18 (3H, m), 7.03–6.93 (2H, m), 6.75 (1H, ddd, J=2.0, 8.8, 11.2 Hz), 4.274.15 (1H, m), 3.00–2.93 (2H, m), 2.33–2.00 (8H, m), 1.85–1.43 (10H, m). MS m/z(EI direct): 407(M$^+$), 350, 321, 234, 91.

Example 47
6-Fluoro-2-(4-methyl-1-piperazinyl)-1-[1-(1-phenylcycloheptyl)-4-piperidinyl]-1H- benzimidazole This was prepared according to the procedure described in Example 45 using 6-fluoro-1-[1-(1-phenylcycloheptyl)-4-piperidinyl]-1,3-dihydro-2H-1,3-benzimidazol-2-one as starting material. The two steps yield was 15.2%.

$^1$H NMR (270 MHz, CDCl$_3$) δ 7.56–7.47 (3H, m), 7.40–7.16 (4H, m), 6.94–6.84 (1H, m), 4.10–3.96 (1H, m), 3.26–3.18 (4H, m), 3.05–2.96 (2H, m), 2.63–2.57 (4H, m), 2.37 (3H, s), 2.43–2.00 (8H, m), 1.83–1.42 (10H, m).

This free amine was converted to HCl salt using HCl solution in MeOH to give colorless amorphous solid.

MS m/z(ESI positive): 490(M+H)$^+$. IR(KBr): 3402, 2932, 1616, 1458 cm$^{-1}$ Anal. Calcd for C$_{30}$H$_{40}$FN$_5$.3HCl.3H$_2$O: C, 55.17; H, 7.56; N, 10.72. Found: C, 55.47; H, 7.66; N, 10.93.

Example 48
2-(4-Methylpiperazino)-1-[1-(1-phenylcyclohexyl)-4-piperidinyl]-1H-benzimidazole This was prepared according to the procedure described in Example 26 and 4. The two steps yield was 29%.

$^1$H NMR (270 MHz, CDCl$_3$) δ 7.64–7.58 (1H, m), 7.56–7.48 (1H, m), 7.43–7.26 (5H, m), 7.18–7.11 (2H, m), 4.02–3.87 (1H, m), 3.32–3.23 (2H, m), 3.23–3.17 (4H, m), 2.60–2.40 (6H, m), 2.33 (3H, s), 2.25–2.00 (4H, m), 1.90–1.35 (10H, m).

This free amine was converted to hydrochloride salt using HCl solution in MeOH to give amorphous solid.

IR(KBr): 3387, 2937, 1612 cm$^{-1}$ Anal. Calcd for C$_{29}$H$_{39}$N$_5$.3HCl.1.5H$_2$O: C, 58.63; H, 7.63; N, 11.79. Found: C, 58.90; H, 8.00; N, 11.53.

Example 49
N-Methyl-1-[1-(1-methylcyclooctyl)-4-piperidinyl]-1H-benzimidazol-2-amine This was prepared according to the procedure described in Example 41 and 2. The four steps yield was 11.2%.

$^1$H NMR (270 MHz, CDCl$_3$) δ 7.55–7.45 (1H, m), 7.30–7.20 (1H, m), 7.13–6.98 (2H, m), 4.05–3.80 (1H, m), 3.30–3.00 (2H, m), 3.15 (3H, s), 2.60–1.95 (4H, m), 1.95–120 (16H, m), 0.92 (3H, br.s).

This free amine was converted to hydrochloride salt using HCl solution in MeOH to give white amorphous solid.

IR(KBr): 3400, 2930, 1661 cm$^{-1}$ Anal. Calcd for C$_{22}$H$_{34}$N$_4$.2HCl.3H$_2$O: C, 55.75; H, 8.95; N, 11.31. Found: C, 55.62; H, 9.11; N, 11.25.

Example 50
1-{1-[1-(4-Fluorophenyl)cyclononyl]-4-piperidinyl}-1H-benzimidazole This was prepared according to the procedure described in Example 12 using N-1-{1-[1-(4-fluorophenyl)cyclononyl]-4-piperidinyl}-1,2-benzenediamine which was prepared in Example 31. Yield was 88%.

$^1$H NMR (270 MHz, CDCl$_3$) δ 7.99 (1H, s), 7.85–7.77 (1H, m), 7.48–7.24 (5H, m), 7.02 (2H, t, J=8.6 Hz), 4.12–3.98 (1H, m), 3.28–3.12 (2H, m), 2.20–1.90 (8H, m), 1.85–1.24 (14H, m).

This free amine was converted to HCl salt using HCl solution in MeOH to give colorless amorphous solid.

MS(EI) m/z: missing IR(KBr): 3385, 2930, 1605, 1516 cm$^{-1}$ Anal. Calcd for C$_{27}$H$_{34}$FN$_3$.2HCl.2.35H$_2$O.0.05CH$_2$Cl$_2$: C,60.16; H, 7.80; N, 7.78. Found: C, 60.53; H, 7.72; N, 7.38.

Example 51
1-{1-[1-(1-Phenylcycloheptyl)-4-piperidinyl]-1H-benzimidazol-2-yl}-4-piperidinone This was prepared according to the procedure described in Example 27 using 1,4-dioxa-8-azaspiro[4.5]decane instead of t-butyl N-(2-aminoethyl)carbamate. Yield was 79.9%.

$^1$H NMR (270 MHz, CDCl$_3$) δ 7.65–7.58 (1H, m), 7.57–7.49 (3H, m), 7.40–7.30 (2H, m), 7.28–7.15 (3H, m), 4.20–4.05 (1H, m), 3.53 (4H, t, J=5.9 Hz), 3.10–2.98 (2H, m), 2.68 (4H, t, J=5.9 Hz), 2.50–2.00 (8H, m), 1.90–1.40 (10H, m).

This free amine was converted to HCl salt using HCl solution in MeOH to give colorless solid, mp 168–172° C.

MS(EI) m/z: 470(M$^+$), 413, 385, 297, 256, 172, 129, 91. IR(KBr): 3373, 2932, 1717, 1612, 1450 cm$^{-1}$ Anal. Calcd for C$_{30}$H$_{38}$N$_4$O.2HCl.3.2H$_2$O: C, 59.93; H, 7.78; N, 9.32. Found: C, 59.53; H, 7.91; N, 9.34.

Example 52
1-{1-[1-(1-Phenylcycloheptyl)-4piperidinyl]-1H-benzimidazol-2-yl}-4piperidinol To a stirred solution of 1-{1-[1-(1-phenylcycloheptyl)-4-piperidinyl]-1H-benzimidazol-2-yl}-4-piperidinone (Example 51, 162 mg, 0.345 mmol) in MeOH (3 ml) was added NaBH$_4$ (19.7 mg, 0.521 mmol) at 0° C. After 45 min. stirring, the reaction mixture was poured into sat. NH$_4$Cl solution and extracted with CH$_2$Cl$_2$. The extracts combined were washed with brine, dried (Na$_2$SO$_4$), filtered, and concentrated. The residue was purified by preparative TLC (1 mm plate×1, CH$_2$Cl$_2$/MeOH: 95/5) to give 157 mg (96.5%) of colorless solid.

$^1$H NMR (270 MHz, CDCl$_3$) δ 7.63–7.45 (4H, m), 7.40–7.30 (2H, m), 7.26–7.11 (3H, m), 4.13–4.00 (1H, m), 3.95–3.85 (1H, m), 3.428–3.30 (2H, m), 3.10–2.95 (4H, m), 2.45–2.00 (10H, m), 1.90–1.40 (13H, m).

This free amine was converted to HCl salt using HCl solution in MeOH to give colorless solid, mp 208–212° C.

MS(EI) m/z: 472(M$^+$), 415, 387, 299, 255, 2184, 172, 91. IR(KBr): 3400, 2932, 1616, 1447 cm$^{-1}$ Anal. Calcd for C$_{30}$H$_{40}$N$_4$O.2HCl.2H$_2$O: C, 61.95; H, 7.97; N, 9.63. Found: C, 61.57; H, 8.31; N, 9.85.

Example 53
1-{1-[1-(1-Phenylcycloheptyl)-4-piperidinyl]-1H-benzimidazol-2-yl}4-piperidinone oxime A suspension mixture of 1-{1-[1-(1-phenylcycloheptyl)-4-piperidinyl]-1H-benzimidazol-2-yl}-4-piperidinone (Example 51, 136 mg, 0.289 mmol), hydroxylamine hydrochloride (35.1 mg, 0.505 mmol), and sodium acetate (35.9 mg, 0.438 mmol) in EtOH (3 ml) was stirred at room temperature for 0.5 h. The reaction mixture was basified with sat. NaHCO$_3$ solution at 0° C. and extracted with CH$_2$Cl$_2$. The extracts combined were washed with brine, dried (Na$_2$SO$_4$), filtered, and concentrated. The residue was purified by preparative TLC (1 mm plate×1, hexane/acetone:3/2, then 0.5 mm plate×3, CH$_2$Cl$_2$/MeOH: 95/5) to give 104 mg (74.1%) of colorless solid.

$^1$H NMR (270 MHz, CDCl$_3$) δ 7.65–7.48 (4H, m), 7.40–7.30 (2H, m), 7.26–7.13 (3H, m), 4.18–4.04 (1H, m), 3.40–3.25 (4H, m), 3.10–2.98 (2H, m), 2.85 (2H, t, J=5.9 Hz), 2.54 (2H, t, J=5.9 Hz), 2.50–2.00 (8H, m), 1.90–1.40 (10H, m).

This free amine was converted to fumaric acid salt to give colorless solid, mp 201–204° C.

MS(EI) m/z: 485(M$^+$), 428, 312, 231, 91. IR(KBr): 3232, 2932, 1713, 1464 cm$^{-1}$ Anal. Calcd for $C_{30}H_{39}N_5O.C_4H_4I.CH_2Cl_2$: C, 61.22; H, 6.61; N, 10.20. Found: C, 61.62; H, 6.94; N, 10.23.

Example 54
1-{1-[1-(1-Phenylcycloheptyl)-4-piperidinyl]-1H-benzimidazol-2-yl}-4-piperidinylamine To a stirred solution of 1-{1-[1-(1-phenylcycloheptyl)-4-piperidinyl]-1H-benzimidazol 2-yl}-4-piperidinol (Example 52, 106 mg, 0.225 mmol) and triethylamine (0.0623 ml, 0.449 mmol) in $CH_2Cl_2$ was added mesyl chloride at room temperature. After 30 min. stirring, the reaction mixture was diluted with saturated $NaHCO_3$ solution, extracted with $CH_2Cl_2$. The extracts combined were washed with brine, dried ($Na_2SO_4$), filtered, and concentrated. The residue was dissolved in DMF (1 ml) and THF (1 ml). To this solution was added $NaN_3$ (30.7 mg, 0.472 mmol) at room temperature. Then the reaction mixture was refluxed for 3 h. After cool down, the reaction mixture was poured into water and extracted with $Et_2O$. The extracts combined were washed with water, dried ($Na_2SO_4$), filtered, and concentrated. The residue was purified by preparative TLC (1 mm×2 plate, $CH_2Cl_2$/MeOH: 9/1) to give 90 mg(80.6%) of colorless oil. To a stirred suspension of LiAlH4 (35.7 mg, 0.941 mmol) in $Et_2O$ (1 ml) was added a solution of this azide derivative (90 mg, 0.181 mmol) in $Et_2O$ (5 ml) at 0° C. After 3 h stirring at room temperature, the reaction mixture was quenched with $Na_2SO_4$—$10H_2O$. After filtration, the filtrate was concentrated to give 73.5 mg (86.2%) of colorless foam.

$^1$H NMR (270 MHz, $CDCl_3$) δ 7.63–7.45 (4H, m), 7.38–7.31 (2H, m), 7.26–7.11 (3H, m), 4.15–4.00 (1H, m), 3.37–3.31 (2H, m), 3.06–2.88 (5H, m), 2.50–1.40 (24H, m). In order to purify this compound, this crude amine was converted to Boc derivative by treating with $(Boc)_2O$ and DMAP in $CH_2Cl_2$ to afford Boc derivative in 60.6% yield after preparative TLC purification. $^1$H NMR (270 MHz, $CDCl_3$) δ 7.63–7.45 (4H, m), 7.38–7.31 (2H, m), 7.25–7.11 (3H, m), 4.57 (1H, br.s), 4.10–3.96 (1H, m), 3.75–3.61 (1H, m), 3.48 (4H, s), 3.36–3.29 (2H, m), 3.11–2.99 (4H, m), 2.44–2.03 (8H, m), 1.80 –1.54 (10H, m), 1.46 (9H, s).

This Boc derivative (54 mg, 0.0946 mmol) was treated with HCl solution in MeOH (2 ml) at room temperature for 17 h. Evaporation of the solvent gave white solid which was washed with $Et_2O$ and dried in vacuo to afford 25 mg of HCl salt, mp 225–228° C.

MS(ESI positive) m/z: 472(M+H)$^+$. IR(KBr): 3406, 2932, 1618, 1450 cm$^{-1}$ Anal. Calcd for $C_{30}H_{41}N_5.3HCl.3.5H_2O$: C, 55.94; H, 7.98; N, 10.87. Found: C, 55.70; H, 8.202; N, 10.62.

Example 55
N-Methyl-1-[1-(1-methylcycloheptyl)-4-piperidinyl]-1H-benzimidazol-2-amine This was prepared according to the procedure described in Example 28 using cycloheptanone instead of cyclononanone. Overall yield was 19.1%.

$^1$H NMR (270 MHz, $CDCl_3$) δ 7.52–7.46 (1H, m), 7.29–7.22 (1H, m), 7.12–6.98 (2H, m), 4.60–4.42 (1H, m), 4.00–3.80 (1H, m), 3.26–3.16 (2H, m), 3.15 (3H, br.d, J=3.5 Hz), 2.50–1.35 (18H, m), 0.99 (3H, s).

This free amine was converted to HCl salt using HCl solution in MeOH to give colorless amorphous solid.

MS(EI) m/z: 340(M$^+$), 326, 309, 194, 82. IR(KBr): 3406, 2934, 1660 cm$^{-1}$ Anal. Calcd for $C_{21}H_{32}N_4.2HCl.1.5H_2O$: C, 57.27; H, 8.47; N, 12.72. Found: C, 57.26; H, 8.84; N, 12.65.

Example 56
1-[1-(1-Ethylcycloheptyl)-4-piperidinyl]-N-methyl-1H-benzimidazol-2-amine This was prepared according to the procedure described in Example 29 using cycloheptanone instead of cyclononanone. Overall yield was 36%.

$^1$H NMR (270 MHz, $CDCl_3$) δ 7.52–7.47 (1H, m), 7.30–7.25 (1H, m), 7.12–6.98 (2H, m), 4.46–4.30 (1H, m), 3.94–3.76 (1H, m), 3.15 (3H, br.d, J=4.1 Hz), 3.15–3.06 (2H, m), 2.44–2.16 (4H, m), 2.00–1.40 (16H, m), 0.88 (3H, t, J=7.4 Hz).

This free amine was converted to HCl salt using HCl solution in MeOH to give colorless amorphous solid.

MS(EI) m/z: 354(M$^+$), 325, 178. IR(KBr): 3410, 2934, 1661 cm$^{-1}$ Anal. Calcd for $C_{22}H_{34}N_4.2HCl.MeOH.0.5H_2O$: C, 58.56; H, 8.74; N, 12.14. Found: C, 58.94; H,9.08; N, 12.51.

Example 57
N-Methyl-1-[1-(1-propylcycloheptyl)-4-piperidinyl]-1H-benzimidazol-2-amine This was prepared according to the procedure described in Example 28 using cycloheptanone instead of cyclononanone, and propylmagnesium bromide instead of methylmagnesium bromide. Overall yield was 10.6%.

$^1$H NMR (270 MHz, $CDCl_3$) δ 7.55–7.47 (1H, m), 7.32–7.25 (1H, m), 7.14–6.98 (2H, m), 4.30–4.19 (1H, m), 3.90–3.77 (1H, m), 3.20–3.06 (2H, m), 3.15 (3H, br.d, J=4.1 Hz), 2.42–2.20 (4H, m), 1.90–1.28 (18H, m), 0.91 (3H, t, J=6.4 Hz).

This free amine was converted to HCl salt using HCl solution in MeOH to give colorless amorphous solid. MS(EI) m/z: 368(M$^+$), 325, 178. IR(KBr): 3377, 2932, 1661 cm$^{-1}$ Anal. Calcd for $C_{23}H_{36}N_4.2HCl.2.5H_2O.0.5CH_2Cl_2$: C, 53.36; H, 8.38; N, 10.59. Found: C, 53.52; H, 8.34; N, 10.71.

Example 58
N-Methyl-1-[1-(1-propylcyclooctyl)-4-piperidinyl]-1H-benzimidazol-2-amine This was prepared according to the procedure described in Example 57 using cyclooctanone instead of cycloheptanone. Overall yield was 8.9%.

$^1$H NMR (270 MHz, $CDCl_3$) δ 7.53–7.47 (1H, m), 7.31–7.25 (1H, m), 7.13–6.98 (2H, m), 4.254.15 (1H, m), 3.87–3.77 (1H, m), 3.18–3.105 (5H, m), 2.36–2.20 (4H, m), 1.88–1.20 (20H, m), 0.90 (3H, br.t).

This free amine was converted to HCl salt using HCl solution in MeOH to give colorless amorphous solid.

MS(EI) m/z: 382(M$^+$), 339, 192. IR(KBr): 3389, 2934, 1661, 1479 cm$^{-1}$ Anal. Calcd for $C_{24}H_{38}N_4.2HCl.2.5H_2O$: C, 57.59; H, 9.06; N, 11.19. Found: C, 57.45; H, 8.90; N, 10.99.

Example 59
3-{1-[1-(1-Phenylcycloheptyl)-4-piperidinyl]-1H-benzimidazol-2-yl}-propylamine This was prepared according to the procedure described in Example 25 using 3-nitropropionic acid instead of 1-benzylpiperidine-4-carboxylic acid, and Fe, $NH_4Cl$, and aqueous EtOH instead of $H_2$, palladium black, HCl, and MeOH. Overall yield was 30.7%.

This free amine was converted to HCl salt using HCl solution in MeOH to give ivory amorphous solid.

¹H NMR (270 MHz, DMSOd₆) δ 10.98 (1H, br.s), 8.81–8.73 (1H, m), 8.22 (3H, br.s), 7.91–7.74 (3H, m), 7.57–7.40 (5H, m), 5.15–5.00 (1H, m), 3.56–3.10 (8H, 3.02–2.74 (4H, m), 2.60–2.50 (2H, m), 2.20–1.20 (12H, m). IR(KBr): 3406, 2934, 1612, 1466 cm⁻¹ Anal. Calcd for C₂₈H₃₈N₄.2HCl.4.5H₂O: C, 57.53; H, 8.45; N, 9.58. Found: C, 57.71; H, 8.49; N, 9.48.

Example 60
1-[1-(1-Methylcyclooctyl)-4-piperidinyl]-2-(1-piperazinyl)-1H-benzimidazole This was prepared according to the procedure described in Example 18, 19 and 41. Overall yield was 19.7%.

¹H NMR (270 MHz, CDCl₃) δ 7.66–7.60 (1H, m), 7.56–7.50 (1H, m), 7.20–7.12 (2H, m), 4.23–4.08 (1H, m), 3.22–3.04 (10H, m), 2.56–2.38 (2H, m), 2.25–1.30 (19H, m), 0.88 (3H, s).

This free amine was converted to HCl salt using HCl solution in MeOH to give colorless amorphous solid.

MS(EI) m/z: 409 (M⁺), 394, 353, 284, 203, 123, 82. IR(KBr): 3387, 2928, 1630, 1458 cm⁻¹ Anal. Calcd for C₂₅H₃₉N₅.3HCl.2H₂O.MeOH: C, 53.19; H, 8.58; N, 11.93. Found: C, 53.35; H, 8.95; N, 12.07.

Example 61
4-{1-[1-(1-Phenylcycloheptyl)-4-piperidinyl]-1H-benzimidazol-2-yl}-1-piperidinecarboximidamide This was prepared according to the procedure described in Example 33 using Example 25 as a starting material. Overall yield was 68.2%.

¹H NMR (270 MHz, CDCl₃+CD₃OD) δ 7.68–7.63 (2H, m), 7.55–7.50 (2H, m), 7.40–7.20 (5H, m), 4.18–3.96 (3H, m), 3.28–2.90 (6H, m), 2.55–1.95 (14H, m), 1.85–1.45 (10H, m).

This free amine was converted to HCl salt using HCl solution in MeOH to give ivory amorphous solid.

IR(KBr): 3346, 3213, 2932, 1653, 1612, 1465 cm⁻¹ Anal. Calcd for C₃₁H₄₂N₆.2HCl.3H₂O: C, 59.51; H, 8.05; N, 13.43. Found: C, 59.16; H, 8.40; N, 13.18.

Example 62
4-{1-[1-(1-Methylcyclooctyl)-4-piperidinyl]-1H-benzimidazol-2-yl}-1-piperazinecarboximidamide This was prepared according to the procedure described in Example 33 using Example 60 as a starting material. Overall yield was 75%.

This free amine was converted to HCl salt using HCl solution in MeOH to give colorless amorphous solid.

¹H NMR (270 MHz, DMSOd₆) δ 10.75 (2H, br.s), 8.76–8.62 (1H, m), 7.65–7.60 (1H, m), 7.44–7.29 (2H, m), 4.76 4.60 (1H, m), 4.00–3.20 (12H, m), 2.30–2.06 (4H, m), 1.96–1.42 (17H, m), 1.39 (3H, s). MS(ESI positive) m/z: 452(M+H)⁺. IR(KBr): 3356, 2928, 1609, 1452 cm⁻¹ Anal. Calcd for C₂₆H₄₁N₇.2HCl.4.5H₂O: C, 51.56; H, 8.65; N, 16.19. Found: C, 51.30; H, 8.74; N, 15.98.

Example 63
1-[1-(1-Phenylcycloheptyl)-4-piperidinyl]-1H-benzimidazol-2-yl 4-piperidinyl ether To a NaH (60% oil suspension, 42.7 mg, 1.08 mmol, washed 2 times with heptane) was added a solution of 1-benzyl-4-hydroxypiperidine (108 mg, 0.565 mmol) in DMF (1 ml) at 0° C. and the resulting mixture was stirred at room temperature for 30 min. Then a solid of Example 1 (76.9 mg, 0.189 mmol) was added to the reaction mixture at 0° C. and resulting mixture was stirred at room temperature for 16 h. The reaction mixture was poured into water and extracted with EtOAc. The extracts combined were washed with water, dried (Na₂SO₄), filtered, and concentrated. The residue was purified by column chromatography (silica gel: 30 g, hexane/acetone: 3/1) to give 86.4 mg (81.4%) of colorless solid.

¹H NMR (270 MHz, CDCl₃) δ 7.54–7.48 (3H, m), 7.36–7.19 (9H, m), 7.15–7.06 (2H, m), 5.27–5.19 (1H, m), 4.10–3.98 (1H, m), 3.57 (2H, s), 3.01–2.96 (2H, m), 2.75–2.63 (2H, m), 2.52–2.44 (2H, m), 2.37–2.07 (10H, m), 2.03–1.92 (2H, m), 1.82–1.69 (5H, m), 1.58–1.50 (5H, m).

A mixture of this benzylamine derivative (86.4 mg, 0.154 mmol), palladium black (36.4 mg), and 0.2 M HCl solution in MeOH (1 ml) in MeOH (5 ml) was stirred under hydrogen atmosphere at room temperature for 16.5 h. After filtration, the filtrate was basified with NaHCO₃ solution and extracted with CH₂Cl₂. The extracts combined were washed with brine, dried (Na₂SO₄), filtered, and concentrated to give yellow syrup, which was dissolved in CH₂Cl₂ (1 ml). To this solution was added a solution of (BOC)₂ O (65.7 mg, 0.301 mmol) and catalytic amount of DMAP at room temperature. After 21 h stirring, the reaction mixture was poured into NaHCO₃ solution and extracted with CH₂Cl₂. The extracts combined were washed with brine, dried (Na₂SO₄), filtered, and concentrated. The residue was purified by preparative TLC (1 mm plate×2, CH₂Cl₂/MeOH: 95/5) to give 29.3 mg (33.3% for 2 steps) of colorless syrup.

¹H NMR (270 MHz, CDCl₃) δ 7.55–7.48 (3H, m), 7.36–7.18 (4H, m), 7.17–7.08 (2H, m), 5.40–5.33 (1H, m), 4.12–4.01 (1H, m), 3.71–3.61 (2H, m), 3.56–3.46 (2H, m) 3.00–2.96 (2H, m), 2.36–2.18 (4H, m), 2.09–2.01 (4H, m), 1.93–1.46 (14H, m), 1.50 (9H, s). A mixture of this Boc derivative (29.3 mg) and HCl solution in MeOH (1 ml) was stirred at room temperature for 15 h. The reaction mixture was concentrated in vacuo and residue was dried at 45° C. to give 15 mg of title compound as HCl salt, mp 114–118° C.

MS(ESI positive) m/z: 473(M+H)⁺. IR(KBr): 3400, 2934, 1684, 1601, 1474 cm⁻¹ Anal. Calcd for C₃₀H₄₀N₄O.2HCl.4H₂O: C, 58.34; H, 8.16; N, 9.07. Found: C, 58.34; H, 8.19; N, 9.02.

Example 64
N-1-{1-[1-(1-Phenylcycloheptyl)-4-piperidinyl]-1H-benzimidazol-2-yl}-1,6-hexanediamine This was prepared according to the procedure described in Example 20 using 1,6-hexanediamine instead of amylamine. Yield was 80.4%.

¹H NMR (270 MHz, CDCl₃) δ 7.51–7.44 (2H, m), 7.37–7.20 (5H, m), 7.10–6.97 (2H, m), 4.25–4.19 (1H, m), 3.82–3.70 (1H, m), 3.55–3.47 (2H, m), 3.03–2.99 (2H, m), 2.72–2.66 (2H, m), 2.33–2.09 (8H, m), 1.81–1.64 (10H, m), 1.58–1.39 (10H, m).

This free amine was converted to HCl salt using HCl solution in MeOH to give colorless solid, mp 165–168° C.

MS(ESI positive) m/z: 488(M+H)⁺. IR(KBr): 3385, 2935, 2860, 1650, 1480, 1635 cm⁻¹ Anal. Calcd for C₃₁H₄₅N₅.3HCl.2.5H₂O: C, 57.98; H, 8.32; N, 10.91. Found: C, 58.14; H, 8.67; N, 10.88.

Example 65
1-1-{1-[1-(1-Phenylcycloheptyl)-4-piperidinyl]-1H-benzimidazol-2-yl}-3-azetidinylamine This was prepared according to the procedure described in Example 27 using 4-t-butoxycarbonylaminoazetidine (this was reported in EP 106489) instead of t-butyl N-(2-aminoethyl)carbamate. Yield was 47.3%.

MS(ESI positive) rn/z: 448(M+H)⁺. IR(KBr): 3402, 2932, 1647, 1466 cm⁻¹ Anal. Calcd for C₂₈H₃₇N₅.3HCl.3H₂O: C, 55.40; H, 7.64; N, 11.54. Found: C, 55.49; H, 7.92; N, 11.40.

Example 66
N-1-{1-[1-(1-Phenylcycloheptyl)-4-piperidinyl]-1H-benzimidazol-2-yl}-1,4-butanediamine This was prepared according to the procedure described in Example 20 using 1,4-butanediamine instead of amylamine. Yield was 43.7%.

$^1$H NMR (270 MHz, CDCl$_3$) δ 7.50–7.42 (3H, m), 7.37–7.19 (4H, m), 7.09–6.96 (2H, m), 3.87–3.76 (1H, m), 3.54–3.48 (2H, m), 3.00–2.96 (2H, m), 2.83–2.77 (2H, m) 2.33–2.02 (12H, m), 1.82–1.47 (12H, m).

This free amine was converted to HCl salt using HCl solution in MeOH to give colorless solid, mp 213–217° C.

MS(ESI positive) m/z: 460(M+H)$^+$. IR(KBr): 3404, 2934, 1655, 1479 cm$^{-1}$ Anal. Calcd for C$_{29}$H$_{41}$N$_5$.3HCl.3H$_2$O: C, 55.90; H, 8.09; N, 11.24. Found: C, 55.96; H, 8.40; N, 11.03.

Example 67
1-{1-[1-(1-Methylcycloheptyl)-4-piperidinyl]-1H-benzimidazol-2-yl}-4-piperidinylamine This was prepared according to the procedure described in Example 27 using 4-t-butoxycarbonylaminopiperidine instead of t-butyl N-(2-aminoethyl)carbamate, and 2-chloro-1-[1-(1-methylcycloheptyl)-4-piperidinyl]benzimidazole as a starting material which was prepared in Example 55. Overall yield was 26.6%. p $^1$H NMR (270 MHz, CDCl$_3$) δ 7.64–7.48 (2H, m), 7.19–7.10 (2H, m), 4.21–4.06 (1H, m), 3.44–3.34 (2H, m), 3.22–2.84 (5H, m), 2.58–2.35 (2H, m), 2.27–2.15 (2H, m), 2.05–1.35 (20H, m), 0.97 (3H, s).

This free amine was converted to HCl salt using HCl solution in MeOH to give yellow amorphous solid.

IR(KBr): 3387, 2934, 1612, 1477 cm$^{-1}$ Anal. Calcd for C$_{25}$H$_{39}$N$_5$.2HCl.3H$_2$O.MeOH: C, 54.92; H, 9.04; N, 12.32. Found: C, 54.85; H, 9.30; N, 12.27.

Preparation 9
N-1-[1-(1-Methylcycloheptyl)-4-piperidinyl]-1,2-benzenediamine This was prepared according to the procedure described in Preparation 1 using methylmagnesium bromide instead of phenylmagnesium bromide, and Zn, NH$_4$Cl, and aqueous MeOH instead of SnCl$_2$—2H$_2$O and EtOH. Overall yield was 22.6%.

$^1$H NMR (270 MHz, DMSOd$_6$) δ 6.83–6.61 (4H, m), 3.30 (3H, br.s), 3.28–3.14 (1H, m), 2.98–2.87 (2H, m), 2.30–2.18 (2H, m), 2.11–2.00 (2H, m), 1.90–1.78 (2H, m), 1.70–1.28 (12H, m), 0.93 (3H, s).

MS(EI) m/z: 301(M$^+$), 286, 244, 194, 161, 119, 82.

Example 68
1-[1-(1-Methylcycloheptyl)-4-piperidinyl]-2-(4-piperidinyl)-1H-benzimidazole This was prepared according to the procedure described in Example 25 using N-1-[1-(1-methylcycloheptyl)-4-piperidinyl]-1,2-benzenediamine as a starting material. Overall yield was 11.8%.

$^1$H NMR (270 MHz, CDCl$_3$) δ 7.79–7.72 (1H, m), 7.65–7.59 (1H, m), 7.24–7.17 (2H, m), 4.26–4.11 (1H, m), 3.33–3.15 (4H, m), 3.08–2.95 (1H, m), 2.90–2.76 (2H, m), 2.63–2.47 (2H, m), 2.33–2.20 (2H, m), 2.07–1.35 (19H, m), 0.98 (3H, s).

This free amine was converted to HCl salt using HCl solution in MeOH to give pale yellow amorphous solid.

MS(EI) m/z: 394(M$^+$), 338, 283, 202, 84. IR(KBr): 3318, 2934, 1626, 1477 cm$^{-1}$ Anal. Calcd for C$_{25}$H$_{38}$N$_4$.2HCl.4.5H$_2$O: C, 54.74; H, 9.00; N, 10.21. Found: C, 54.84; H, 9.34; N, 10.14.

Example 69
1-[1-(1-Isopropylcycloheptyl)-4-piperidinyl]-2-(1-piperazinyl)-1H-benzimidazole This was prepared according to the procedure described in Example 60 using isopropylmagnesium bromide instead of methylmagnesium bromide, and cycloheptanone instead of cyclooctanone. Overall yield from 2-chloro-1-[1-(1-isopropylcycloheptyl)-4-piperidinyl]benzimidazole was 26.5%.

$^1$H NMR (270 MHz, CDCl$_3$) δ 7.66–7.60 (1H, m), 7.52–7.44 (1H, m), 7.20–7.10 (2H, m), 4.26–4.11 (1H, m), 3.32–3.16 (6H, m), 3.12–3.05 (4H, m), 2.56–2.32 (4H, m), 2.02–1.44 (17H, m), 0.90 (6H, d, J=6.9 Hz).

This free amine was converted to HCl salt using HCl solution in MeOH to give colorless amorphous solid. MS(EI) m/z: 423(M$^+$), 380, 178. IR(KBr): 3387, 2930, 1593, 1458 cm$^{-1}$ Anal. Calcd for C$_{26}$H$_{41}$N$_5$.3HCl.H$_2$O.0.4CH$_2$Cl$_2$: C, 54.20; H, 8.06; N, 11.97. Found: C, 60.29; H, 7.62; N, 10.19.

Example 70
2-Amino-N-{1-[1-(1-phenylcycloheptyl)-4-piperidinyl]-1H-benzimidazol-2-yl}acetamide A mixture of Example 10 (1470 mg, 3.79 mmol), Boc-glycine (1330 mg, 7.58 mmol), and WSC (1450 mg, 7.58 mmol) in CH$_2$Cl$_2$ (20 ml) was stirred at room temperature for 16 h. 25% NH$_4$OH solution was added to the reaction mixture and extracted with CH$_2$Cl$_2$. The extracts combined were washed with brine, dried (Na$_2$SO$_4$), filtered, and concentrated to give brown amorphous solid, which was purified by column chromatography (silica gel: 100 g, hexane/acetone: 1/4 then CH$_2$Cl$_2$/MeOH: 50/1) to give 1,59 g (77%) of pale brown solid.

$^1$H NMR (270 MHz, CDCl$_3$) δ 7.55–7.48 (4H, m), 7.38–7.30 (2H, m), 7.27–7.17 (3H, m), 5.37 (1H, br.s), 4.76–4.54 (2H, m), 4.01 (2H, d, J=5.1 Hz), 3.03–2.90 (2H, m), 2.40–2.00 (8H, m), 1.86–1.40 (10H, m), 1.48 (9H, s).

A mixture of this Boc derivative (1590 mg, 2.92 mmol) and HCl solution in MeOH (50 ml) was stirred at room temperature for 16 h. After evaporation of the solvent, the residue was dissolved in CH$_2$Cl$_2$ and basified with 25% NH$_4$OH solution. Organic layer was separated, washed with brine, dried (Na$_2$SO$_4$), filtered, and concentrated. The residue was purified by column chromatography (silica gel: 65 g, CH$_2$Cl$_2$/MeOH: 30/1) to give 990 mg (76%) of ivory amorphous solid.

$^1$H NMR (270 MHz, CDCl$_3$) δ 7.54–7.48 (4H, m), 7.38–7.19 (6H, m), 4.75–4.60 (1H, m), 3.55 (2H, s), 3.02–2.93 (2H, m), 2.38–2.00 (8H, m), 1.84–1.44 (12H, m). MS(EI) m/z: 445 (M$^+$), 401, 273, 229, 191, 146, 118, 91.

This free amine was converted to HCl salt using HCl solution in MeOH to give pale yellow amorphous solid.

IR(KBr): 3389, 2932, 1744, 1626, 1585, 1475 cm$^{-1}$ Anal. Calcd for C$_{27}$H$_{35}$N$_5$O.2HCl.1.5H$_2$O: C, 59.44; H, 7.39; N, 12.84. Found: C, 59.44; H, 7.33; N, 12.62.

Example 71
2-({1-[1-(1-Phenylcycloheptyl)-4-piperidinyl]-1H-benzimidazol-2-yl}oxy)-1-ethanamine To a stirred suspension of NaH (60% oil suspension, 168 mg, 4.2 mmol, washed with heptane) in DMF (0.5 ml) was added ethylene glycol at 0° C. After 20 min. stirring at room temperature, a solid of Example 1 (290 mg, 0.713 mmol) was added to the reaction mixture and resulting mixture was stirred at 70° C. for 4.5 h. After cool down to 0° C., water was added and extracted EtOAc. The extracts combined were washed with water, dried (Na$_2$SO$_4$), filtered, and concentrated. The residue was purified by column chromatography (silica gel: 40 g, hexane/acetone: 3/1) followed by preparative TLC (1 mm plate×3, hexane/acetone: 3/2) to give 123 mg (39.9%) of colorless amorphous solid.

$^1$H NMR (270 MHz, CDCl$_3$) δ 7.52–7.45 (2H, m), 7.38–7.08 (7H, m), 4.65 (2H, t, J=4.1 Hz), 4.20–4.05 (1H, m), 4.01 (2H, t, J=4.1 Hz), 3.01–2.94 (2H, m), 2.30–2.00 (8H, m), 1.90–1.40 (10H, m).

A mixture of this alcohol derivative (123 mg, 0.284 mmol), MsCl (0.044 ml, 0.568 mmol), and NEt$_3$ (0.0788 ml, 0.568 mmol) in CH$_2$Cl$_2$ (2.5 ml) was stirred at room temperature for 45 min. The reaction mixture was diluted with NaHCO$_3$ solution, extracted with CH$_2$Cl$_2$. The extracts combined were washed with brine, dried (Na$_2$SO$_4$), filtered, and concentrated to give 153 mg of colorless syrup. To a solution of this mesylate derivative (153 mg) in DMF (2 ml) and water (0.5 ml) was added NaN$_3$ (40.9 mg, 0.629 mmol) and the resulting mixture was stirred at 60° C. for 18.5 h. After cool down to room temperature, the reaction mixture was diluted with water and extracted with Et$_2$O. The extracts combined were washed with water, dried (Na$_2$SO$_4$), filtered, and concentrated. The residue was purified by preparative TLC (1 mm plate×2, hexane/acetone: 7/3) to give 107 mg (82.2% for 2 steps) of colorless syrup.

$^1$H NMR (270 MHz, CDCl$_3$) δ 7.60–7.45 (2H, m), 7.45–7.00 (7H, m), 4.35–4.10 (1H, m), 4.01 (2H, t, J=5.9 Hz), 3.46 (2H, t, J=5.9 Hz), 3.10–2.85 (2H, m), 2.40–1.95 (8H, m), 2.90–1.40 (10H, m).

A mixture of this azide derivative (83.2 mg, 0.182 mmol) and palladium black (31 mg) in MeOH (2 ml) and THF (0.5 ml) was stirred under hydrogen atmosphere at room temperature for 3 h. After filtration, the filtrate was concentrated to give 85.3 mg of colorless foam, which was dissolved in CH$_2$Cl$_2$ (2 ml). To this solution was added (Boc)$_2$O (103 mg, 0.472 mmol) and catalytic amount of DMAP at room temperature. After 1 h stirring, the reaction mixture was poured into NaHCO$_3$ solution and extracted with CH$_2$Cl$_2$. The extracts combined were washed with brine, dried (Na$_2$SO$_4$), filtered, and concentrated. The residue was purified by preparative TLC (1 mm plate×2, CH$_2$Cl$_2$/MeOH: 95/5×2 developed) to give 46.6 mg (44.4%) of colorless foam.

$^1$H NMR (270 MHz, CDCl$_3$) δ 7.53–7.49 (3H, m), 7.37–7.29 (2H, m), 7.26–7.05 (4H, m), 4.97–4.90 (1H, m), 4.61–4.56 (1H, m), 4.28–4.19 (1H, m), 4.02–3.96 (1H, m), 3.65–3.59 (1H, m), 3.48–3.43 (1H, m), 2.99–2.93 (2H, m), 2.29–2.17 (4H, m), 2.10–2.05 (4H, m), 1.83–1.70 (5H, m), 1.57–1.48 (5H, m), 1.45–1.41 (9H, m).

A mixture of this Boc derivative (46.6 mg) and HCl solution in MeOH (1 ml) was stirred at room temperature for 11 h. The reaction mixture was concentrated in vacuo and residue was dried at 45° C. to give 40 mg of title compound as HCl salt, mp 180–184° C.

MS(ESI positive) m/z: 433(M+H)$^+$. IR(KBr): 3400, 2930, 2860, 1690, 1605, 1490 cm$^{-1}$ Anal. Calcd for C$_{27}$H$_{36}$N$_4$O.2HCl.2H$_2$O: C, 59.88; H, 7.82; N, 10.35. Found: C, 59.64; H, 7.98; N, 10.09.

Preparation 10
2-Chloro-1-[1-(1-phenyl-4-cyclohepten-1-yl)-4-piperidinyl] benzimidazole This was prepared according to the procedure described in Example 1 using 4-cycloheptenone instead of cycloheptanone. Overall yield was 21.2%.

$^1$H NMR (270 MHz, CDCl$_3$) δ 7.69–7.65 (1H, m), 7.59–7.55 (1H, m), 7.46–7.34 (4H, m), 7.27–7.20 (3H, m), 5.74 (2H, t, J=3.0 Hz), 4.35–4.25 (1H, m), 3.35–3.20 (2H, m), 2.50–2.22 (8H, m), 2.15–1.80 (6H, m).

Example 72
1-{1-[1-(1-Phenyl-4-cyclohepten-1-yl)-4-piperidinyl]-1H-benzimidazol-2-yl)-4-piperidinamine This was prepared according to the procedure described in Example 67 using 2-chloro-1-[1-(1-phenyl-4-cyclohepten-1-yl)-4-piperidinyl]benzimidazole as starting material. Overall yield was 49%.

HCl salt was amorphous solid. $^1$H NMR (270 MHz, DMSOd$_6$) δ 8.68 (1H, br.s), 8.65 (1H, br.s), 8.34 (3H, br.s), 7.90–7.75 (2H, m), 7.60–7.45 (5H, m), 7.40–7.20 (2H, m), 5.78–5.70 (2H, m), 4.45–4.30 (1H, m), 3.80–2.80 (13H, m), 2.65–2.40 (4H, m), 2.15–1.70 (8H, m). MS(EI) m/z: 469 (M$^+$), 392, 370, 299, 253, 217, 170, 142. IR(KBr): 3400, 2939, 1618, 1499 cm$^{-1}$ Anal. Calcd for C$_{30}$H$_{39}$N$_5$.3HCl.6H$_2$O: C, 52.44; H, 7.92; N, 10.19. Found: C, 52.71; H, 7.66; N, 10.06.

Example 73
N-1-{1-[1-(1-Phenylcycloheptyl)-4-piperidinyl]-1H-benzimidazol-2-yl}-1,8-octanediamine This was prepared according to the procedure described in Example 20 using 1,8-octanediamine instead of amylamine. Yield was 57%.

$^1$H NMR (270 MHz, CDCl$_3$) δ 7.51–7.44 (3H, m), 7.37–7.19 (4H, m), 7.10–6.97 (2H, m), 4.28–4.22 (1H, m), 3.82–3.70 (1H, m), 3.51–3.46 (2H, m), 3.02–2.98 (2H, m), 2.71–2.65 (2H, m), 2.33–1.96 (12H, m), 1.74–1.63 (4H, m), 1.54–1.25 (16H, m).

This free amine was converted to HCl salt using HCl solution in MeOH to give colorless solid, mp 179–182° C.

MS(ESI positive) m/z: 516(M+H)$^+$. IR(KBr): 3400, 2934, 1653, 1479 cm$^{-1}$ Anal. Calcd for C$_{33}$H$_{49}$N$_5$.3HCl.2H$_2$O: C, 59.95; H, 8.54; N, 10.59. Found: C, 59.55; H, 8.89; N, 10.39.

Example 74
N-1-{1-[1-(1-Phenylcycloheptyl)-4-piperidinyl]-1H-benzimidazol-2-yl}-1,10-decanediamine This was prepared according to the procedure described in Example 20 using 1,10-decanediamine instead of amylamine. Yield was 61.5%.

$^1$H NMR (270 MHz, CDCl$_3$) δ 7.51–7.44 (3H, m), 7.37–7.30 (2H, m), 7.28–7.19 (2H, m), 7.10–6.97 (2H, m), 4.18–4.14 (1H, m), 3.82–3.71 (1H, m), 3.55–3.46 (2H, m), 3.03–2.98 (2H, m), 2.70–2.64 (2H, m), 2.32–2.09 (8H, m), 1.77–1.26 (28H, m).

This free amine was converted to HCl salt using HCl solution in MeOH to give colorless solid, mp 165–168° C.

MS(ESI positive) m/z: 544(M+H)$^+$. IR(KBr): 3416, 2930, 1653, 1468 cm$^{-1}$ Anal. Calcd for C$_{35}$H$_{53}$N$_5$.3HCl.2.4H$_2$O: C, 60.36; H, 8.80; N, 10.06. Found: C, 60.66; H, 9.22; N, 9.92.

Example 75
1-{1-[1-(1-Isopropylcycloheptyl)-4-piperidinyl]-1H-benzimidazol-2-yl}-4-piperidinamine This was prepared according to the procedure described in Example 67 using 2-chloro-1-[1(1-isopropylcycloheptyl)-4-piperidinyl]benzimildazole as starting material which was prepared in Example 69. Overall yield from 2-chloro-1-[1-(1-isopropylcycloheptyl)-4-piperidinyl]benzimidazole was 72%.

This free amine was converted to HCl salt using HCl solution in MeOH to give colorless amorphous solid.

$^1$H NMR (270 MHz, CDCl$_3$) δ 8.78 (1H, br.s), 8.65 (1H, br.s), 8.40 (3H, br.s), 8.35–8.25 (1H, m), 7.63–7.55 (1H, m), 7.45–7.28 (2H, m), 4.57–4.42 (1H, m), 3.33–3.10 (10H, m), 2.40–1.80 (14H, m), 1.65–1.42 (6H, m), 1.10 (6H, d, J=6.8 Hz).

MS(ESI positive) m/z: 438(M+H)$^+$. IR(KBr): 3364, 2934, 1634, 1616, 1475 cm$^{-1}$ Anal. Calcd for $C_{27}H_{43}N_5 \cdot 3HCl \cdot 5H_2O$: C, 50.90; H. 8.86; N, 10.99. Found: C, 50.71; H, 8.79; N, 10.85.

Example 76
N-N-{1-[1-(1-Phenylcycloheptyl)-4-piperidinyl]-1H-benzimidazol-2-yl}-1,4-cyclohexanediamine This was prepared according to the procedure described in Example 34 using 4-(t-butoxycarbonylamino)cyclohexyl isothiocyanate (this was reported by J. Smith et al. *J Org. Chem.* 1996, 61, 8811–8818) instead of ethyl 4-isothiocyanato-1-piperidinecarboxylate. Overall yield from N-1-[1-(1-phenylcycloheptyl)-4-piperidinyl]-1,2-benzenediamine was 5.4%. $^1$H NMR data of Boc derivative was as follows.

$^1$H NMR (270 MHz, CDCl$_3$) δ 7.52–7.22 (7H, m), 7.11–6.99 (2H, m), 4.48–4.43 (1H, m), 4.09–4.01 (1H, m), 3.93–3.78 (2H, m), 3.69–3.61 (1H, m), 3.49–3.39 (1H, m), 3.06–3.02 (2H, m), 2.29–1.99 (11H, m), 1.78–1.73 (5H, m), 1.62–1.53 (5H, m), 1.47–1.44 (9H, m), 1.37–1.20 (4H, m). HCl salt, mp 242–246° C.

MS(ESI positive) m/z: 486(M+H)$^+$. IR(KBr): 3400, 2937, 1647, 1479 cm$^{-1}$ Anal. Calcd for $C_{31}H_{43}N_5 \cdot 3HCl \cdot 1.2CH_2Cl_2$: C, 55.49; H, 7.00; N, 10.05. Found: C, 55.07; H, 7.06; N, 10.41.

Preparation 11
2-Chloro-1-[1-(1-vinylcycloheptyl)-4-piperidinyl]benzimidazole This was prepared according to the procedure described in Example 1 using vinylmagnesium bromide instead of phenylmagnesium bromide. Overall yield was 15.3%.

$^1$H NMR (270 MHz, CDCl$_3$) δ 7.72–7.56 (2H, m), 7.30–7.20 (2H, m), 5.78 (1H, dd, J=10.9, 17.6 Hz), 5.13 (1H, d, J=10.9 Hz), 5.05 (1H, d, J=17.6 Hz), 4.48–4.32 (1H, m), 3.24–3.14 (2H, m), 2.55–2.36 (2H, m), 2.32–2.18 (2H, m), 2.00–1.80 (4H, m), 1.74–1.40 (10H, m).

Example 77
1-{1-[1-(1-Vinylcycloheptyl)-4-piperidinyl]-1H-benzimidazol-2-yl}4-piperidinylamine This was prepared according to the procedure described in Example 67 using 2-chloro-1-[1-(1-vinylcycloheptyl)-4-piperidinyl]benzimidazole as starting material. Overall yield from 2-chloro-1-[1-(1-vinylcycloheptyl)-4-piperidinyl]benzimidazole was 36.1%.

This free amine was converted to HCl salt using HCl solution in MeOH to give colorless amorphous solid.

$^1$H NMR (270 MHz, CDCl$_3$) δ 11.10 (1H, br.s), 8.60–8.50 (1H, m), 8.35 (3H, br.s), 7.62–7.55 (1H, m), 7.40–7.25 (2H, m), 6.10 (1H, dd, J=11.2, 17.5 Hz), 5.61 (1H, d, J=11.2 Hz), 5.51 (1H, d, J=17.5 Hz), 4.55–4.40 (1H, m), 3.75–3.00 (9H, m), 2.28–1.35 (20H, m).

MS(ESI positive) m/z: 422(M+H)$^+$. IR(KBr): 3400, 2926, 1633, 1616, 1456 cm$^{-1}$ Anal. Calcd for $C_{26}H_{39}N_5 \cdot 3HCl \cdot 3H_2O \cdot 0.9CH_2Cl_2$: C, 48.84; H, 7.59; N, 10.59. Found: C, 48.61; H, 7.95; N, 10.74.

Example 78
2-Methyl-N-1-{1-[1-(1-phenylcycloheptyl)piperidinyl]-1H-benzimidazol2yl}-1,2-propanediamine This was prepared according to the procedure described in Example 20 using 1,2-diamino-2-methylpropane instead of amylamine. Yield was 26.2%.

$^1$H NMR (270 MHz, CDCl$_3$) δ 7.52–7.41 (3H, m), 7.35–7.18 (4H, m), 7.09–6.97 (2H, m), 3.98–3.87 (1H, m), 3.47 (1H, s), 3.43 (1H, s), 3.02–2.98 (2H, m), 2.34–2.20 (4H, m), 2.11–2.01 (4H, m), 1.81–1.71 (5H, m), 1.59–1.45 (5H, m), 1.24 (6H, s).

This free amine was converted to HCl salt using HCl solution in MeOH to give colorless solid, 230–234° C.

MS(ESI positive) m/z: 460(M+H)$^+$. IR(KBr): 3406, 2934, 1649, 1479 cm$^{-1}$ Anal. Calcd for $C_{29}H_{41}N_5 \cdot 3HCl \cdot 2.5H_2O$: C, 56.72; H, 8.04; N, 11.40. Found: C, 56.43; H, 8.35; N, 11.26.

Example 79
1-[1-(1-Phenylcyclohepten-1-yl)-4-piperidinyl]-2-(1-piperazinyl)-1H-benzimidazole This was prepared according to the procedure described in Example 67 using 1-N-t-butoxycarbonylpiperazine instead of 4-t-butoxycarbonylaminopiperidine, and 2-chloro-1-[1-(1-phenyl-4-cyclohepten-1-yl)-4-piperidinyl]benzimidazole as starting material which was prepared in Preparation 9. Overall yield was 40.3%. HCl salt was amorphous solid.

$^1$H NMR (270 MHz, DMSOd$_6$) δ 11.07 (1H, br.s), 9.61 (3H, br.s), 8.65 (1H, d, J=7.9 Hz), 7.83–7.75 (2H, m), 7.62–7.50 (4H, m), 7.38–7.24 (2H, m), 5.77–5.72 (2H, m), 4.53–4.43 (1H, m), 3.75–2.85 (16H, m), 2.65–2.45 (4H, m), 2.15–1.80 (4H, m).

MS(EI) m/z: 455(M$^+$), 399, 331, 284, 252, 203, 184, 134. IR(KBr): 3400, 2920, 1650, 1456 cm$^{-1}$ Anal. Calcd for $C_{29}H_{37}N_5 \cdot 3HCl \cdot 4H_2O$: C, 54.67; H, 7.59; N, 10.99. Found: C, 54.44H, 8.09; N, 11.10.

Example 80
3-({1-[1-(1-Phenylcycloheptyl)-4-piperidinyl]-1H-benzimidazol-2-yl}sulfonyl)1-propanamine A solution of 1-[1-(1-phenylcycloheptyl)-4-piperidinyl]phenylene-1,2-diamine (prepared in Preparation 1, 114 mg, 0.314 mmol) and carbon disulfide (0.0944 ml) in EtOH (3 ml) was refluxed for 2 h. After cool down to room temperature, the reaction mixture was poured into water and extracted with $CH_2Cl_2$. The extracts combined were washed with brine, dried (Na$_2$SO$_4$), filtered, and concentrated. The residue was purified by preparative TLC (1 mm plate×2, $CH_2Cl_2$/MeOH: 15/1) give 96.9 mg (76.2%) of brown solid. A mixture of this solid (96.9 mg, 0.239 mmol), 3-t-butoxycarbonylaminopropyl bromide (84.8 mg), solution of NaOH (29.2 mg) in water (1 ml), and EtOH (3 ml) was refluxed for 1 h. After cool down to room temperature, the reaction mixture was diluted with water and extracted with $CH_2Cl_2$. The extracts combined were washed with brine, dried (Na$_2$SO$_4$), filtered, and concentrated. The residue was purified by preparative TLC (1 mm plate×2, hexane/acetone: 7/3) give 102 mg (75.9%) of colorless foam.

$^1$H NMR (270 MHz, CDCl$_3$) δ 7.66–7.62 (1H, m), 7.53–7.50 (3H, m), 7.38–7.31 (2H, m), 7.23–7.15 (2H, m), 6.14–6.04 (1H, m), 4.17–4.04 (1H, m), 3.46–3.40 (2H, m) 3.21 (2H, m), 3.03–2.99 (2H, m), 2.42–2.24 (4H, m), 2.21–2.10 (4H, m), 2.01–1.19 (2H, m), 1.78–1.71 (5H, m), 1.59–1.42 (5H, m), 1.47 (9H, s).

To a stirred solution of this Boc derivative (58.9 mg, 0.105 mmol) in AcOH (0.5 ml) was added a solution of KMnO$_4$ (38.1 mg, 0.241 mmol) in water (4 ml) at 0° C. After 2 h stirring at room temperature, the reaction mixture was diluted with saturated NaHSO$_4$ solution at 0° C. and basified with 25% NH$_4$OH solution. The reaction mixture was extracted with EtOAc. The extracts combined were with brine, dried (Na$_2$SO$_4$), filtered, and concentrated. The residue was purified by preparative TLC (0.5 mm plate×2, hexane/acetone: 4/1) give 16.2 mg (26%) of colorless syrup.

$^1$H NMR (270 MHz, CDCl$_3$) δ 7.84–7.72 (2H, m), 7.54–7.50 (2H, m), 7.45–7.31 (3H, m), 7.27–7.20 (2H, m), 5.24–5.16 (1H, m), 5.03–4.93 (1H, m), 3.83–3.76 (2H, m), 3.37–3.29 (2H, m), 3.02–2.98 (2H, m), 2.44–2.27 (4H, m), 2.26–2.17 (2H, m), 2.15–2.04 (2H, m), 1.96–1.93 (2H, m), 1.79–1.69 (3H, m), 1.61–1.53 (3H, m), 1.46 (9H, s).

A solution of this Boc derivative (16.2 mg)and HCl solution in MeOH (1 ml) in $CH_2Cl_2$ (1 ml) was stirred at room temperature for 18 h. The reaction mixture was concentrated in vacuo and the residue was dried at 45° C. to give 10 mg of title compound as HCl salt.

MS(ESI positive) m/z: 495(M+H)$^+$. IR(KBr): 3400, 2934, 1690, 1485, 1387 cm$^{-1}$ Anal. Calcd for $C_{28}H_{38}N_4O.2HCl.4H_2O$: C, 52.57; H, 7.56; N, 8.76. Found: C, 52.20; H, 7.51; N, 8.59.

Example 81
1-[1-(1-Phenylcyclooctyl)-4-piperidinyl]-1H-benzimidazol-2-amine

This was prepared according to the procedure described in Preparation 4 and Example 31 using cyclooctanone instead of cyclononanone, and phenylmagnesium bromide instead of 4-fluorophenylmagnesium bromide. Overall yield from cyclooctanone was 8.6%.

$^1$H NMR (270 MHz, CDCl$_3$) δ 7.46–7.20 (7H, m), 7.13–7.01 (2H, m), 3.88–3.75 (1H, m), 3.21–3.15 (2H, m), 2.37–1.95 (8H, m), 1.80–1.35 (14H, m).

This free amine was converted to HCl salt using HCl solution in MeOH to give colorless amorphous solid.

MS(EI) m/z: 434(M$^+$), 349, 321, 216, 134, 109, 82. IR(KBr): 3350, 1670 cm$^{-1}$ Anal. Calcd for $C_{27}H_{35}FN_4.2HCl.1.7H_2O$: C,60.26; H, 7.57; N, 10.41. Found: C, 60.29; H, 7.62; N, 10.19.

Example 82
2-Amino-N-{1-[1-(1-phenylcyclooctyl)-4-piperidinyl]-1H-benzimidazol-2-yl}acetamide This was prepared according to the procedure described in Example 70 using 1-[1-(1-phenylcyclooctyl)-4-piperidinyl]-1H-benzimidazol-2-amine. Overall yield was 49.6%.

$^1$H NMR (270 MHz, CDCl$_3$) δ 7.55–7.15 (1H, m), 4.70–4.50 (1H, m), 3.53 (2H, s), 3.47 (2H, s), 3.22–3.10 (2H, m), 2.45–2.00 (8H, m), 1.85–1.30 (12H, m).

This free amine was converted to HCl salt using HCl solution in MEOH to give colorless solid, mp 217–221° C.

MS(ESI positive) m/z: 403(M+H)$^+$. IR(KBr): 3387, 2922, 1742, 1553, 1475 cm$^1$ Anal. Calcd for $C_{28}H_{37}N_5O.2HCl.0.7CH_2Cl_2$: C, 58.23; H, 6.88; N, 11.83. Found: C, 58.22; H, 6.57; N, 11.95.

Example 83
(2S,3S)-2-Amino-3-methyl-N-{1-[1-(1-methylcycloheptyl)-4-piperidinyl]-1H-benzimidazol-2-yl}pentanamide This was prepared according to the procedure described in Example 10 and 70 using N-1-[1-(1-methylcycloheptyl)-4-piperidinyl]-1,2-benzenediamine as a starting material which was prepared in Preparation 8, and Boc-L-isoleucine. Trifluoroacetic acid and $CH_2Cl_2$ was used for deprotection reaction instead of HCl and MeOH. Overall yield was 33.1%. Finally trifluoroacetic acid salt was converted to HCl salt using HCl and MeOH.

HCl salt was amorphous solid. $^1$H NMR (270 MHz, DMSOd$_6$) δ 10.74 (1H, br.s), 8.38 (3H, br.s), 8.25–8.10 (1H, m), 7.63–7.53 (1H, m), 7.32–7.23 (2H, m), 5.46–5.33 (1H, m), 3.75–3.60 (3H, m), 3.35–3.10 (4H, m), 2.30–1.20 (18H, m), 1.50 (3H, s), 1.00 (3H, d, J=6.9 Hz), 0.92 (3H, t, J=7.3 Hz).

MS(EI) m/z: 439(M$^+$), 424, 395, 382, 353, 328, 285, 247, 193, 136. IR(KBr): 3387, 2934, 1734, 1626, 1578 cm$^{-1}$ Anal. Calcd for $C_{26}H_{41}N_5O.2HCl.5.5H_2O$: C, 51.06; H, 8.90; N, 11.45. Found: C, 51.06; H, 8.41; N, 11.25.

Example 84
3-Amino-N-{1-[1-(1-phenylcycloheptyl)-4-piperidinyl]-1H-benzimidazol-2-yl}propanamide This was prepared according to the procedure described in Example 83 using 3-t-butoxycarbonylaminopropionic acid and Example 10 as a starting material. Overall yield was 86%.

HCl salt was amorphous solid. $^1$H NMR (270 MHz, DMSOd$_6$) δ 10.96 (1H, br.s), 8.70–8.60 (1H, m), 8.19 (3H, br.s), 7.93–7.80 (2H, m), 7.73–7.65 (1H, m), 7.58–7.30 (6H, m), 5.50–5.30 (1H, m), 3.20–1.20 (24H, m).

MS(ESI positive) ml/z: 460(M+H)$^+$. IR(KBr): 3400, 2932, 1736, 1624, 1583 cm$^{-1}$ Anal. Calcd for $C_{28}H_{37}N_5O.2HCl.4.5H_2O$: C, 54.81; H, 7.88; N, 11.41. Found: C, 54.97; H, 7.64; N, 11.02.

Example 85
2-Amino-2-methyl-N-{1-[1-(1-phenylcycloheptyl)-4-piperidinyl]-1H-benzimidazol-2-yl}propanamide This was prepared according to the procedure described in Example 83 using 2-t-butoxycarbonylaminoisobutyric acid and Example 10 as a starting material. Overall yield was 38.1%.

HCl salt was amorphous solid. $^1$H NMR (270 MHz, DMSOd$_6$) δ 10.51 (1H, br.s), 8.32 (3H, br.s), 8.10–8.00 (1H, m), 7.95–7.85 (2H, m), 7.60–7.40 (5H, m), 7.27–7.20 (2H, m), 5.25–5.10 (1H, m), 3.30–3.15 (2H, m), 2.90–2.75 (2H, m), 2.65–2.50 (2H, m), 1.95–1.80 (4H, m), 1.70–1.25 (10H, m), 15 1.48 (6H, s).

MS(ESI positive) m/z: 474(M+H)$^+$. IR(KBr): 3400, 2934, 1730, 1624, 1555 cm$^{-1}$ Anal. Calcd for $C_{29}H_{39}N_5O.2HCl.4.2H_2O.1.2CH_2Cl_2$: C, 55.30; H, 7.91; N, 11.07. Found: C, 55.59; H, 7.49; N, 11.16.

Example 86
(2S,3S)-2-Amino-3-methyl-N-{1-[1-(1-phenylcycloheptyl)-4-piperidinyl]-1H-benzimidazol-2-yl}pentanamide This was prepared according to the procedure described in Example 83 using Boc-L-isoleucine Example 10 as a starting material, and diethyl phosphorocyanidate, N,N-diisopropylethylamine, and DMF instead of WSC and $CH_2Cl_2$ for coupling reaction. Overall yield was 28.8%.

HCl salt was amorphous solid. $^1$H NMR (270 MHz, DMSOd$_6$) δ 10.63 (1H, br.s), 8.29 (3H, br.s), 8.20–8.05 (1H, m), 30 7.95–7.85 (2H, m), 7.65–7.40 (5H, m), 7.35–7.20 (2H, m), 5.25–5.10 (1H, m), 3.30–315 (3H, m), 2.90–2.75 (2H, m), 2.15–2.50 (2H, m), 2.15–1.75 (6H, s), 1.70–1.20 (8H, m), 1.05–0.85 (6H, m).

MS(ESI positive) m/z: 502(M+H)$^+$. IR(KBr): 3395, 2934, 1736, 1578 cm$^{-1}$ Anal. Calcd for $C_{31}H_{43}N_5O.2HCl.4.6H_2O.0.4CH_2Cl_2$: C, 54.54; H, 8.02; N, 10.13. Found: C, 54.14; H, 7.65; N, 10.62.

Example 87
(2S)-2-Amino-3-methyl-N-{1-[1-(1-phenylcycloheptyl)-4-piperidinyl]-1H-benzimidazol-2-yl}butanamide This was prepared according to the procedure described in Example 86 using Example as a starting material. Overall yield was 33.7%. HCl salt was amorphous solid.

$^1$H NMR (270 MHz, DMSOd$_6$) δ 10.55 (1H, br.s), 8.23 (3H, br.s), 8.10–8.00 (1H, m), 7.93–7.85 (2H, m), 7.60–7.45 (5H, m), 7.35–7.20 (2H, m), 5.20–5.00 (1H, m), 3.30–3.15 (4H, m), 2.90–2.75 (2H, m), 2.65–2.50 (2H, m), 2.35–2.25 (1H, m), 1.95–1.80 (5H, m), 1.65–1.20 (8H, m), 1.03 (3H, d, J=6.6 Hz), 1.01 (3H, d, J=6.9 Hz).

MS(ESI positive) m/z: 488(M+H)$^+$. IR(KBr): 3396, 2934, 1734, 1580 cm$^{-1}$ Anal. Calcd for $C_{30}H_{41}N_5O.2HCl.4H_2O.0.35CH_2Cl_2$: C, 55.03; H, 7.87; N, 10.57. Found: C, 55.38; H, 7.73; N, 10.96.

Example 88

(2S)-2-Amino-N-1-[1-(1-phenylcycloheptyl)4piperidinyl]-1H-benzimidazol-2-yl}propanamide This was prepared according to the procedure described in Example 86 using (S)-Boc-alanine and Example 10 as a starting material. Overall yield was 20.8%. HCl salt was amorphous solid.

$^1$H NMR (270 MHz, DMSOd$_6$) δ 10.74 (1H, br.s), 8.36 (3H, br.s), 8.23 (1H, br.s), 7.95–7.85 (2H, m), 7.65–7.40 (5H, m), 7.35–7.20 (2H, m), 5.35–5.15 (1H, m), 3.50–3.10 (5H, m), 2.90–2.75 (2H, m), 2.65–2.50 (2H, m), 1.95–1.80 (5H, m), 1.65–1.20 (7H, m), 1.46 (3H, d, J=7.1 Hz). IR(KBr): 3408, 2932, 1736, 1626, 1582 cm$^{-1}$ Anal. Calcd for $C_{28}H_{37}N_5O.2HCl.3.7H_2O.0.1CH_2Cl_2$: C, 55.54; H, 7.73; N, 11.52. Found: C, 55.20; H, 7.34; N, 11.70.

Example 89

(2S)-2-Amino-4-(methylsuffanyl)-N-{1-[1-(1-phenylcycloheptyl)-4-piperidinyl]-1H-benzimidazol-2-yl}butanamide This was prepared according to the procedure described in Example 70 (S)-Boc-methionine using Example 10 as a starting material. Overall yield was 66.1%.

HCl salt was amorphous solid. $^1$H NMR (270 MHz, DMSOd$_6$) δ 10.72 (1H, br.s), 8.44 (3H, br.s), 8.18 (1H, br.s), 7.95–7.75 (2H, m), 7.60–7.40 (5H, m), 7.30–7.15 (2H, m), 5.30–5.10 (1H, m), 3.90–3.75 (1H, m), 3.55–3.10 (6H, m), 2.90–2.40 (4H, m), 2.20–2.00 (2H, m), 2.05 (3H, s), 1.95–1.75 (5H, m), 1.65–1.20 (7H, m). IR(KBr): 3404, 2930, 1734, 1624, 1582 cm$^{-1}$ Anal. Calcd for $C_{30}H_{41}N_5OS.2HCl.3.3H_2O.0.2CH_2Cl_2$: C, 54.21; H, 7.53; N, 10.47. Found: C, 54.35; H, 7.21; N, 10.49.

Example 90

(2S)-N-{1-[1-(1-Phenylcycloheptyl)4-piperidinyl]-1H-benzimidazol-2-yl}-2-pyrrolidinecarboxamide This was prepared according to the procedure described in Example 86 using (S)-Boc-proline and Example 10 as a starting material. Overall yield was 48.9%. HCl salt was amorphous solid.

$^1$H NMR (270 MHz, DMSOd$_6$) δ 10.70 (1H, br.s), 10.01 (1H, br.s), 8.67 (1H, br.s), 8.35–8.20 (1H, m), 8.00–7.85 (2H, m), 7.65–7.45 (4H, m), 7.35–7.20 (2H, m), 5.40–5.20 (1H, m), 4.35–4.15 (2H, m), 3.50–3.10 (9H, m), 2.90–2.75 (2H, m), 2.65–2.50 (2H, m), 2.40–2.25 (1H, m), 2.15–1.75 (6H, m), 1.65–1.20 (6H, m).

MS(ESI positive) m/z: 486(M+H)$^+$. IR(KBr): 3404, 2932, 1736, 1624, 1583 cm$^{-1}$ Anal. Calcd for $C_{30}H_{39}N_5O.2HCl.4H_2O.0.1CH_2Cl_2$: C, 56.56; H, 7.76; N, 10.96. Found: C, 56.27; H, 7.36; N, 11.16.

Example 91

4-Amino-N-{1-[1-(1-phenylcycloheptyl)-4-piperidinyl]-1H-benzimidazol-2-yl}butanamide This was prepared according to the procedure described in Example 83 using 4-t-butoxycarbonylaminobutyric acid and Example 10 as a starting material. Overall yield was 68%.

HCl salt was amorphous solid. $^1$H NMR (270 MHz, DMSOd$_6$) δ 11.06 (1H, br.s), 8.68 (1H, br.s), 8.16 (3H, br.s), 7.95–7.80 (2H, m), 7.80–7.65 (1H, m), 7.60–7.35 (5H, m), 5.65–5.35 (1H, m), 3.25–3.00 (6H, m), 3.00–2.70 (7H, m), 2.65–2.45 (2H, m), 2.20–1.75 (6H, m), 1.70–1.20 (6H, m). IR(KBr): 3412, 2935, 1734, 1624, 1583 cm$^{-1}$ Anal. Calcd for $C_{29}H_{39}N_5O.2HCl.4H_2O.0.1CH_2Cl_2$: C, 55.73; H, 7.91; N, 11.17. Found: C, 55.55; H, 7.55; N. 11.06.

Example 92

(2S)-2-Amino-3-methyl-3-(methylsulfanyl)-N-{1-[1-(1-phenylcycloheptyl)-4-piperidinyl]-1H-benzimidazol-2-yl}-1-butanamide This was prepared according to the procedure described in Example 83 using WSC and 1-hydroxybenzotriazole hydrate as coupling reagent, and N-t-Boc-S-methyl-L-penicillamine and Example 10 as a starting material. Overall yield was 78%.

HCl salt was amorphous solid. $^1$H NMR (270 MHz, DMSOd$_6$) δ 10.62 (1H, br.s), 8.40–8.00 (5H, m), 7.90–7.70 (2H, m), 7.50–7.30.(5H, m), 7.20–7.05 (2H, m), 5.30–5.00 (1H, m), 4.00–3.00 (5H, m), 2.80–2.60 (2H, m), 2.55–2.40 (3H, m), 1.96 (3H, s), 1.85–1.65 (4H, m), 1.55–1.10 (8H, m), 1.37 (3H, s), 1.26 (3H, s).

MS(ESI positive) m/z: 534(M+H)$^+$. IR(KBr):3387,2932, 1732, 1560cm$^{-1}$ Anal. Calcd for $C_{31}H_{45}N_5OS.2HCl.2H_2O.0.4CH_2Cl_2$: C, 55.57; H, 7.69; N, 10.32. Found: C, 55.49; H, 7.60; N, 10.34.

Example 93

(2R)-2-Amino-N-{1-[1-(1-phenylcycloheptyl)-4-piperidinyl]-1H-benzimidazol-2-yl}propanamide This was prepared according to the procedure described in Example 83 using (R)-Boc-alanine and Example 10 as a starting material. Overall yield was 77.6%.

HCl salt was amorphous solid. $^1$H NMR (270 MHz, DMSOd$_6$) δ 10.75 (1H, br.s), 8.37 (3H, br.s), 8.26 (1H, br.s), 7.95–7.85 (2H, m), 7.65–7.40 (4H, m), 7.35–7.20 (2H, m), 5.40–5.20 (1H, m), 4.00–3.10 (7H, m), 2.90–2.70 (2H, m), 2.65–2.45 (2H, m), 2.00–1.75 (4H, m), 1.65–1.20 (6H, m), 1.46 (3H, d, J=6.8 Hz).

MS(ESI positive) m/z: 460(M+H)$^+$ IR(KBr): 3396, 2934, 1736, 1582 cm$^{-1}$ Anal. Calcd for $C_{28}H_{37}N_5O.2HCl.3H_2O.0.5CH_2Cl_2$: C, 54.42; H, 7.37; N, 11.13. Found: C, 54.73; H, 7.28; N, 11.45.

Example 94

(2S)-2-Amino-3-phenyl-N-{1-[1-(1-phenylcycloheptyl)-4-piperidinyl]-1H-benzimidazol-2-yl}propanamide This was prepared according to the procedure described in Example 83 using (S)-Boc-phenylalanine and Example 10 as a starting material. Overall yield was 81%. HCl salt was amorphous solid.

$^1$H NMR (270 MHz, DMSOd$_6$) δ 10.74 (1H, br.s), 8.40 (3H, br.s), 8.18 (1H, br.s), 7.95–7.80 (2H, m), 7.60–7.40 (4H, m), 7.35–7.10 (7H, m), 5.10–4.85 (1H, m), 4.10–3.95 (1H, m), 3.30–3.00 (8H, m), 2.90–2.75 (2H, m), 2.65–2.40 (2H, m), 1.95–1.70 (4H, m), 1.65–1.15 (6H, m). MS(ESI positive) m/z: 536(M+H)$^+$ IR(KBr): 3396, 2932, 1734, 1622, 1578, 1558 cm$^{-1}$ Anal. Calcd for $C_{34}H_{41}N_5O.2HCl.2H_2O.0.5CH_2Cl_2$: C, 60.30; H, 7.04; N, 10.19. Found: C, 60.44; H, 6.80; N, 10.48.

Example 95

1-Amino-N-{1-[1-(1-phenylcycloheptyl)-4-piperidinyl]-1H-benzimidazol-2-yl}cyclopentanecarboxamide This was prepared according to the procedure described in Example 92 using 1-t-butoxycarbonylaminocyclopentanecarboxylic acid and Example 10 as a starting material. Overall yield was 80%.

HCl salt was amorphous solid. $^1$H NMR (270 MHz, DMSOd$_6$) δ 10.69 (1H, br.s), 8.40 (3H, br.s), 8.16 (1H, br.s), 7.95–7.85 (2H; m), 7.60–7.35 (4H, m), 7.30–7.10 (7H, m), 5.40–5.20 (1H, m), 3.50–3.15 (6H, m), 2.90–2.70 (2H, m), 2.65–2.40 (2H, m), 2.30–2.10 (2H, m), 2.00–1.70 (10H, m), 1.65–1.20 (6H, m).

MS(ESI positive) m/z: 500(M+H)$^+$ IR(KBr): 3398, 2934, 1724, 1556 cm$^{-1}$ Anal. Calcd for $C_{31}H_{41}N_5O.2HCl.3.2H_2O$: C, 59.08; H, 7.90; N, 11.11. Found: C, 59.08; H, 7.85; N, 10.89.

Example 96

(2R)-2-Amino-3-methyl-N-{1-[1-(1-phenylcycloheptyl)-4-piperidinyl]-1H-benzimidazol-2-yl}butanamide This was prepared according to the procedure described in Example 92 using (R)-Boc-valine and Example 10 as a starting material. Overall yield was 91%.

HCl salt was amorphous solid. $^1$H NMR (270 MHz, DMSOd$_6$) δ 10.73 (1H, br.s), 8.35 (3H, br.s), 8.20 (1H, br.s), 7.95–7.70 (2H, m), 7.60–7.30 (4H, m), 7.30–7.10 (2H, m), 5.35–5.15 (1H, m), 3.70–3.00 (7H, m), 2.90–2.70 (2H, m), 2.65–2.40 (2H, m), 2.40–2.20 (2H, m), 1.95–1.70 (4H, m), 1.65–1.15 (6H, m), 1.02 (3H, d, J=5.6 Hz), 1.00 (3H, d, J=5.1 Hz).

MS(ESI positive) m/z: 488(M+H)$^+$ IR(KBr): 3400, 2930, 1738, 1583 cm$^{-1}$ Anal. Calcd for $C_{30}H_{41}N_5O.2HCl.4.7H_2O$: C, 55.84; H, 8.18; N, 10.85. Found: C, 55.77; H, 7.79; N, 10.82.

Example 97
(2S)-2-Amino-4-(methylsulfonyl)-N-{1-[1-(1-phenylcycloheptyl)-4-piperidinyl]-1H-benzimidazol-2-yl}butanamide This was prepared according to the procedure described in Example 92 using (S)-Boc-methionine sulfone and Example 10 as a starting material. Overall yield was 85%.

HCl salt was amorphous solid. $^1$H NMR (270 MHz, DMSOd$_6$) δ 10.70 (1H, br.s), 8.52 (3H, br.s), 8.22 (1H, br.s), 8.00–7.80 (2H, m), 7.65–7.40 (4H, m), 7.35–7.15 (2H, m), 5.35–5.15 (1H, m), 4.10–3.10 (10H, m), 2.99 (3H, s), 2.90–2.70 (2H, m), 2.65–2.40 (2H, m), 2.40–2.20 (2H, m), 2.00–1.75 (4H, m), 1.65–1.20 (6H, m).

MS(ESI positive) m/z: 552(M+H)$^+$ IR(KBr): 3396, 2934, 1732, 1580 cm$^{-1}$ Anal. Calcd for $C_{30}H_{41}N_5O_3S.2HCl.4H_2O.0.5CH_3OH$: C, 51.40; H, 7.49; N, 9.83. Found: C, 51.57; H, 7.36; N, 9.56.

Example 98
2-Amino-3-(methylsulfinyl)-N-{1-[1-(-phenylcycloheptyl)-4piperidinyl]-1H-benzimidazol-2-yl}butanamide This was prepared according to the procedure described in Example 92 using Boc-methionine sulfoxide and Example 10 as a starting material. Overall yield was 79%.

HCl salt was amorphous solid. $^1$H NMR (270 MHz, DMSOd$_6$) δ 10.64 (1H, br.s), 8.48 (3H, br.s), 8.18 (1H, br.s), 7.95–7.70 (2H, m), 7.60–7.35 (4H, m), 7.30–7.15 (2H, m), 5.30–5.10 (1H, m), 4.00–3.10 (10H, m), 3.00–2.70 (4H, m), 2.56 and 2.54 (total 3H, each s), 2.35–2.20 (2H, m), 2.00–1.75 (4H, m), 1.65–1.15 (6H, m).

MS(ESI positive) m/z: 576(M+H)$^+$ IR(KBr): 3395, 2932, 1738, 1582 cm$^{-1}$ Anal. Calcd for $C_{30}H_{41}N_5O_2S.2HCl.5H_2O$: C, 51.57; H, 7.65; N, 10.02. Found: C, 51.60; H, 7.37; N, 10.01.

The chemical structures of the compounds of Formula (I) prepared in the Examples 1 to 98, are summarized in the following table. $Z^1$, $Z^2$, $Z^3$ and $Z^4$ of compounds prepared in the working examples are all hydrogen except for compounds of Example 45 wherein $Z^4$ is fluorine, Example 46 wherein $Z^2$ is fluorine and Exampel 47 wherein $Z^1$ is fuluorine.

TABLE

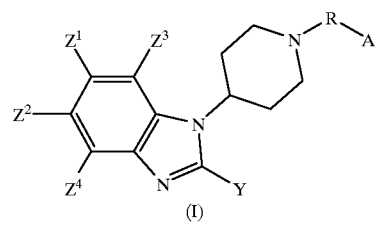

(I)

| Ex. # | R | A | Y | $Z^1$ to $Z^4$ |
|---|---|---|---|---|
| 1 | cycloheptyl | phenyl | Cl | H |
| 2 | cycloheptyl | phenyl | CH$_3$—NH— | H |
| 3 | cycloheptyl | phenyl | phenyl-NH— | H |
| 4 | cycloheptyl | phenyl | 4-CH$_3$-piperazin-1-yl | H |
| 5 | cycloheptyl | phenyl | N,N—(CH$_3$)$_2$—N— | H |
| 6 | cycloheptyl | phenyl | CH$_3$—O— | H |
| 7 | cycloheptyl | phenyl | CH$_3$—S— | H |
| 8 | cycloheptyl | phenyl | pyrrolidino | H |
| 9 | cycloheptyl | phenyl | morpholino | H |
| 10 | cycloheptyl | phenyl | NH$_2$ | H |
| 11 | cycloheptyl | phenyl | CH$_3$ | H |
| 12 | cycloheptyl | phenyl | H | H |
| 13 | cycloheptyl | phenyl | isopropyl | H |
| 14 | cycloheptyl | phenyl | phenyl | H |
| 15 | cycloheptyl | phenyl | benzyl | H |
| 16 | cycloheptyl | phenyl | cyclohexyl | H |
| 17 | cycloheptyl | phenyl | piperidino | H |
| 18 | cycloheptyl | benzyl | 4-benzylpiperazin-1-yl | H |
| 19 | cycloheptyl | phenyl | piperazino | H |
| 20 | cycloheptyl | phenyl | n-amyl-NH— | H |
| 21 | cycloheptyl | phenyl | cyclohexyl-NH— | H |
| 22 | cycloheptyl | phenyl | allyl-NH— | H |
| 23 | cycloheptyl | 4-fluorophenyl | 4-CH$_3$-piperazinyl | H |
| 24 | cyclooctyl | phenyl | 4-CH$_3$-piperazinyl | H |
| 25 | cycloheptyl | phenyl | 4-piperidinyl | H |
| 26 | cyclohexyl | phenyl | CH$_3$—NH— | H |
| 27 | cycloheptyl | phenyl | 2-NH$_2$-ethyl-NH— | H |
| 28 | cyclononyl | methyl | CH$_3$—NH— | H |
| 29 | cyclononyl | C$_2$H$_5$ | CH$_3$—NH— | H |

TABLE-continued

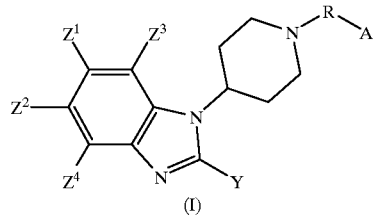

| Ex. # | R | A | Y | $Z^1$ to $Z^4$ |
|---|---|---|---|---|
| 30 | cyclononyl | phenyl | $NH_2$ | H |
| 31 | cyclononyl | 4-fluorophenyl | $NH_2$ | H |
| 32 | cycloheptyl | phenyl | $CH_3$—CONH— | H |
| 33 | cycloheptyl | phenyl | 2-guanidinoethyl-NH— | H |
| 34 | cycloheptyl | phenyl | piperidin-4-yl-NH— | H |
| 35 | cycloheptyl | phenyl | 2-$CH_3$NH-ethyl-NH— | H |
| 36 | cycloheptyl | phenyl | 2-$(CH_3)_2$N-ethyl-NH— | H |
| 37 | cycloheptyl | phenyl | 4-acetylpiperazino | H |
| 38 | cycloheptyl | phenyl | 4-phenylpiperazino | H |
| 39 | cycloheptyl | phenyl | 4-pyridinyl | H |
| 40 | cycloheptyl | phenyl | $CH_3$—$SO_2$— | H |
| 41 | cyclooctyl | methyl | 4-$CH_3$-piperazinyl | H |
| 42 | cyclononyl | methyl | 4-$CH_3$-piperazinyl | H |
| 43 | cyclononyl | methyl | 2-$NH_2$-ethyl-CO— | H |
| 44 | cycloheptyl | 4-F-phenyl | $CH_3$—NH— | H |
| 45 | cycloheptyl | benzyl | 4-$CH_3$-piperazin-1-yl | $Z^1$ to $Z^3$ are H $Z^4$ is F |
| 46 | cycloheptyl | phenyl | 4-$CH_3$-piperazin-1-yl | $Z^1$, $Z^3$ and $Z^4$ are H, $Z^2$ is F |
| 47 | cycloheptyl | phenyl | 4-$CH_3$-piperazin-1-yl | $Z^1$ is F, $Z^2$ to $Z^4$ are H |
| 48 | cyclohexyl | phenyl | 4-$CH_3$-piperazin-1-yl | H |
| 49 | cyclooctyl | $CH_3$ | $CH_3$—NH— | H |
| 50 | cyclooctyl | 4-fluorophenyl | H | H |
| 51 | cycloheptyl | phenyl | 4-oxo-piperidino | H |
| 52 | cycloheptyl | phenyl | 4-hydroxy-piperidino | H |
| 53 | cycloheptyl | phenyl | 4-ketoxime-piperidino | H |
| 54 | cycloheptyl | phenyl | 4-$NH_2$-piperidino | H |
| 55 | cycloheptyl | $CH_3$ | $CH_3$—NH— | H |
| 56 | cycloheptyl | $C_2H_5$ | $CH_3$—NH— | H |
| 57 | cycloheptyl | n-$C_3H_7$ | $CH_3$—NH— | H |
| 58 | cyclooctyl | n-$C_3H_7$ | $CH_3$—NH— | H |
| 59 | cycloheptyl | phenyl | 3-$NH_2$-n-propyl | H |
| 60 | cyclooctyl | $CH_3$ | 1-piperazinyl | H |
| 61 | cycloheptyl | phenyl | 1-guanidinyl-piperazin-4-yl | H |
| 62 | cyclooctyl | $CH_3$ | 4-guanidinyl-piperazin-1-yl | H |
| 63 | cycloheptyl | phenyl | piperidin-4-yl-O- | H |
| 64 | cycloheptyl | phenyl | 6-$NH_2$-n-hexyl-NH— | H |
| 65 | cycloheptyl | phenyl | 3-$NH_2$-azetidin-1-yl | H |
| 66 | cycloheptyl | phenyl | 4-$NH_2$-n-butyl-NH— | H |
| 67 | cycloheptyl | $CH_3$ | 4-$NH_2$-piperidino | H |
| 68 | cycloheptyl | $CH_3$ | 4-piperidyl | H |
| 69 | cycloheptyl | iso-$C_3H_7$ | 1-piperazinyl | H |
| 70 | cycloheptyl | phenyl | $NH_2$—$CH_2$—CONH— | H |
| 71 | cycloheptyl | phenyl | 2-$NH_2$—$C_2H_4$—O— | H |
| 72 | 4-cyclohepten-1-yl | phenyl | 4-$NH_2$-piperidino | H |
| 73 | cycloheptyl | phenyl | 8-$NH_2$-n-octanyl-NH— | H |
| 74 | cycloheptyl | $CH_3$ | 10-$NH_2$-n-decanyl-NH— | H |
| 75 | cycloheptyl | isopropyl | 4-$NH_2$-piperidino | H |
| 76 | cycloheptyl | phenyl | 4-$NH_2$-cyclohexan-1-yl-NH— | H |
| 77 | cycloheptyl | vinyl | 4-$NH_2$-piperidino | H |
| 78 | cycloheptyl | phenyl | 2-$NH_2$-2-$CH_3$-n-propyl-NH— | H |
| 79 | 4-cyclohepten-1-yl | phenyl | 1-piperazynyl | H |
| 80 | cycloheptyl | phenyl | 3-$NH_2$-n-propyl-$SO_2$ | H |
| 81 | cyclooctyl | phenyl | $NH_2$ | H |
| 82 | cyclooctyl | phenyl | $NH_2$—$CH_2$—CONH— | H |
| 83 | cycloheptyl | $CH_3$ | (2S,3S)-2-$NH_2$-3-$CH_3$-n-butyl-CONH— | H |
| 84 | cycloheptyl | phenyl | 2-$NH_2$—$C_2H_5$—CONH— | H |
| 85 | cycloheptyl | phenyl | 1-$NH_2$-1-$CH_3$-ethyl-CONH— | H |
| 86 | cycloheptyl | $CH_3$ | (2S,3S)-2-$NH_2$-3-$CH_3$-n-butyl-CONH— | H |
| 87 | cycloheptyl | phenyl | (1S)-1-$NH_2$-2-$CH_3$-n-proryl-CONH— | H |
| 88 | cycloheptyl | phenyl | (1S)-$NH_2$-ethyl-CONH— | H |
| 89 | cycloheptyl | phenyl | (1S)-$NH_2$-3-$CH_3$S-n-propyl-CONH— | H |
| 90 | cycloheptyl | phenyl | (2S)-2-pirrolidin-2-yl-CONH— | H |
| 91 | cycloheptyl | phenyl | 3-$NH_2$-n-propyl-CONH— | H |

TABLE-continued

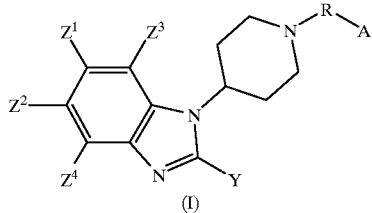

(I)

| Ex. # | R | A | Y | $Z^1$ to $Z^4$ |
|---|---|---|---|---|
| 92 | cycloheptyl | phenyl | (1S)-1-NH$_2$-2,2-CH$_3$CH$_3$S-n-propyl-CONH— | H |
| 93 | cycloheptyl | phenyl | (1R)-1-NH$_2$-ethyl-CONH | H |
| 94 | cycloheptyl | phenyl | (1S)-1-NH$_2$-2-phenyl-ethyl-CONH— | H |
| 95 | cycloheptyl | phenyl | 1-NH$_2$-2-cyclopentan-1-yl-CONH— | H |
| 96 | cycloheptyl | phenyl | (1R)-1-NH$_2$-2-CH$_3$-n-propyl-CONH— | H |
| 97 | cycloheptyl | phenyl | (1S)-NH$_2$-3-CH$_3$SO-n-propyl-CONH— | H |
| 98 | cycloheptyl | phenyl | 1-NH$_2$-3-CH$_3$SO-n-propyl-CONH— | H |

What is claimed is:

1. A compound of the following formula:

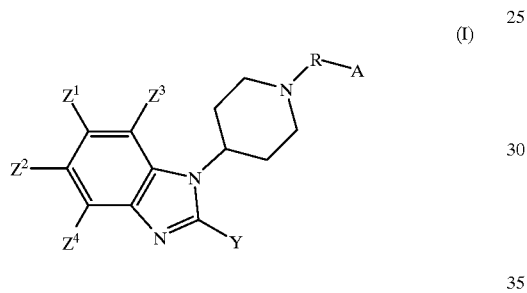

(I)

or a salt thereof, wherein

R is selected from the group consisting of ($C_3$–$C_{11}$) cycloalkyl, ($C_6$–$C_{16}$)bicycloalkyl, ($C_6$–$C_{16}$) tricycloalkyl and ($C_8$–$C_{16}$)tetracyclyoalkyl, wherein said groups are partially saturated, fully saturated or fully unsaturated and are optionally substituted with up to three substituents independently selected from the group consisting of halo, hydroxy, ($C_1$–$C_5$)alkyl and ($C_3$–$C_7$)cycloalkyl;

A is attached to the carbon atom of R with which R is attached to the nitrogen atom of the piperidine ring, and selected from the group consisting of ($C_1$–$C_7$)alkyl, mono-, di, or tri-halo ($C_1$–$C_7$)alkyl, ($C_2$–$C_5$)alkenyl, ($C_2$–$C_5$)alkynyl, phenyl-($C_1$–$C_5$)alkyl, aryl, and aromatic or non-aromatic heterocyclic comprising four to ten ring atoms wherein one to four ring atoms are independently selected from heteroatoms, and said phenyl moiety in phenyl-($C_1$–$C_5$)alkyl, aryl, or aromatic or non-aromatic heterocyclic being optionally substituted with up to three substituents independently selected from the group consisting of halo, hydroxy, ($C_1$–$C_4$)alkyl, halo ($C_1$–$C_4$)alkyl, ($C_1$–$C_4$) alkoxy, halo ($C_1$–$C_4$)alkoxy, ($C_1$–$C_4$)alkyl-CO—, phenyl, benzyl, —CHO, cyano, ($C_1$–$C_4$)alkyl-CO—, NH$_2$—CO—, NH$_2$—CH$_2$—, amino, ($C_1$–$C_4$)alkyl-NH—, di(($C_1$–$C_4$)alkyl)-N—, ($C_1$–$C_4$)alkyl-CO—NH—, ($C_1$–$C_4$)alkyl-NH—CO—, hydrazino, azido, ureido, amidino, guanidino, oxo and =N—OH;

Y is selected from the group consisting of hydrogen, halo, amino, mercapto, ($C_1$–$C_{12}$)alky-M—, ($C_3$–$C_7$) cycloalkyl-M—, ($C_2$–$C_6$)alkenyl-M—, aryl-M—, aromatic or non-aromatic heterocyclic-M—, aryl-($C_1$–$C_5$) alkyl-M—, aromatic or non-aromatic heterocyclic-($C_1$–$C_5$)alkyl-M—, said aromatic or non-aromatic heterocyclic moiety of said groups comprising four to ten ring atoms wherein one to four ring atoms are independently selected from heteroatoms, and M is selected from the group consisting of a covalent bond, O, S, SO, SO$_2$, CO, NQ, NQCO, and CONQ, wherein Q is selected from the group consisting of hydrogen and ($C_1$–$C_6$)alkyl, said ($C_1$–$C_{12}$)alkyl, ($C_3$–$C_7$) cycloalkyl or ($C_2$–$C_6$)alkenyl moiety in said groups being optionally substituted with up to three substituents independently selected from the group consisting of halo, hydroxy, amino, ($C_1$–$C_4$)alkyl-NH—, di-($C_1$–$C_4$)alkyl-N—, hydrazino, azido, ureido, amidino, guanidino, ($C_1$–$C_4$)alkoxy, ($C_1$–$C_4$)alkyl-S—, ($C_1$–$C_4$) alkyl-SO— and ($C_1$–$C_4$)alkyl-SO$_2$—, and said aryl, or aromatic or non-aromatic heterocyclic moiety of said groups being optionally substituted with up to three substituents independently selected from the group consisting of halo, hydroxy, ($C_1$–$C_4$) alkyl, halo ($C_1$–$C_4$)alkyl, ($C_1$–$C_4$)alkoxy, halo ($C_1$–$C_4$)alkoxy, ($C_1$–$C_4$)alkyl-CO—, phenyl, benzyl, —CHO, cyano, ($C_1$–$C_4$)alkyl-CO—, NH$_2$—CO—, NH$_2$—CH$_2$—, amino, ($C_1$–$C_4$)alkyl-NH—, di($C_1$–$C_4$ alkyl)-N—, ($C_1$–$C_4$)alkyl-CO—NH—, ($C_1$–$C_4$)alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, ($C_1$–$C_4$)alkyl, halo ($C_1$–$C_4$)alkyl, ($C_1$–$C_4$)alkoxy, ($C_1$–$C_4$)alkylsulfonyl, ($C_1$–$C_4$)alkyl-CO—, carboxy, ($C_1$–$C_4$)alkyl-COO—, amino, NH$_2$CO—, ($C_1$–$C_4$)alkyl-CO—NH—, ($C_1$–$C_4$) alkyl-SO$_2$—NH—, phenyl and naphthyl.

2. A compound according to claim 1 or a salt thereof, wherein

R is selected from the group consisting of ($C_3$–$C_{11}$) cycloalkyl and ($C_3$–$C_{11}$)cycloalkenyl, said groups being optionally substituted with up to three substituents independently selected from the group consisting of halo, hydroxy, ($C_1$–$C_5$)alkyl and ($C_3$–$C_7$)cycloalkyl;

A is attached to the carbon atom of R with which R is attached to the nitrogen atom of the piperidine ring, and selected from the group consisting of ($C_1$–$C_7$)alkyl, mono-, di- or tri-halo ($C_1$–$C_7$)alkyl, ($C_2$–$C_5$)alkenyl, ($C_2$–$C_5$)alkynyl, aryl, and aromatic or non-aromatic heterocyclic comprising four to six ring atoms wherein one to two ring atoms are independently selected from heteroatoms, and aryl, or aromatic or non-aromatic heterocyclic wherein each of said aforementioned groups is optionally substituted with up to three substituents independently selected from halo, $(C_1-C_4)$alkyl , halo $(C_1-C_4)$alkyl, $(C_1-C_4)$alkoxy, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl)-N—, $(C_1-C_4)$alkyl-CO—NH— and $(C_1-C_4)$alkyl-NH—CO—;

Y is selected from the group consisting of hydrogen, halo, amino, mercapto, $(C_1-C_{10})$alkyl-M—, $(C_3-C_7)$cycloalkyl-M—, $(C_2-C_6)$alkenyl-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aromatic or non-aromatic heterocyclic moiety of said groups comprising four to six ring atoms wherein one to two ring atoms are independently selected from heteroatoms, M is selected from group consisting of a covalent bond, O, S, SO, $SO_2$, CO, NH, N($(C_1-C_6)$alkyl), CONH and NHCO, said $(C_1-C_{10})$alkyl, $(C_3-C_7)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with substituents independently selected from the group consisting of halo, hydroxy, $(C_1-C_4)$alkyl, halo $(C_1-C_4)$alkyl, $(C_1-C_4)$alkoxy, $(C_1-C_4)$alkyl-CO—, phenyl, benzyl, amino, $(C_1-C_4)$alkyl-NH—, di$((C_1-C_4)$alkyl)-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH; and $Z^1$, $Z^2$, $Z^3$ and $Z^4$ are independently selected from the group consisting of hydrogen and halo.

3. A compound according to claim 2 or a salt thereof, wherein

R is selected from the group consisting of $(C_3-C_{11})$cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, $(C_1-C_4)$alkyl, halo $(C_1-C_4)$alkyl and $(C_1-C_4)$alkoxy;

Y is selected from the group consisting of hydrogen, amino, mercapto, $(C_1-C_{10})$alkyl-M—, $(C_3-C_7)$cycloalkyl-M—, $(C_2-C_6)$alkenyl-M—, aryl-M—, aromatic or non-aromatic heterocyclic-M—, aryl-$(C_1-C_5)$alkyl-M—, and aromatic or non-aromatic heterocyclic-$(C_1-C_5)$alkyl-M—, said aryl moiety of said groups being selected from the group consisting of phenyl and naphthyl, said aromatic or non-aromatic heterocyclic moiety of said groups being selected from the group consisting of azetidinyl, furyl, pyrrolidinyl, thienyl, pyridyl, piperidyl, piperidino, morpholinyl, morphorino, pyrazinyl, pyridazinyl, aziridinyl, pyrrolidinyl, piperazinyl and thiamorpholino, M is selected from the group consisting of a covalent bond, O, S, SO, $SO_2$, CO, NH, CONH, N($(C_1-C_6)$alkyl) and NHCO, said $(C_1-C_{10})$alkyl, $(C_3-C_7)$cycloalkyl and $(C_2-C_6)$alkenyl moiety of said groups being optionally substituted with up to three substituents independently selected from the group consisting of halo, hydroxy, amino, $(C_1-C_4)$alkyl-NH—, di$(C_1-C_4)$alkyl-N—, hydrazino, azido, ureido, amidino, guanidino, $(C_1-C_4)$alkyl-S—, $(C_1-C_4)$alkyl-SO— and $(C_1-C_4)$alkyl-$SO_2$—, and said aryl, or aromatic or non-aromatic heterocyclic moiety of said groups being optionally substituted with up to three substituents selected from the group consisting of halo, hydroxy, $(C_1-C_4)$alkyl, halo $(C_1-C_4)$alkyl, $(C_1-C_4)$alkoxy, $(C_1-C_4)$alkyl-CO—, phenyl, benzyl, amino, $(C_1-C_4)$alkyl-NH—, di$((C_1-C_4)$alkyl)-N—, $(C_1-C_4)$alkyl-CO—NH—, $NH_2$—CO—, $(C_1-C_4)$alkyl-NH—CO—, hydrazino, azido, ureido, amidino, guanidino, oxo and =NOH; and $Z^1$ and $Z^2$ are independently selected from the group consisting of hydrogen and halo;

and $Z^3$ and $Z^4$ are both hydrogen.

4. A compound according to claim 3 or a salt thereof, wherein

R is $(C_6-C_{10})$cycloalkyl;

A is attached to the carbon atom of R with which R is attached to the nitrogen atom of the piperidine ring, and is selected from the group consisting of $(C_1-C_7)$alkyl and $(C_2-C_5)$alkenyl, phenyl and naphthyl;

Y is selected from the group consisting of hydrogen, amino, $(C_1-C_6)$alkyl-M—, piperidyl, piperidino and piperazinyl, M is selected from group consisting of a covalent bond, O, $SO_2$, CO, NH, CONH and NHCO, said alkyl moiety of $(C_1-C_6)$alkyl-M— being optionally substituted with up to three substituents independently selected from the group consisting of amino and guanidino, and said piperidyl, piperidino or piperazinyl being optionally substituted with up to three substituents independently selected from $(C_1-C_4)$alkyl; and $Z^1$, $Z^2$, $Z^3$ and $Z^4$ are all hydrogen.

5. A compound according to claim 4 or a salt thereof, wherein

R is $(C_7-C_9)$cycloalkyl;

A is attached to the carbon atom of R with which R is attached to the nitrogen atom of the piperidine ring, and is selected from the group consisting of methyl and phenyl;

Y is selected from the group consisting of amino, $(C_1-C_6)$alkyl-NH—, amino-$(C_1-C_6)$alkyl-O—, amino-$(C_1-C_6)$alkyl-CONH—, amino-$(C_1-C_6)$alkyl-$SO_2$— and piperazinyl substituted by $(C_1-C_4)$alkyl; and $Z^1$, $Z^2$, $Z^3$ and $Z^4$ are all hydrogen.

6. A compound according to claim 1 selected from the group consisting of

N-methyl-1-[1-(1-phenylcycloheptyl)-4-piperidinyl]-1H-benzimidazol-2-amine;

2-(4-methylpiperazino)-1-[1-(1-phenylcycloheptyl)-4-piperidinyl]-1H-benzimidazole;

1-[1-(1-phenylcycloheptyl)-4-piperidinyl]-1H-benzimidazole;

2-(4-methylpiperazino)-1-[1-(1-phenylcyclooctyl)-4-piperidinyl]-1H-benzimidazole;

1-[1-(1-phenylcycloheptyl)-4-piperidinyl]-2-(4-piperidinyl)-1H-benzimidazole;

N-methyl-1-[1-(1-methylcyclononyl)-4-piperidinyl]-1H-benzimidazol-2-amine;

1-[1-(1-phenylcyclononyl)-4-piperidinyl]-1H-benzimidazol-2-amine;

N-{1-[1-(1-phenylcycloheptyl)-4-piperidinyl]-1H-benzimidazol-2-yl}acetamide;

2-(4-methylpiperazino)-1-[1-(1-methylcyclooctyl)-4-piperidinyl]-1H-benzimidazole;

3-amino-1-{1-[1-(1-phenylcycloheptyl)-4-piperidinyl]-1H-benzimidazol-2-yl}-1-propanone;

N-methyl-1-[1-(1-methylcyclooctyl)-4-piperidinyl]-1H-benzimidazol-2-amine;

4-{1-[1-(1-phenylcycloheptyl)-4-piperidinyl]-1H-benzimidazol-2-yl}-1-piperidinecarboximidamide;

4-{1-[1-(1-methylcyclooctyl)-4-piperidinyl]-1H-benzimidazol-2-yl}1-piperazinecarboximidamide;

2-amino-N-{1-[1-(1-phenylcycloheptyl)-4-piperidinyl]-1H-benzimidazol-2-yl}acetamide;

2-({1-[1-(1-phenylcycloheptyl)-4-piperidinyl]-1H-benzimidazol-2-yl}oxy)-1-ethanamine;

3-({1-[1-(1-phenylcycloheptyl)-4-piperidinyl]-1H-benzimidazol-2-yl}sulfonyl)-1-propanamine;

1-[1-(1-phenylcyclooctyl)-4-piperidinyl]-1H-benzimidazol-2-amine;

2-amino-N-{1-[1-(1-phenylcyclooctyl)-4-piperidinyl]-1H-benzimidazol-2-yl}acetamide; and (2S)-2-amino-N-{1-[1-(1-phenylcycloheptyl)-4-piperidinyl]-1H-benzimidazol-2-yl}propanamide; or a salt thereof.

7. A compound according to claim 6 selected from the group consisting of 2-(4-methylpiperazino)-1-[1-(1-phenylcycloheptyl)-4-piperidinyl]-1H-benzimidazole;

1-[1-(1-phenylcyclononyl)-4-piperidinyl]-1H-benzimidazol-2-amine;

N-methyl-1-[1-(1-methylcyclooctyl)-4-piperidinyl]-1H-benzimidazol-2-amine;

2-amino-N-{1-[1-(1-phenylcycloheptyl)-4-piperidinyl]-1H-benzimidazol-2-yl}acetamide;

2-({1-[1-(1-phenylcycloheptyl)-4-piperidinyl]-1H-benzimidazol-2-yl}oxy)-1-ethanamine;

3-({1-[1-(1-phenylcycloheptyl)-4-piperidinyl]-1H-benzimidazol-2-yl}sulfonyl)-1-propanamine; and 2-amino-N-{1-[1-(1-phenylcyclooctyl)-4-piperidinyl]-1H-benzimidazol-2-yl}acetamide; or a salt thereof.

8. A pharmaceutical composition for the treatment of a disorder or condition mediated by ORL1-receptor and its endogenous ligands in a mammal, or for anesthetizing a mammal, which comprises an effective amount of the compound of claim 1, or a pharmaceutically acceptable salt thereof, and a pharmaceutically acceptable carrier.

9. A method of treating a disorder or condition, or anesthetizing a mammal, the treatment and anesthetization of which can be effected or facilitated by activating ORL1-receptor in a mammal, comprising administering to a mammal in need of such treatment an effective amount of a compound of claim 1 or a pharmaceutically acceptable salt thereof.

10. A process for preparing a compound of formula (I) according to claim 1 wherein R is selected from the group consisting of $(C_3–C_{11})$ cycloalkyl, $(C_6–C_{16})$bicycloalkyl, $(C_6–C_{16})$ tricycloalkyl and $(C_8–C_{16})$tetracyclyoalkyl, wherein said groups are partially saturated, fully saturated or fully unsaturated and are optionally substituted with up to three substituents independently selected from the group consisting of halo, hydroxy, $(C_1–C_5)$alkyl and $(C_3–C_7)$cycloalkyl;

A is attached to the carbon atom of R with which R is attached to the nitrogen atom of the piperidine ring, and selected from the group consisting of $(C_1–C_7)$alkyl, mono-, di, or tri-halo $(C_1–C_7)$alkyl, $(C_2–C_5)$alkenyl, $(C_2–C_5)$alkynyl, phenyl-$(C_1–C_5)$alkyl, aryl, and aromatic or non-aromatic heterocyclic comprising four to ten ring atoms wherein one to four ring atoms are independently selected from heteroatoms, and said phenyl moiety in phenyl-$(C_1–C_5)$alkyl, aryl, or aromatic or non-aromatic heterocyclic being optionally substituted with up to three substituents independently selected from the group consisting of halo, hydroxy, $(C_1–C_4)$alkyl, halo $(C_1C_4)$alkyl, $(C_1–C_4)$ alkoxy, halo $(C_1–C_4)$alkoxy, $(C_1–C_4)$alkyl-CO—, phenyl, benzyl, —CHO, cyano, $(C_1–C_4)$alkyl-CO—, $NH_2$—CO—, $NH_2$—$CH_2$—, amino, $(C_1–C_4)$alkyl-NH—, di(($C_1–C_4$)alkyl)-N—, $(C_1–C_4)$alkyl-CO—NH—, $(C_{1–4})$alkyl-NH—CO—, hydrazino, azido, ureido, amidino, guanidino, oxo and =N—OH;

Y is selected from the group consisting of hydrogen, halo, amino, mercapto, $(C_1–C_{12})$alkyl-M—, $(C_3–C_7)$ cycloalkyl-M—, $(C_2–C_6)$alkenyl-M—, aryl-M—, aromatic or non-aromatic heterocyclic-M—, aryl-$(C_1–C_5)$ alkyl-M—, aromatic or non-aromatic heterocyclic-$(C_1–C_5)$alkyl-M—, said aromatic or non-aromatic heterocyclic moiety of said groups comprising four to ten ring atoms wherein one to four ring atoms are independently selected from heteroatoms, and M is selected from the group consisting of a covalent bond, O, S, SO, $SO_2$, CO, NQ, NQCO, and CONQ, wherein Q is selected from the group consisting of hydrogen and $(C_1–C_6)$alkyl, said $(C_1–C_{12})$alkyl, $(C_3–C_7)$cycloalkyl or $(C_2–C_6)$alkenyl moiety in said groups being optionally substituted with up to three substituents independently selected from the group consisting of halo, hydroxy, amino, $(C_1–C_4)$alkyl-NH—, di-$(C_1–C_4)$alkyl-N—, hydrazino, azido, ureido, amidino, guanidino, $(C_1–C_4)$alkoxy, $(C_1–C_4)$alkyl-S—, $(C_1–C_4)$ alkyl-SO— and $(C_1–C_4)$alkyl-$SO_2$—, and said aryl, or aromatic or non-aromatic heterocyclic moiety of said groups being optionally substituted with up to three substituents independently selected from the group consisting of halo, hydroxy, $(C_1–C_4)$ alkyl, halo $(C_1–C_4)$alkyl, $(C_1–C_4)$alkoxy, halo $(C_1–C_4)$alkoxy, $(C_1–C_4)$alkyl-CO—, phenyl, benzyl, —CHO, cyano, $(C_1–C_4)$alkyl-CO—, $NH_2$—CO—, $NH_2$—$CH_2$—, amino, $(C_1–C_4)$alkyl-NH—, di($C_1–C_4$ alkyl)-N—, $(C_1–C_4)$alkyl-CO—NH—, $(C_1–C_4)$alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, $(C_1–C_4)$alkyl, halo $(C_1-C_4)$alkyl, $(C_1-C_4)$alkoxy, $(C_1-C_4)$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$alkyl-$SO_2$—NH—, phenyl and naphthyl, which comprises (a) coupling compounds of formulae

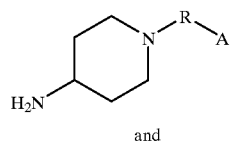

(VII)

and

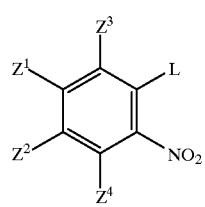

(VIII)

wherein R, A and $Z^1$ to $Z^4$ are defined as above, and L is halo to give the compound of formula

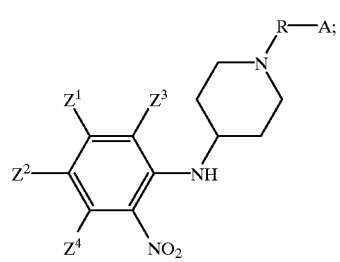

(IX)

(b) reducing the compound of formula (IX) to the compound of formula (X)

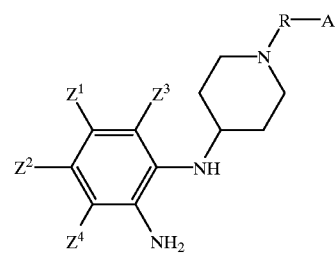

(X)

by either reduction or hydrogenation; and (c) subjecting the resulting compound of formula (X) to benzimidazole formation to give the compound of formula (I).

11. A process of claim 10 wherein in step (a), the coupling reaction is carried out in the presence of a base in a reaction inert solvent at a temperature in the range from room temperature to the reflux temperature of the reaction mixture for from 0.5 to 48 hours;

in step (b), the reduction is carried out in the presence of a reducing reagent in a reaction inert solvent at a temperature in the range from room temperature to the reflux temperature of the reaction mixture for from 0.5 to 48 hours, and the hydrogenation is carried out in the presence of a metal catalyst at a temperature in the range from 0° to 100° C. under hydrogen atmosphere in a reaction inert solvent for from 0.5 to 48 hours; and in step (c), benzimidazole formation is carried out with a coupling reagent selected from the group consisting of carboxylic acids, amino carboxylic acids, acid anhydrides, formamides, alkylcarbonyl halides, aryl carbonyl halides, aryl alkyl carbonyl halides, heteroaryl carboxylic acids, carbon disulfides, cyanogen halides, cyanamide and trialkyl orthoformates, in the presence of a peptide coupling reagent in a reaction inert solvent at a temperature in the range from 0° C. to the reflux temperature of the reaction mixture for from 1 minutes to 120 hours.

12. A process of claim 11 wherein, in step (a), the base is selected from the group consisting of $K_2CO_3$, and amines;

in step (b), the reducing reagent is selected from the group consisting of $SnCl_2$, zinc catalysts and iron catalysts, and the metal catalyst used in the hydrogenation is selected from the group consisting of Raney nickel catalysts, palladium catalysts and platinum catalysts; and in step (c), the peptide coupling reagent used in the benzimidazole formation is selected from the group consisting of dicyclohexylcarbodiimide (DCC), diisopropylcarbodiimide (DIPC), 1-ethyl-3-(3-dimethylaminopropyl)carbodiimide (WSC), benzotriazole-1-yloxy-tris(dimethylamino)phosphonium hexafluorophosphate (BOP) and diphenylphosphorylazide (DPPA).

13. A compound of formula

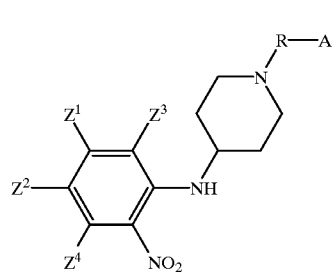

(IX)

wherein

R is selected from the group consisting of $(C_3-C_{11})$cycloalkyl, $(C_6-C_{16})$bicycloalkyl, $(C_6-C_{16})$tricycloalkyl and $(C_8-C_{16})$tetracyclyoalkyl, wherein said groups are partially saturated, fully saturated or fully unsaturated and are optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di, or tri-halo $(C_1-C_7)$alkyl, $(C_2-C_5)$alkenyl, $(C_2-C_5)$alkynyl, phenyl-$(C_1-C_5)$alkyl, aryl, and aromatic or non-aromatic heterocyclic comprising four to ten ring atoms wherein one to four ring atoms are independently selected from heteroatoms, and said phenyl moiety in phenyl-$(C_1-C_5)$alkyl, aryl, or aromatic or non-aromatic heterocyclic being optionally substituted with up to three substituents independently selected from the group consisting of halo, hydroxy, $(C_1-C_4)$alkyl, halo $(C_1-C_4)$alkyl, $(C_1-C_4)$alkoxy, halo $(C_1-C_4)$alkoxy, $(C_1-C_4)$alkyl-CO—, phenyl, benzyl, —CHO, cyano, $(C_1-C_4)$alkyl-CO—, $NH_2$—CO—, $NH_2$—$CH_2$—, amino, $(C_1-C_4)$alkyl-NH—, di($(C_1-C_4)$alkyl)-N—, $(C_1-C_4)$alkyl-CO—NH—, $(C_{1-4})$alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, $(C_1-C_4)$alkyl, halo $(C_1-C_4)$alkyl, $(C_{1-4})$alkoxy, $(C_{1-4})$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$alkyl-SO$_2$—NH—, phenyl and naphthyl.

14. A compound of claim 13 wherein

R is selected from the group consisting of $(C_3-C_{11})$cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four to six ring atoms wherein one to two ring atoms are independently selected from heteroatoms, and aryl, or aromatic or non-aromatic heterocyclic wherein each of said aforementioned groups is optionally substituted with up to three substituents independently selected from halo, $(C_1-C_4)$alkyl , halo $(C_1-C_4)$alkyl, $(C_1-C_4)$alkoxy, —CHO, cyano, $(C_1-C_4)$alkyl-CO—, $NH_2$—CO—, $NH_2$—$CH_2$—, amino, $(C_1-C_4)$alkyl-NH—, di($(C_1-C_4)$alkyl)-N—, $(C_1-C_4)$alkyl-CO—NH— and $(C_1-C_4)$alkyl-NH—CO—; and $Z^1$, $Z^2$, $Z^3$ and $Z^4$ are independently selected from the group consisting of hydrogen and halo.

15. A compound according to claim 14, wherein

R is selected from the group consisting of $(C_3-C_{11})$cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, $(C_1-C_4)$alkyl, halo $(C_1-C_4)$alkyl and $(C_1-C_4)$alkoxy; and $Z^1$ and $Z^2$ are independently selected from the group consisting of hydrogen and halo;

and $Z^3$ and $Z^4$ are both hydrogen.

16. A compound according to claim 15 wherein

R is $(C_6-C_{10})$cycloalkyl;

A is attached to the carbon atom of R with which R is attached to the nitrogen atom of the piperidine ring, and selected from the group consisting of $(C_1-C_7)$alkyl and $(C_2-C_5)$alkenyl, phenyl and naphthyl; and $Z^1$, $Z^2$, $Z^3$ and $Z^4$ are all hydrogen.

17. A compound according to claim 16 wherein

R is $(C_7-C_9)$cycloalkyl;

A is attached to the carbon atom of R with which R is attached to the nitrogen atom of the piperidine ring, and selected from the group consisting of methyl and phenyl; and $Z^1$, $Z^2$, $Z^3$ and $Z^4$ are all hydrogen.

18. A compound of formula

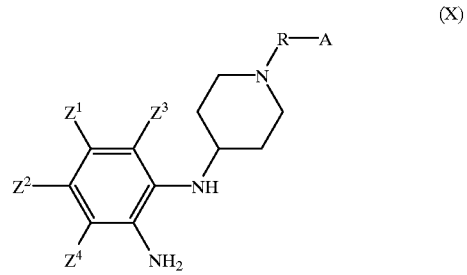

(X)

wherein

R is selected from the group consisting of $(C_3-C_{11})$cycloalkyl, $(C_6-C_{16})$bicycloalkyl, $(C_6-C_{16})$tricycloalkyl and $(C_8-C_{16})$tetracyclyoalkyl, wherein said groups are partially saturated, fully saturated or fully unsaturated and are optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di, or tri-halo $(C_1-C_7)$alkyl, $(C_2-C_5)$alkenyl, $(C_2-C_5)$alkynyl, phenyl-$(C_1-C_5)$alkyl, aryl, and aromatic or non-aromatic heterocyclic comprising four to ten ring atoms wherein one to four ring atoms are independently selected from heteroatoms, and said phenyl moiety in phenyl-$(C_1-C_5)$alkyl, aryl, or aromatic or non-aromatic heterocyclic being optionally substituted with up to three substituents independently selected from the group consisting of halo, hydroxy, $(C_1-C_4)$alkyl, halo $(C_1-C_4)$alkyl, $(C_1-C_4)$alkoxy, halo $(C_1-C_4)$alkoxy, $(C_1-C_4)$alkyl-CO—, phenyl, benzyl, —CHO, cyano, $(C_1-C_4)$alkyl-CO—, $NH_2$—CO—, $NH_2$—$CH_2$—, amino, $(C_1-C_4)$alkyl-NH—, di($(C_1-C_4)$alkyl)-N—, $(C_1-C_4)$alkyl-CO—NH—, $(C_1-C_4)$alkyl-NH—CO—, hydrazino, azido, ureido, amidino, guanidino, oxo and =N—OH; and $Z^1$, $Z^2$, $Z^3$ and $Z^4$ are independently selected from the group consisting of hydrogen, halo, $(C_1-C_4)$alkyl, halo $(C_1-C_4)$alkyl, $(C_1-C_4)$alkoxy, $(C_1-C_4)$alkylsulfonyl, $(C_1-C_4)$alkyl-CO—, carboxy, $(C_1-C_4)$alkyl-COO—, amino, $NH_2CO$—, $(C_1-C_4)$alkyl-CO—NH—, $(C_1-C_4)$alkyl-SO$_2$—NH—, phenyl and naphthyl.

19. A compound of claim 18 wherein

R is selected from the group consisting of $(C_3-C_{11})$cycloalkyl and $(C_3-C_{11})$cycloalkenyl, said groups being optionally substituted with up to three substituents independently selected from the group consisting of halo, hydroxy, $(C_1-C_5)$alkyl and $(C_3-C_7)$cycloalkyl;

A is attached to the carbon atom of R with which R is attached to the nitrogen atom of the piperidine ring, and selected from the group consisting of $(C_1-C_7)$alkyl, mono-, di- or tri-halo $(C_1-C_7)$alkyl, $(C_2-C_5)$alkenyl, $(C_2-C_5)$alkynyl, aryl, and aromatic or non-aromatic heterocyclic comprising four to six ring atoms wherein one to two ring atoms are independently selected from heteroatoms, and aryl, or aromatic or non-aromatic heterocyclic wherein each of said aforementioned groups is optionally substituted with up to three substituents independently selected from halo, $(C_1-C_4)$alkyl, halo $(C_1-C_4)$alkyl, $(C_1-C_4)$alkoxy, —CHO, cyano, $(C_1-C_4)$alkyl-CO—, $NH_2$—CO—, $NH_2$—$CH_2$—, amino, $(C_1-C_4)$alkyl-NH—, di$((C_1-C_4)$alkyl)-N—, $(C_1-C_4)$alkyl-CO—NH— and $(C_1-C_4)$alkyl-NH—CO—; and $Z^1$, $Z^2$, $Z^3$ and $Z^4$ are independently selected from the group consisting of hydrogen and halo.

20. A compound according to claim 19, wherein

R is selected from the group consisting of $(C_3-C_{11})$cycloalkyl, $(C_3-C_{11})$cycloalkenyl, mono-, di- or tri-halo $(C_3-C_{11})$cycloalkyl, mono-, di- or tri-halo $(C_3-C_{11})$cycloalkenyl;

A is attached to the carbon atom of R with which R is attached to the nitrogen atom of the piperidine ring, and selected from the group consisting of $(C_1-C_7)$alkyl, $(C_2-C_5)$alkenyl, aryl selected from the group consisting of phenyl and naphthyl, and aromatic-heterocyclic selected from the group consisting of furyl, thienyl, pyrrolyl, oxazolyl, isooxazolyl, thiazolyl, isothiazolyl, imidazolyl, pyrazolyl, triazolyl, furazanyl, tetrazolyl, pyranyl, pyridyl, oxazinyl, thiazinyl, pyridazinyl, pyrimidinyl, pyrazinyl and triazinyl, said aryl or aromatic heterocyclic being optionally substituted with up to three substituents independently selected from the group consisting of halo, $(C_1-C_4)$alkyl, halo $(C_1-C_4)$alkyl and $(C_1-C_4)$alkoxy; and $Z^1$ and $Z^2$ are independently selected from the group consisting of hydrogen and halo;

and $Z^3$ and $Z^4$ are both hydrogen.

21. A compound according to claim 20 wherein

R is $(C_6-C_{10})$cycloalkyl;

A is attached to the carbon atom of R with which R is attached to the nitrogen atom of the piperidine ring, and selected from the group consisting of $(C_1-C_7)$alkyl and $(C_2-C_5)$alkenyl, phenyl and naphthyl; and $Z^1$, $Z^2$, $Z^3$ and $Z^4$ are all hydrogen.

22. A compound according to claim 21 wherein

R is $(C_7-C_9)$cycloalkyl;

A is attached to the carbon atom of R with which R is attached to the nitrogen atom of the piperidine ring, and selected from the group consisting of methyl and phenyl; and $Z^1$, $Z^2$, $Z^3$ and $Z^4$ are all hydrogen.

* * * * *